United States Patent

Taguchi et al.

[11] Patent Number: 5,838,756
[45] Date of Patent: Nov. 17, 1998

[54] RADIATION COMPUTED TOMOGRAPHY APPARATUS

[75] Inventors: Katsuyuki Taguchi; Tadaharu Kobayashi, both of Tochigi-ken, Japan

[73] Assignee: Kabushiki Kaisha Toshiba, Kawasaki, Japan

[21] Appl. No.: 778,820

[22] Filed: Jan. 3, 1997

[30] Foreign Application Priority Data

Jan. 8, 1996 [JP] Japan .................................. 8-001015
Jan. 9, 1996 [JP] Japan .................................. 8-001213

[51] Int. Cl.⁶ .................................................. A61B 6/03
[52] U.S. Cl. .................................... 378/4; 378/901
[58] Field of Search ................... 378/4, 15, 19, 378/901

[56] References Cited

U.S. PATENT DOCUMENTS

| | | | |
|---|---|---|---|
| 4,149,247 | 4/1979 | Pavkovich t al. ...................... | 378/14 |
| 5,377,250 | 12/1994 | Hu ........................................... | 378/15 |
| 5,430,783 | 7/1995 | Hu et al. ................................. | 378/15 |
| 5,473,654 | 12/1995 | Kotian et al. .......................... | 378/4 |
| 5,684,855 | 11/1997 | Aradate et al. ........................ | 378/4 |

FOREIGN PATENT DOCUMENTS 55-99240  7/1980  Japan .

OTHER PUBLICATIONS

L. A. Feldkamp, et al. "Practical Cone–Beam Algorithm", J. Optical Society of America, vol. 1, No. 6, (pp. 612–619), Jun., 1984.

Primary Examiner—David P. Porta
Assistant Examiner—David Vernon Bruce
Attorney, Agent, or Firm—Oblon, Spivak, McClelland, Maier & Neustadt, P.C.

[57] ABSTRACT

A radiation CT apparatus comprises a radiation source for irradiating a subject with radiations, detection section having at least two detector columns to detect radiations allowed to pass through the subject, section for obtaining data to be backprojected in accordance with data detected by the detection section, and image reconstruction section for reconstructing a transmitted image of the subject, wherein the image reconstructing section includes first backprojection section for backprojecting detected data to a predetermined centering plane, and second backprojection section for backprojecting data backprojected to the centering plane to the voxels corresponding to backprojected data.

31 Claims, 27 Drawing Sheets

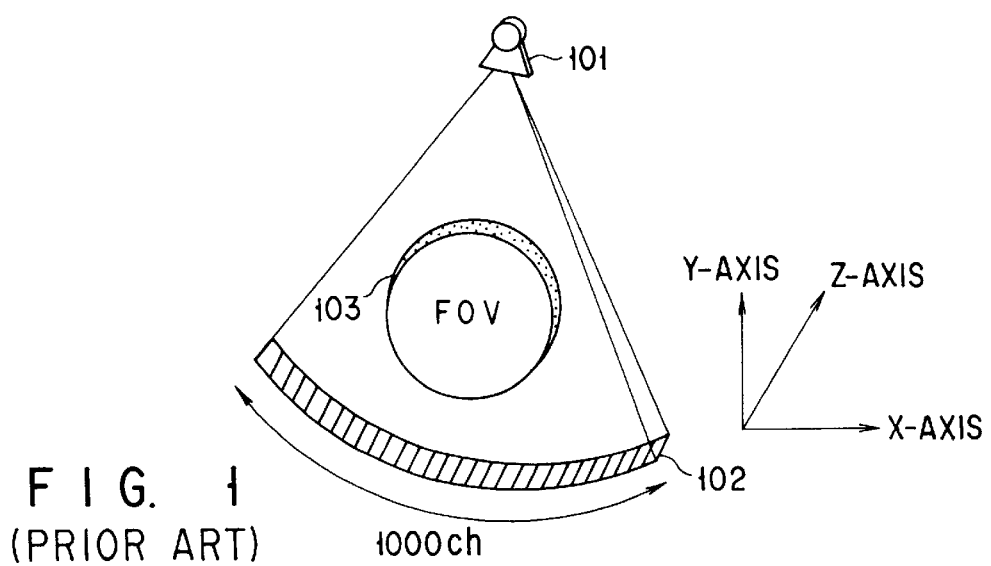
FIG. 1 (PRIOR ART)
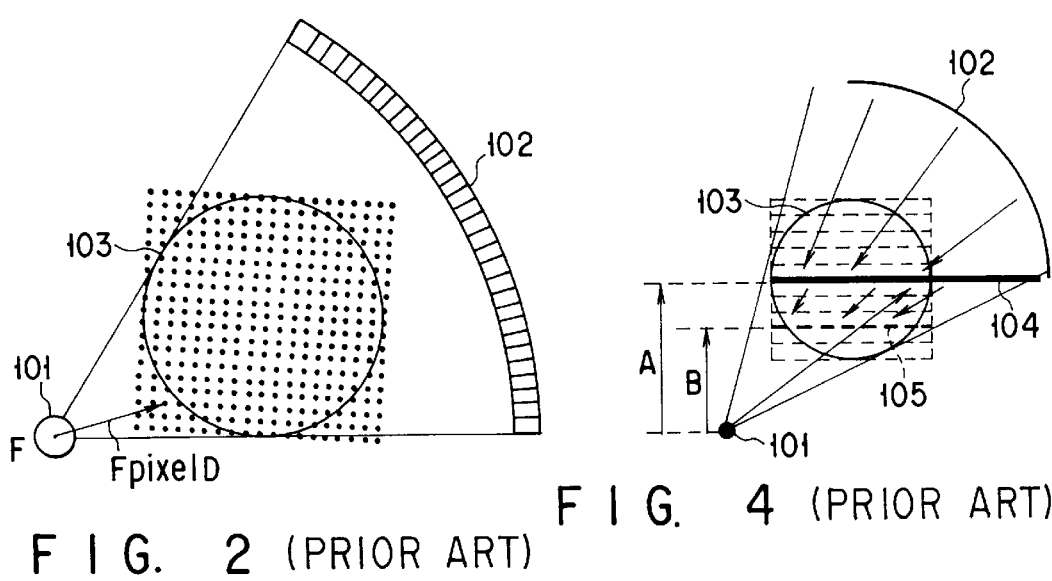
FIG. 2 (PRIOR ART)
FIG. 4 (PRIOR ART)
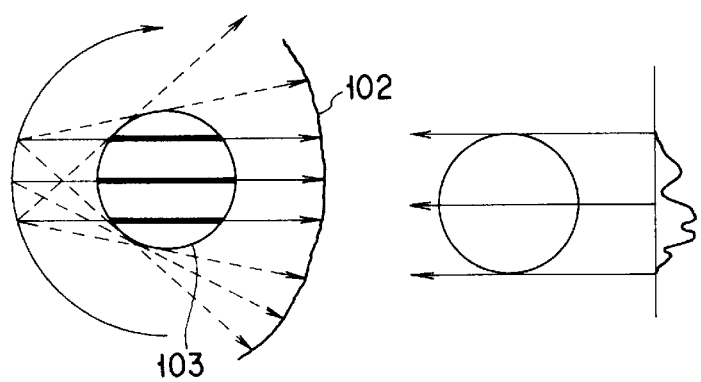
FIG. 3 (PRIOR ART)

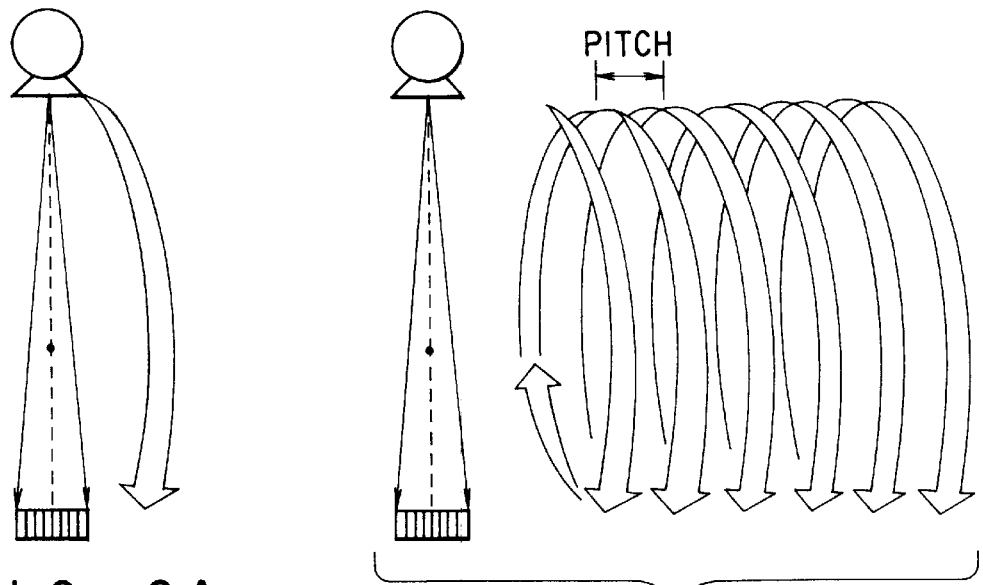
F I G. 9A
(PRIOR ART)
F I G. 9B (PRIOR ART)
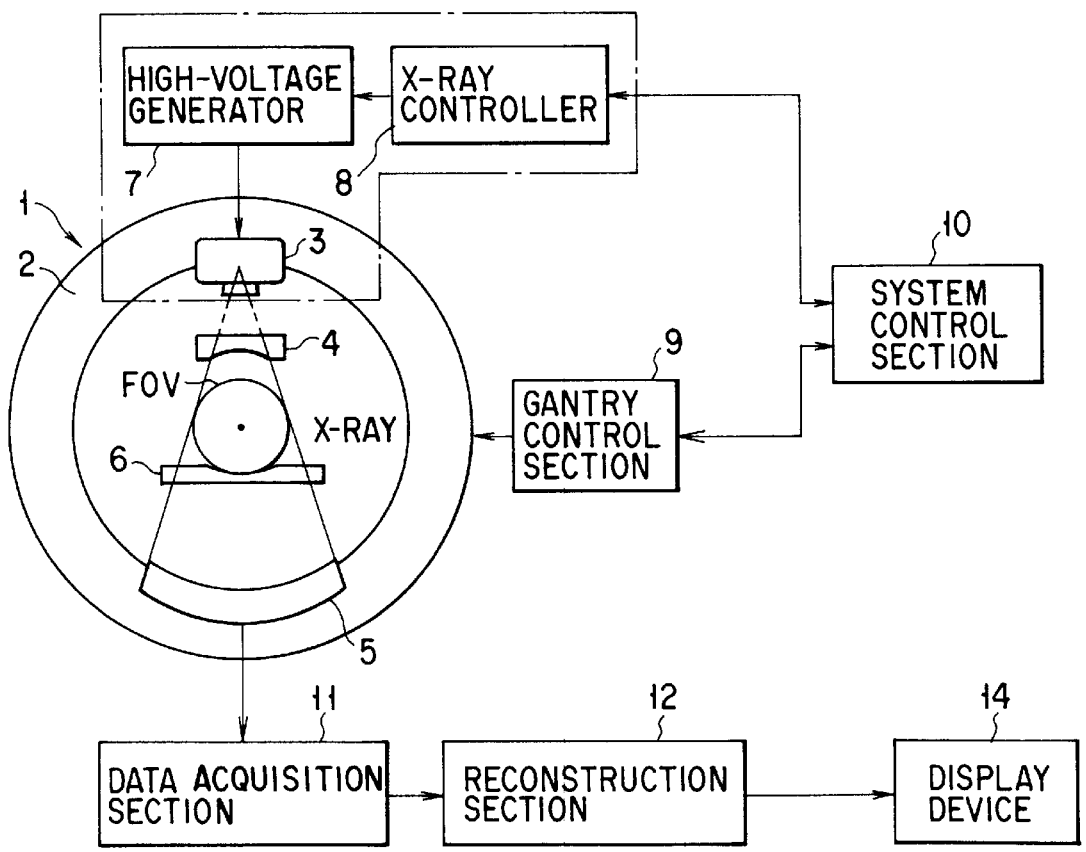
F I G. 10

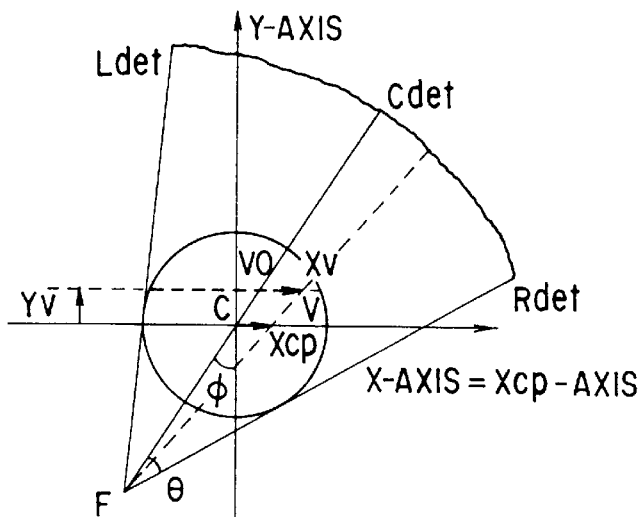
F I G. 16A
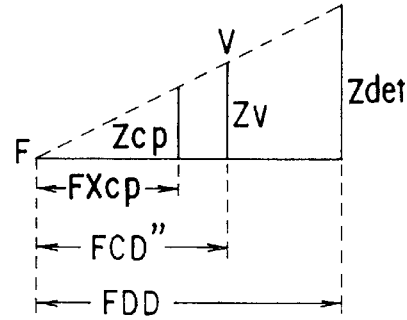
F I G. 16B
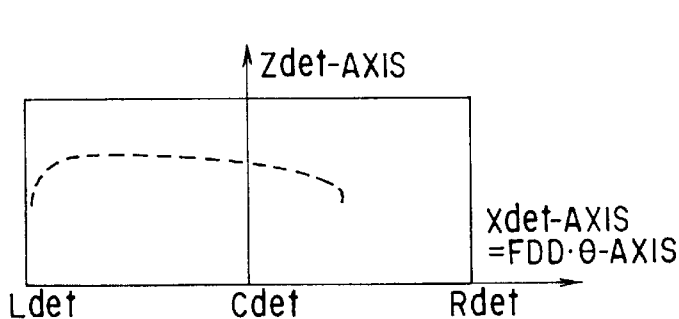
F I G. 16D
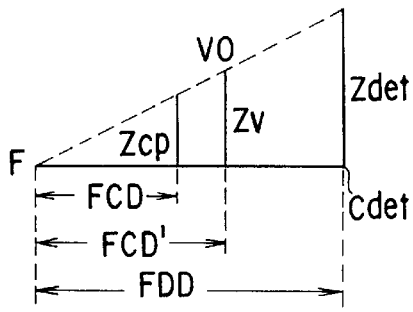
F I G. 16C
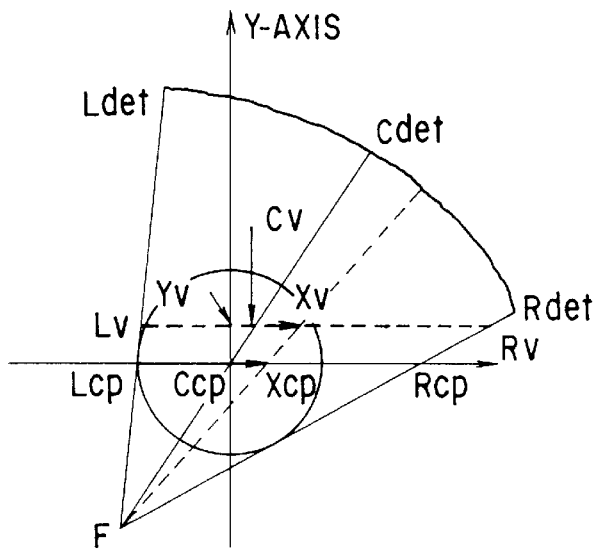
F I G. 17

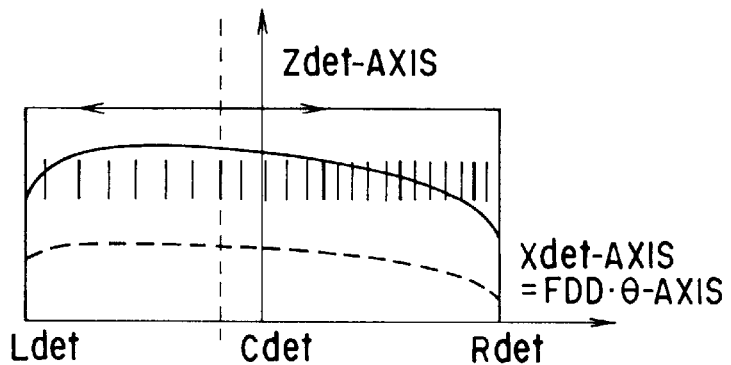
FIG. 18C
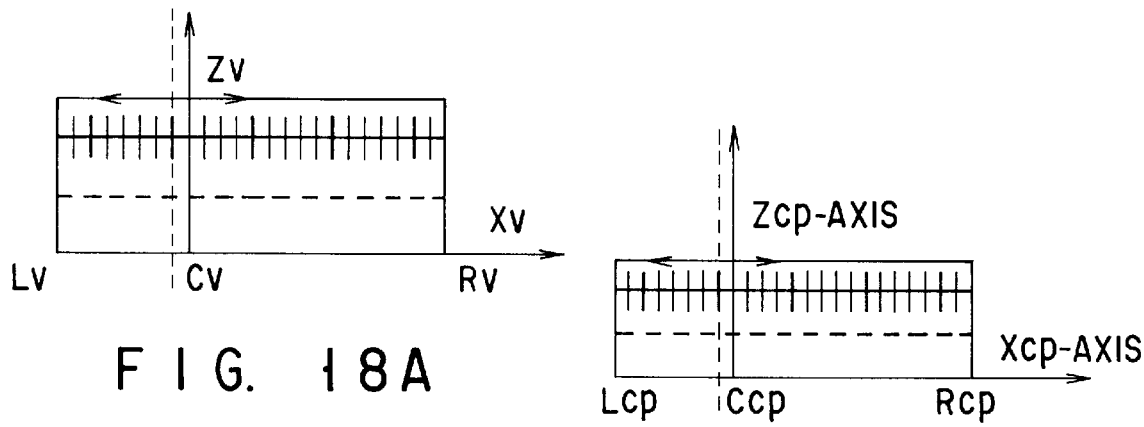
FIG. 18A
FIG. 18B
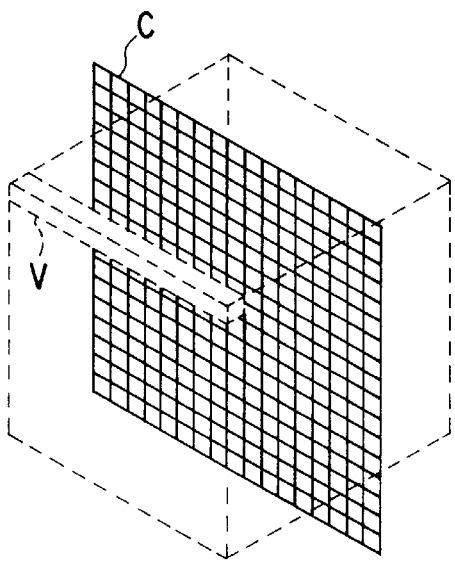
FIG. 19

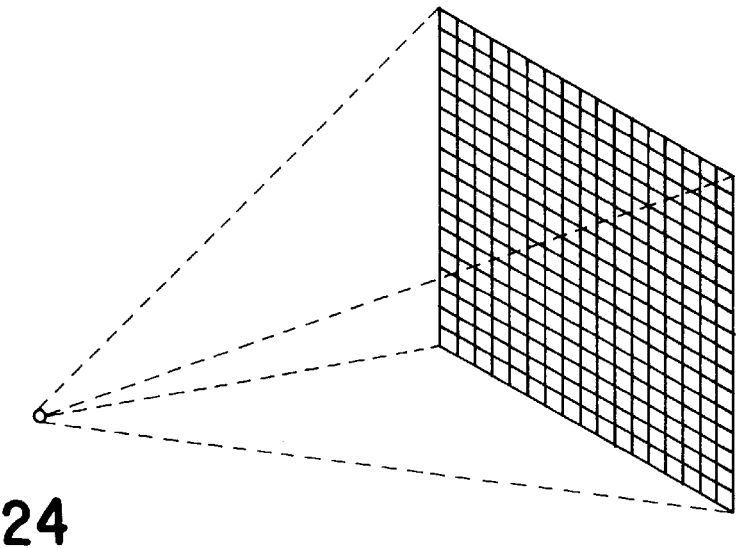
F I G. 24
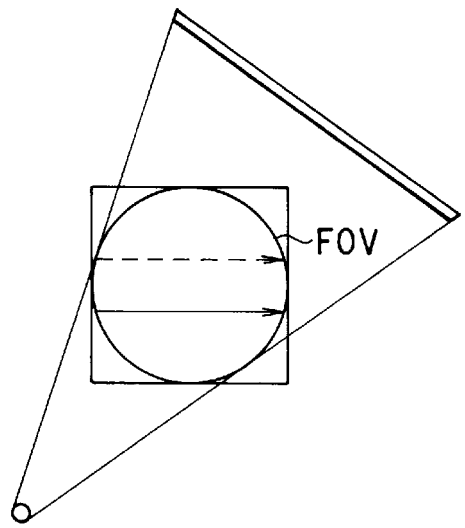
F I G. 25
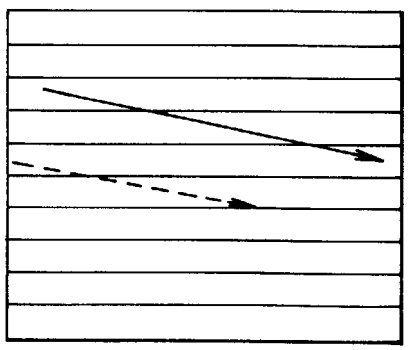
F I G. 26
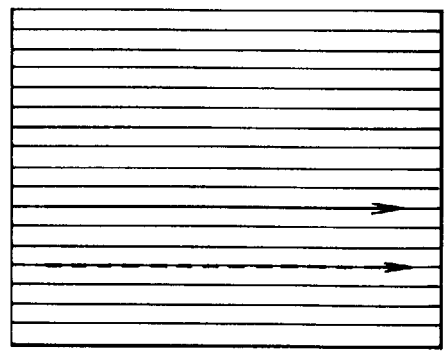
F I G. 27

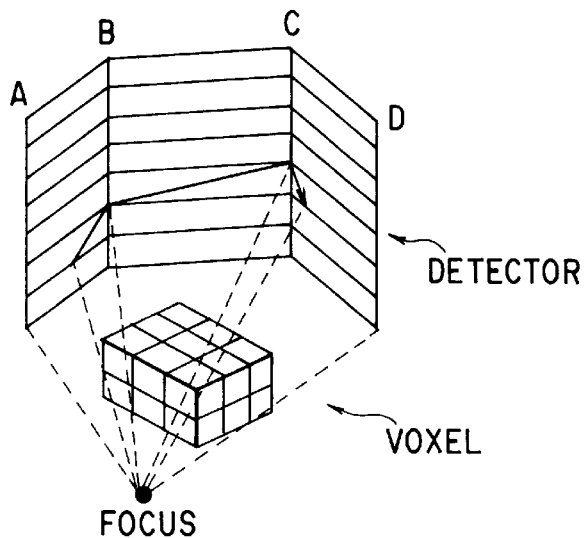
FIG. 28
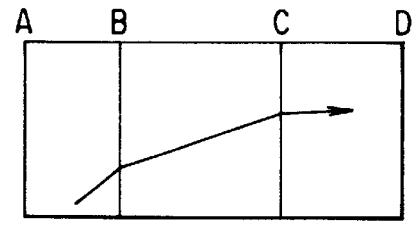
FIG. 29
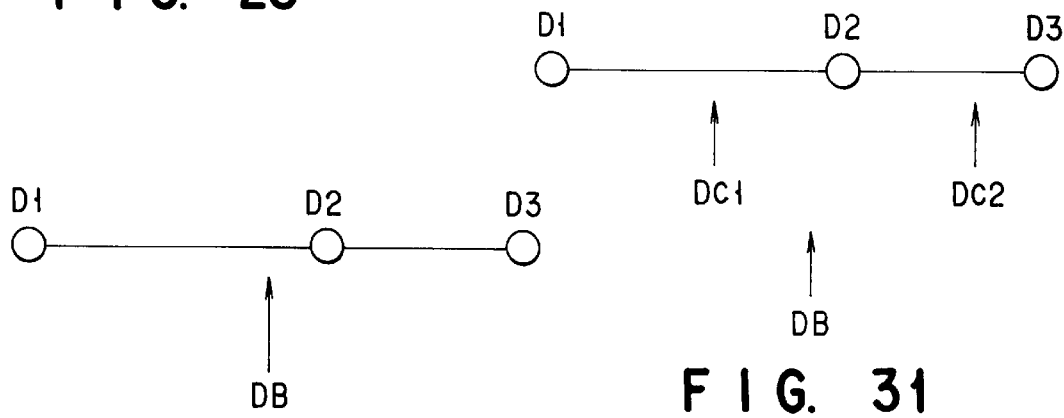
FIG. 30
FIG. 31
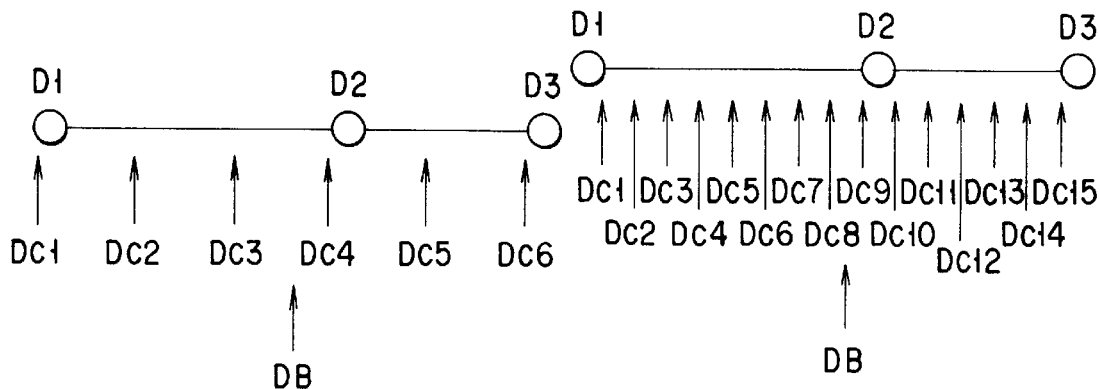
FIG. 32
FIG. 33

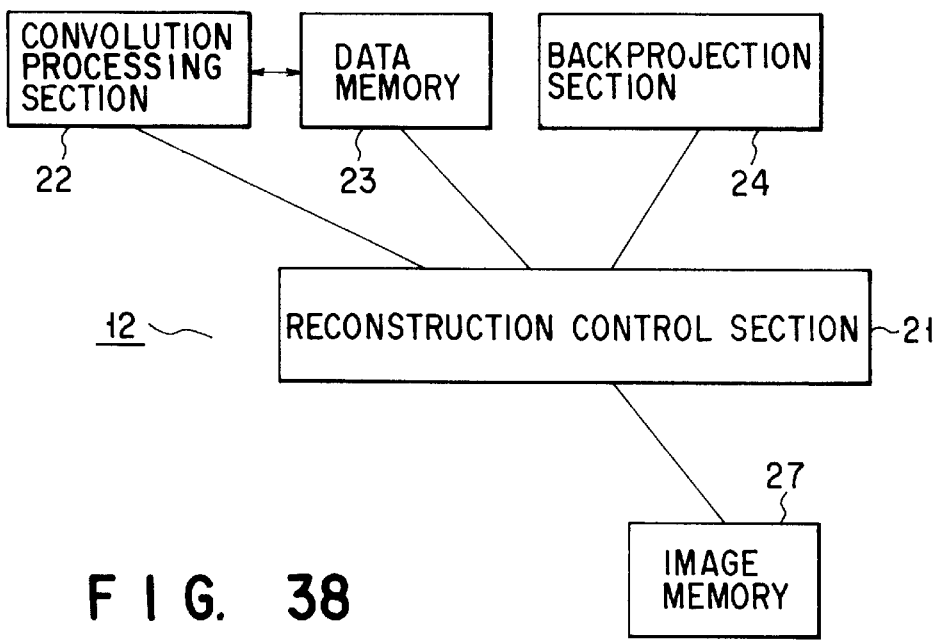
F I G. 38
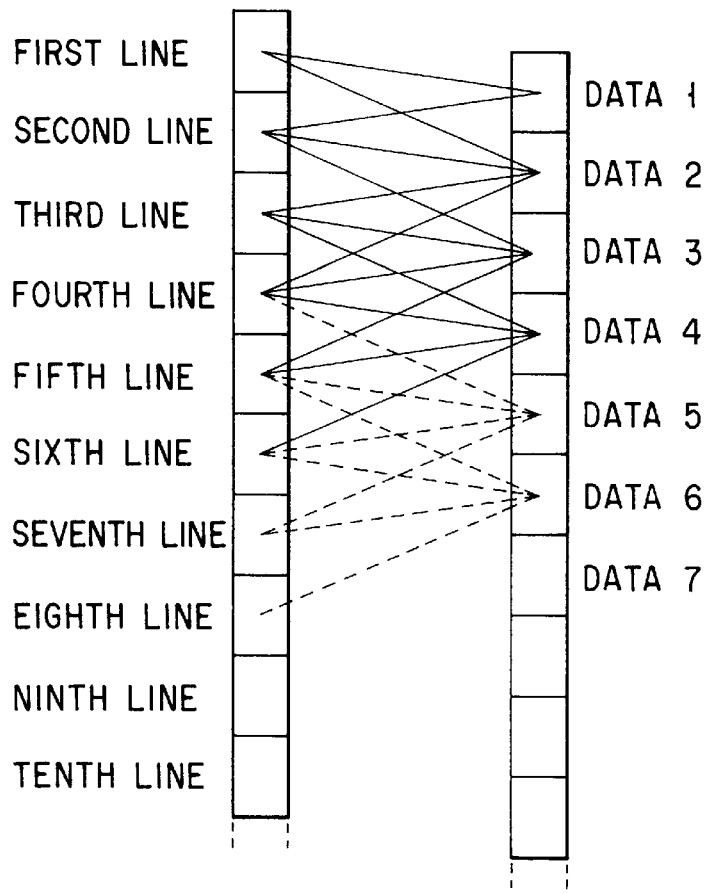
F I G. 39

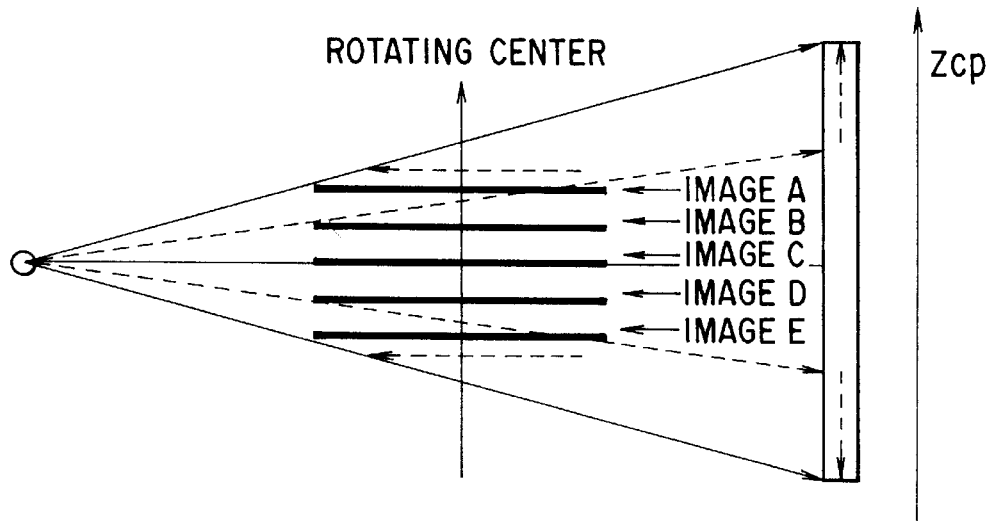
F I G. 42
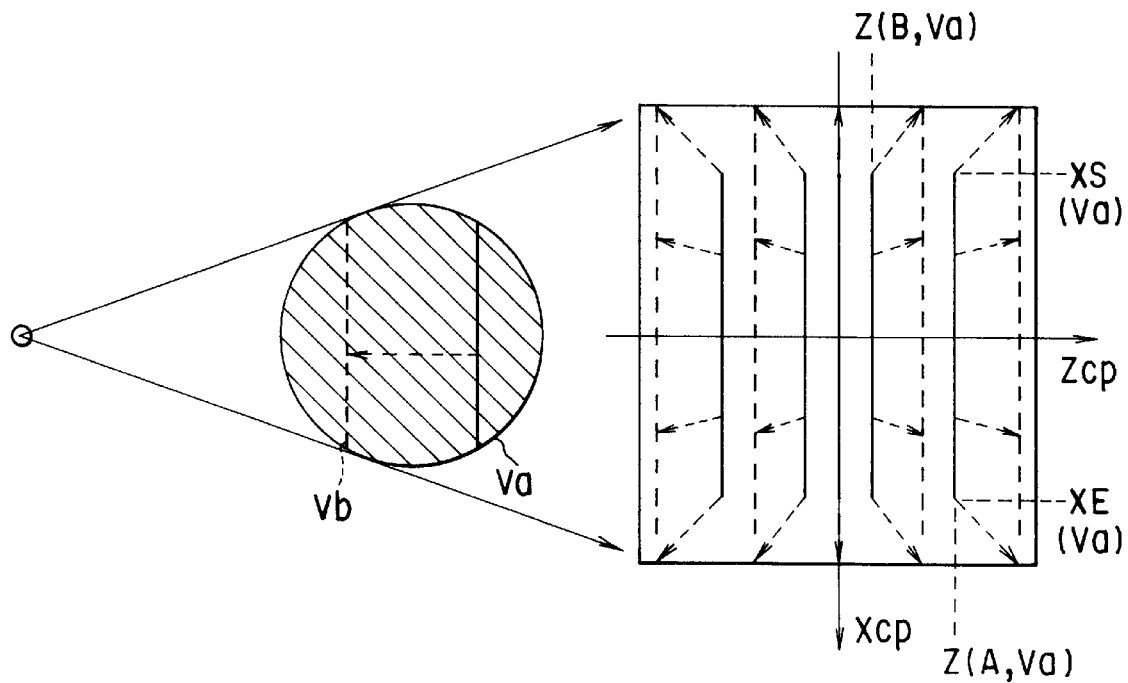
F I G. 43

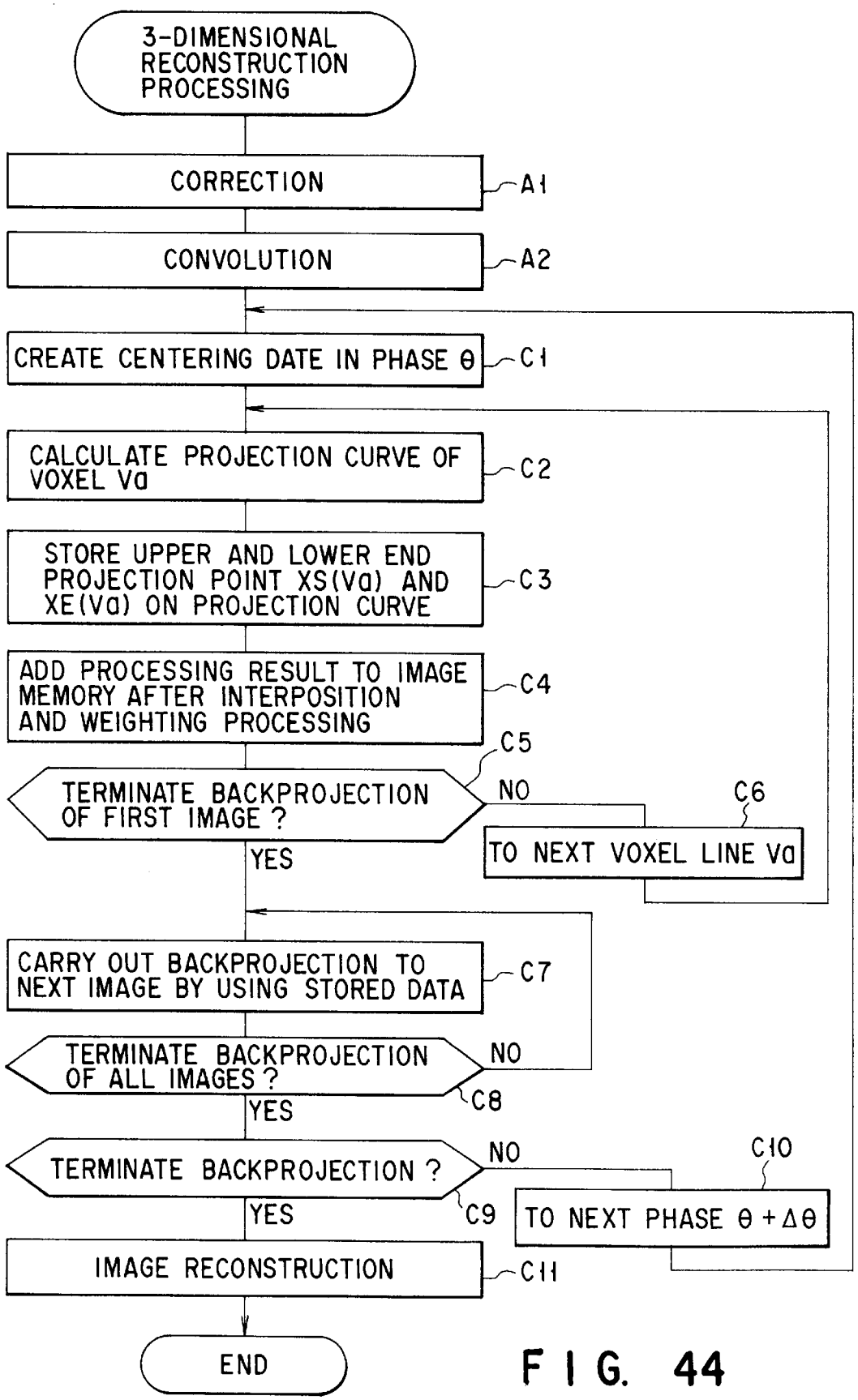
F I G. 44

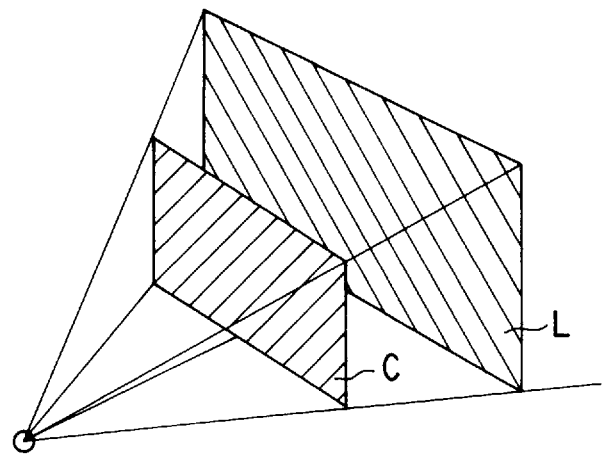
F I G. 45
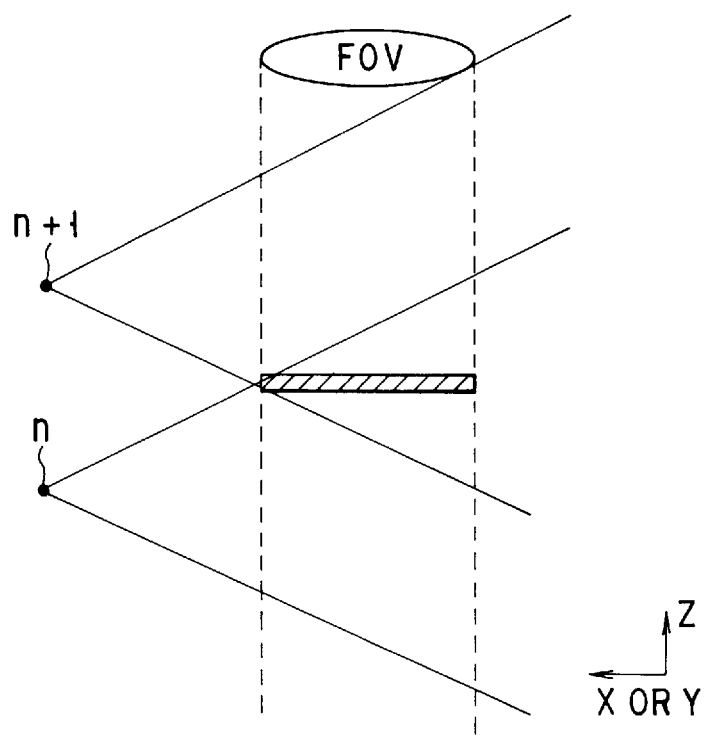
F I G. 46

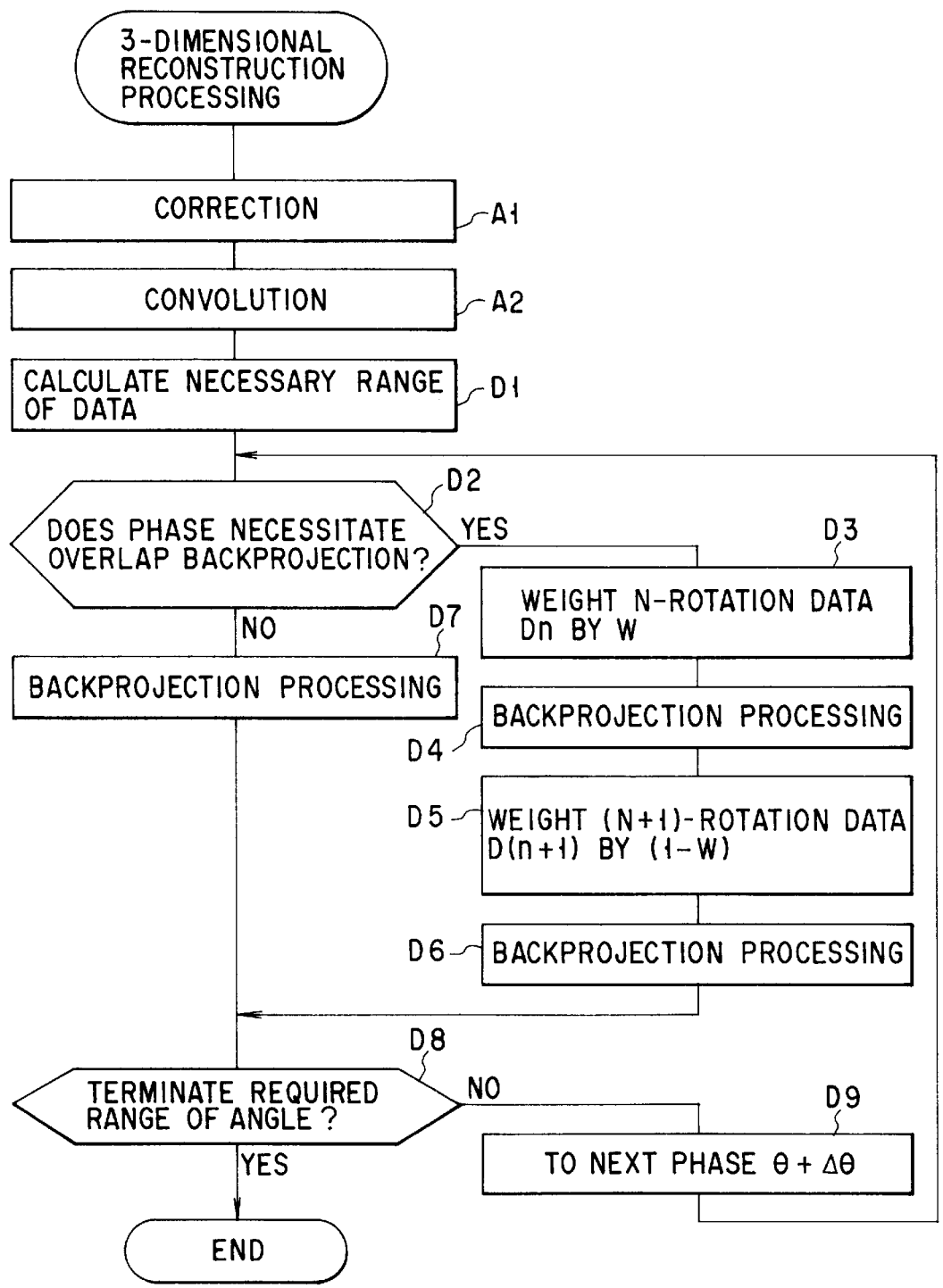
F I G. 47

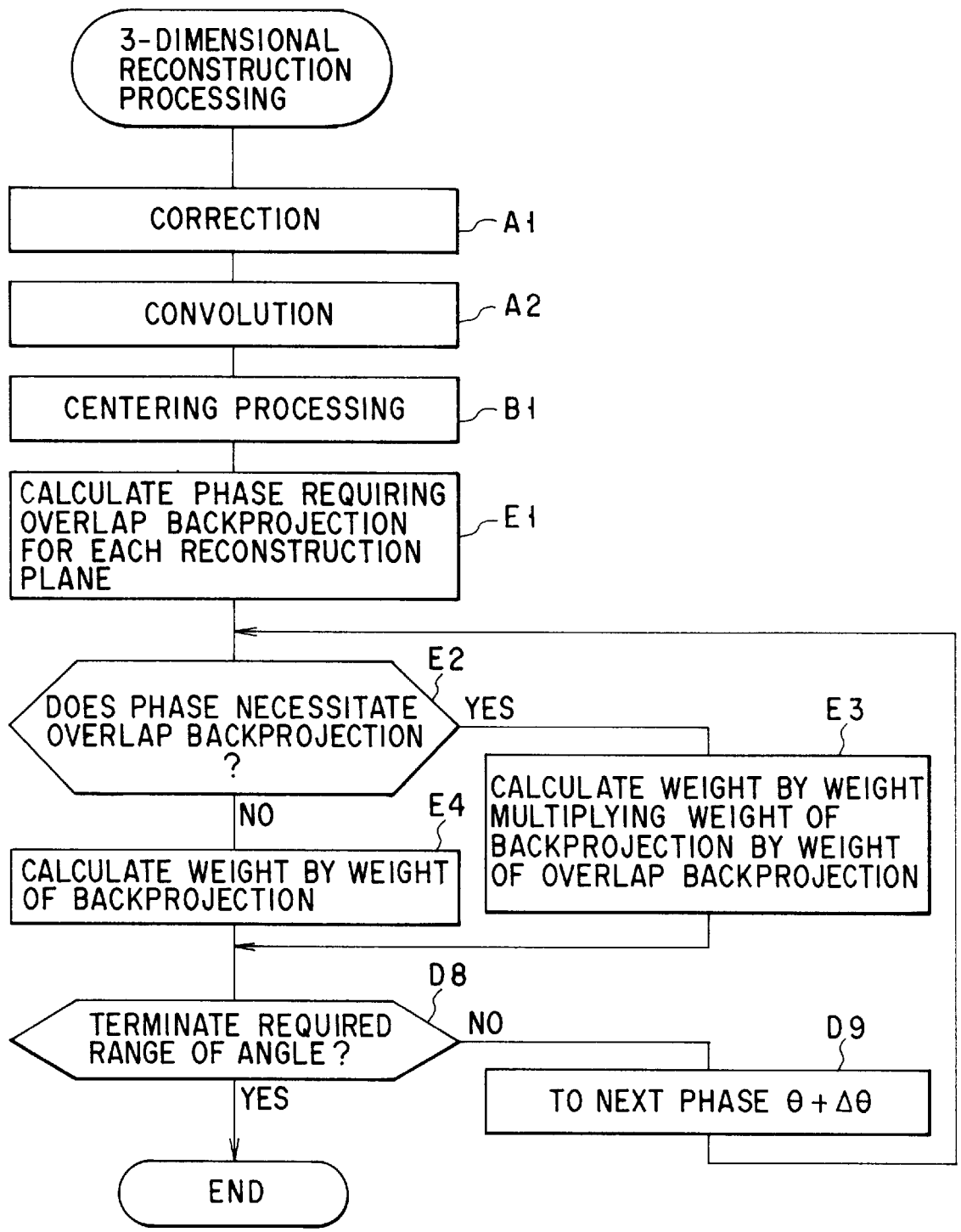
F I G. 48

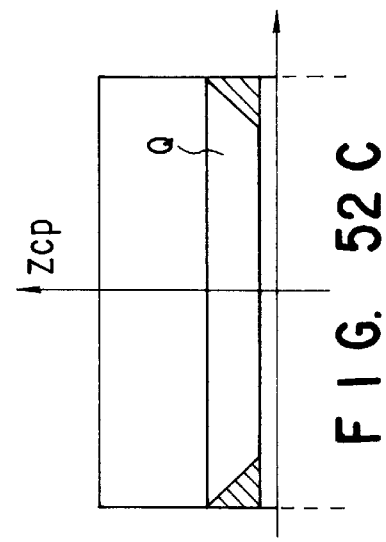
FIG. 52C
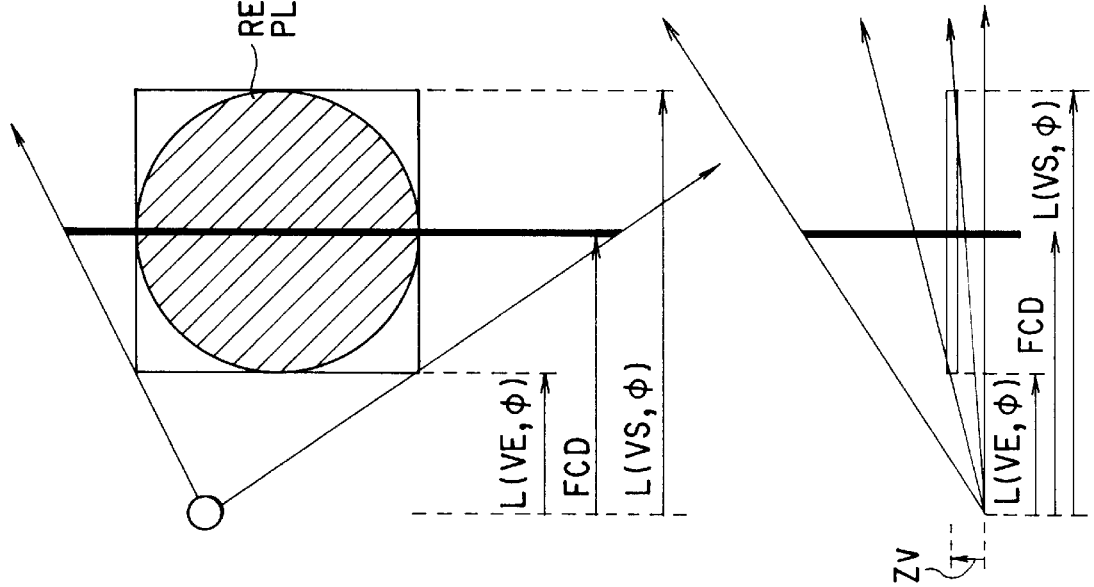
FIG. 52A
FIG. 52B

RADIATION COMPUTED TOMOGRAPHY APPARATUS

BACKGROUND OF THE INVENTION

The present invention relates to a radiation CT apparatus for irradiating a subject with radiations conically radiated from a radiation source thereof, detecting radiations allowed to penetrate the subject by a radiation detector and reconstructing the cross sectional image of the subject.

As a conventional radiation CT (Computed Tomography) apparatus, an X-ray CT apparatus, as shown in FIG. 1, uses a fan beam for irradiating X-ray beams from an X-ray source 101 thereof.

The X-ray CT apparatus is structured as follows. A subject (not shown) is irradiated with X-rays radiated from the X-ray source 101. X-rays allowed to pass through the subject are detected by an X-ray detector 102 having about 1000 channels in the form of a circular arc of a fan so that data is acquired. The X-ray source 101 and the X-ray detector 102 are rotated to collect data so that data is acquired about 1000 times (one data acquisition operation is called "one view") during one rotation. In accordance with acquired data, the X-ray cross sectional image of the subject is reconstructed. Referring to FIG. 1, FOV 103 indicates an effective field of view.

The image is reconstructed by the following image reconstruction equation (1):

$$\text{Image} = \int \text{Data-Back} \cdot d\Phi \qquad (1)$$
$$= \int \left\{ \frac{1}{F_{pixel}D^2(X)} \cdot \text{Data-}Conv \right\} d\Phi$$
$$= \int \left\{ \frac{1}{F_{pixel}D^2(X)} \cdot Conv(\text{Data-Raw}) \right\} d\Phi$$

As can be understood from equation (1), an operation for reconstructing an image by using the fan beam is required to backproject data obtained from the X-ray detector 102 by multiplying data by weight determined depending upon the positions of pixels which must be reconstructed. Therefore, a complicated process is required.

Specifically, as shown in FIG. 2, the conventional apparatus has a plurality of pixels (block points distributed densely in the form of a lattice in FIG. 2) for forming an image set with respect to the effective visual field FOV 103. Thus, data obtained at each channel of the X-ray detector 102 is weighted such that an inverse number of the square of the distance FpixelD(X) from a focal point (radiation point F of X-ray beams of the X-ray source 101)—corresponding pixel (black point) is multiplied so as to backproject data above. Referring to FIG. 2, FpixelD means "Focal-Pixel-Distance".

Although a method may be employed in which data obtained by the detector is directly backprojected, the coordinates must be converted to the polar coordinates in this case and therefore, complicated calculations must be required.

Accordingly, two types of image reconstructing methods have been developed which are adaptable to the X-ray CT apparatus using the fan beam (single slice CT apparatus).

One of the methods is called a fan-para conversion method. This method, as shown in FIG. 3, has the steps of rearranging and interpolating projection data obtained by an X-ray detector using the fan beam to produce (conversion included); and backprojecting obtained data so as to be used in the conventional X-ray CT apparatus using parallel beams.

Although the foregoing method is required to perform data conversion calculations and an interpolation process, a different weighting process for each reconstructed pixel required for the fan beam when the backprojection is performed can be omitted. Since only one data is required to be backprojected to all of pixels in the beam passage (a straight line connecting the radiation point when the parallel beams are formed and each of the channels of the X-ray detector), the process can be simplified.

Another method is a fan beam reconstruction method using a centering axis and disclosed in Japanese Patent Application KOKAI No. 55-99240.

The foregoing method, as shown in FIG. 4, has the steps of projecting (backprojecting) data obtained from the X-ray detector to a predetermined reference axis (the centering axis) running parallel to pixel columns; and projected data is again backprojected to each of the reconstructed pixel columns. Since data is first backprojected to the centering axis as described above, the weighting process which is different for each pixel can be made to be the same for each pixel column. Therefore, the process can be performed quickly and simply.

The steps of the fan beam reconstructing method using the centering axis will now be described.

(1) Projection data Data-Proj is subjected to various corrections, such as an X-ray intensity correction, and multiplication of the cos term is performed so that raw data Data-Raw is obtained. A convolution processing of Data-Raw above and the reconstruction function is performed so that Data-Conv is obtained.

(2) Data-Conv above is weighted as expressed in Equation (2) and projected to a point on a certain reference axis (the centering axis, for example, X-axis and Y-axis which are references for the pixel configuration) so that Data-Center is obtained, where FcpD(X) is the distance from the focal point to the centering axis point.

$$\text{Data-Center} = \frac{1}{F_{cp}D^2(X)} \cdot \text{Data-}Conv \qquad (2)$$

(3) The process described in (2) is repeated so that fan beam projection data of all of views are projected to the corresponding reference axis.

(4) Data-Center of a certain view projected to the reference axis is weighted for each pixel column of the image intended to be reconstructed as expressed by Equation (3) so that Data-Back is obtained. The thus-obtained projection data item Data-Back is backprojected (added to the address corresponding to the pixel of an image memory). Note that symbols A and B are shown in FIG. 4.

$$\text{Data-Back} = (A/B)^2 \cdot \text{Data-Conv} \qquad (3)$$

(5) The process described in (4) is repeated for all views so that projection data of all views are backprojected. Equation (3) is deformed with reference to FIG. 4 so that the following equation is obtained:

$$\left(\frac{A}{B}\right)^2 \cdot \text{Data-Center} = \left(\frac{F_{cp}D(X)}{F_{pixel}D(X)}\right)^2 \cdot \text{Data-Center}$$

$$= \frac{\left(\frac{F_{cp}D(X)}{F_{pixel}D(X)}\right)^2}{F_{cp}D^2(X)} \cdot \text{Data-}Conv$$

$$= \frac{1}{(F_{pixel}D(X))^2} \cdot \text{Data-}Conv$$

The obtained result coincides with the contents of the fan beam reconstruction equation, that is, the contents of the integration expressed in Equation (1).

The above-mentioned method having the structure such that backprojection to each pixel is performed after the first projection to the centering axis has been performed enables weighting Equation (1) for the backprojection, which is originally different for each pixel, to be performed with the same weighting Equation (2) for each pixel column. Therefore, the weighting calculation can be simplified and the number of calculation operations can be reduced.

Moreover, the complicated correspondence between the devices of the detector arranged on the circular arc at the same angular intervals and the pixels disposed on the straight line at the same pitch can be simplified though detailed description is omitted here.

The conventional X-ray CT apparatus using the fan beam is able to perform a quick image reconstruction processing by employing either of the two methods.

On the other hand, an X-ray CT apparatus has been developed which, as shown in FIG. 5, uses a cone beam formed by conically radiating X-ray beams from an X-ray source 201 and a two-dimensional X-ray detector 202 having detection devices (M channels×N columns) arranged on a cylindrical surface in the form as the fan beam detector columns are stacked by N columns in the direction of the Z axis so as to photograph an X-ray transillumination image.

Typical cone beam reconstruction (Feldkamp reconstruction) adapted to the X-ray CT apparatus using the cone beam has been disclosed in the following document:

"Practical cone-beam algorithm", L. A. Feldkamp, L. C. Davis, and J. W. Kress, J. Opt. Soc. Am. A/Vol. 1, No. 6, pp. 612–619/June 1984.

In the foregoing document, an approximate three-dimensional reconstruction algorithm is disclosed which can be obtained by expanding a fan beam (in a two-dimensional plane) reconstruction algorithm [Filtered-Backprojection (filter correction backprojection method)], which is a mathematically strict reconstruction method, into the direction of the Z-axis.

The cone beam reconstruction method is arranged to perform conventional scan using the cone beam and has the following steps. Note that the foregoing cone beam method uses voxels which are three-dimensional volume elements as shown in FIG. 6 in place of the pixels which are two-dimensional picture elements.

(1) Weighting of Projection Data

Projection data is multiplied by a term depending upon the Z coordinates and the cos term.

(2) Convolution Processing

The convolution processing of data obtained in the process (1) and the reconstruction function, which is the same as the fan beam, is performed.

(3) Backprojection

Data obtained in the process (1) is backprojected to the pass (from the focal point to the channel of the detector) through which the X-rays have passed. That is, the point at which the straight line backprojected from the focal point and allowed to pass through the voxel and the surface of the detector intersect is calculated. Then, data, which is backprojected, is, by interpolation or the like, produced from data of the point subjected to the process (2). Produced data is weighted with an inverse number of the square of FvoxelD (X), and then backprojected. The backprojection is performed for 360° (one revolution).

The image can be expressed by an equation similar to the fan beam reconstruction equation as follows:

$$\text{Image} = \int \text{Data-Back} \cdot d\Phi \qquad (4)$$

$$= \int \left\{ \frac{1}{F_{voxel}D^2(X)} \cdot \text{Data-}Conv \right\} d\Phi$$

$$= \int \left\{ \frac{1}{F_{voxel}D^2(X)} \cdot Conv(\text{Data-Raw}) \right\} d\Phi$$

where, FvoxelD(X)=Focus-Voxel-Distance is a distance projecting a distance between the focus and the voxel to the axial plane.

Although Equation (4), which is a three-dimensional reconstruction equation (cone beam reconstruction equation), considerably, resembles the equation concerning the fan beam reconstruction, the method of backprojecting Data-Back is considerably different as described below.

The two-dimensional fan beam reconstruction is, as shown in FIG. 7, structured such that data obtained from detectors arranged one-dimensionally is backprojected to all pixels in the reconstruction plane. On the other hand, the cone beam (Feldkamp) reconstruction is, as shown in FIG. 8, performed such that a point, at which a straight line connecting the focal point and the voxel intended to be reconstructed to each other and the surfaces of the X-ray detectors disposed two-dimensionally intersect, is obtained. Then, data obtained from the detection devices concerning the point of intersection is backprojected to all voxels located on the straight line.

When the cone beam reconstruction is performed such that a certain plane is reconstructed as is performed with the fan beam reconstruction method, data of a specific detector column and specific channel is therefore backprojected to only a portion of voxels on the reconstruction plane. Hence, detector columns and detector channels to be backprojected to each voxel must be selected. Therefore, the three-dimensional positional relationship between the straight line connecting the reconstructed voxel and the focal point to each other and the surface of the X-ray detector is an important factor.

In a case of detector columns having the same Z coordinate, the straight line connecting the device of the detector and the focal point is considered. Since voxels through which the straight lines connecting the detector columns having the same Z coordinate are allowed to pass are arranged on similar figures (for example, on the concentric circles in the case of the cylindrical detectors) of the surfaces of the detectors relative to the focal point with respect to a certain plane (reconstructed plane), calculations for obtaining the positional relationship become too complicated.

The X-ray CT apparatus employs, in addition to the conventional scanning method defined as a method in which an X-ray tube and the X-ray detector, as shown in FIG. 9A, revolve the same circular trajectory around a subject, a helical scanning method arranged as shown in FIG. 9B such that the X-ray tube and the X-ray detector are continuously revolved around the subject and the bed on which the subject is placed is moved along the axis of the body of the subject in synchronization with the revolution.

In particular, a three-dimensional reconstruction method using the Feldkamp reconstruction method adaptable to a case where the helical scanning photography using a two-dimensional array-type X-ray detector is disclosed in the following documents:

(1) "Three-Dimensional Helical Scan CT Using Cone Beam Projection", written by Hiroyuki Kudo, Tohoku University and Tsuneo Saito, Tsukuba University, DIIvol. J74-D-II, No. 8, pp. 1108–1114, August 1991, thesis magazine of Electronic Information Communication Society.

(2) "X-Ray Computer Tomographic Apparatus" disclosed in Japanese Patent Application No. 7-169963.

In Japanese Patent Application No. 7-169963, a X-ray tomographic apparatus has been disclosed which structured such that an X-ray tube for irradiating a subject with X-rays in the form of a cone beam is relatively moved on a helical trajectory when viewed from the subject, X-rays allowed to pass through the subject are detected by a two-dimensional array-type X-ray detector, and obtained projection data is backprojected so that backprojection data, to which the absorption rate of X-rays for each of a plurality a voxels defined in a photographing region is reflected, is obtained, wherein backprojection data of a specific voxel in a region in which cone beam X-ray flux from an X-ray tube at the k-th revolution and cone beam X-ray flux from the X-ray tube at the (k+1)th revolution overlap is obtained in accordance with projection data along an X-ray pass passing through the specific voxel acquired at the k-th revolution and projection data along an X-ray pass passing through the specific voxel acquired at the (k+1)th revolution so that the quality of the image is improved as compared with the conventional method in which the same is obtained in accordance with either of the projection data above.

As described above, the conventional X-ray CT apparatus having the cone beam and the two-dimensional X-ray detector involves the quantity of calculations being enlarged excessively to reconstruct an image. Thus, there arises a problem in that an excessively long time is required to complete the processing of the 3-dimensional image by using a usual computer.

As disclosed in Japanese Patent Application No. 7-169963, a fact has been detected that data Dn at the n-th revolution acquired at a certain phase and data (n+1) at the (n+1)th revolution (projection data to a specific voxel in the overlapping region) are linearly or non-linearly weighted and added so as to be backprojected (or weighted and added after the backprojection has been performed), that is, overlap backprojection is performed, so that the quality of the image is improved. A method of easily performing the above-mentioned method has been desired.

BRIEF SUMMARY OF THE INVENTION

An object of the present invention is to provide a radiation CT apparatus which is capable of shortening time required to accurately reconstruct an image photographed by using a cone beam.

Another object of the projection is to provide a radiation CT apparatus which is capable of easily practically realizing improvement in the quality of an image photographed by a helical scan method using a cone beam.

A first radiation CT apparatus according to the present invention comprises: a radiation source for irradiating a subject with radiations; detection means having at least two detector columns to detect radiations allowed to pass through the subject; means for obtaining data to be back-projected in accordance with data detected by the detection means; and image reconstruction means for reconstructing a transmitted image of the subject, wherein the image reconstructing means includes first backprojection means for backprojecting detected data to a centering plane which has been set so as to simplify the backprojection to voxels which are volume elements disposed in a three-dimensional space, and second backprojection means for backprojecting data backprojected to the centering plane to the voxels corresponding to backprojected data. The preferred manners of the first apparatus are as follows.

(1) The centering plane is formed by two-dimensional data configuration.

(2) The data lines of the centering plane are disposed in parallel to a direction in which the voxels are backprojected.

(3) The number of data lines of the centering plane is larger than the number of detected data lines.

A second radiation CT apparatus according to the present invention comprises: a radiation source for irradiating a subject with radiations; detection means having at least two detector columns to detect radiations allowed to pass through the subject; means for obtaining data to be back-projected in accordance with data detected by the detection means; and image reconstruction means for reconstructing a transmitted image of the subject, wherein the image reconstructing means includes specifying means for specifying data to be backprojected in accordance with the three-dimensional positional relationship between voxels which are volume elements disposed in a three-dimensional space and the radiation source, and backprojection means for backprojecting specified data to be backprojected to the voxels. The preferred manners of the second apparatus are as follows.

(1) The specifying means includes means which calculates a projection curve obtained by projecting the voxel lines to the detector columns in accordance with the three-dimensional positional relationship between the voxel lines and the radiation source to specify data to be backprojected.

(2) The specifying means includes a table for specifying data to be backprojected in accordance with the three-dimensional positional relationship between the voxel lines and the radiation source, and means for specifying data to be backprojected in accordance with the positional relationship and the table.

A third radiation CT apparatus according to the present invention comprises: a radiation source for irradiating a subject with radiations; detection means having at least two detector columns to detect radiations allowed to pass through the subject; means for obtaining data to be back-projected in accordance with data detected by the detection means; and image reconstruction means for reconstructing a transmitted image of the subject, wherein the image reconstructing means includes means which performs a bundling process in a direction perpendicular to the detector columns in accordance with a plurality of detected data items and which performs backprojection to voxels which are disposed three-dimensionally in a space in accordance with data subjected to the bundling process so as to reconstruct a sectional image of the subject. With this configuration, it is preferred the image reconstruction means includes first backprojection means for backprojecting detection data obtained by the detection means to a centering plane previously set to simplify the backprojection to the voxels, and second backprojection means for backprojecting data backprojected to the centering plane to the corresponding voxels, and the first backprojection means bundles detection data in a column direction to backproject bundled detection data to the voxels when the backprojection is performed.

A fourth radiation CT apparatus according to the present invention comprises: a radiation source for irradiating a subject with radiations; detection means having at least two detector columns to detect radiations allowed to pass through the subject; interpolation means for performing an interpolation process in a column direction of detected data to raise the sampling density of detection data detected by the detection means; and image reconstruction means for reconstructing a transmitted image of the subject.

A fifth radiation CT apparatus according to the present invention comprises: a radiation source for irradiating a subject with radiations; detection means having at least two detector columns to detect radiations allowed to pass through the subject; overlap weighting means which obtains a phase which must be weighted by an overlap process and which weights convolution data among data obtained from the detection means by convolution at the N-th revolution and the (N+1)th revolution corresponding the phase which must be subjected to the overlap process for the purpose of performing the overlap-backprojection; backprojection means for backprojecting data weighted by the overlap weighting means in a phase which must be subjected to the overlap process and, as it is, backprojecting data obtained by convolution in a phase which is not required to be subjected to the overlap process, and image reconstruction means for reconstructing a transmitted image of the subject.

In a fourth and fifth radiation CT apparatus according to the present invention, the image reconstruction means includes first backprojection means for backprojecting convoluted and weighted data to the centering plane; and second backprojection means for backprojecting data backprojected to the centering plane to the voxels corresponding to the data.

A sixth radiation CT apparatus according to the present invention comprises: a radiation source for irradiating a subject with radiations; detection means having at least two detector columns to detect radiations allowed to pass through the subject; first backprojection means for backprojecting detection data obtained by the detection means to a centering plane set previously; overlap weighting means which obtains a phase which must be weighted by an overlap process and which weights centering data among centering data backprojected by the first backprojection means corresponding to the phase which must be subjected to the overlap process for the purpose of performing the overlap-backprojection; backprojection means for backprojecting data weighted by the overlap weighting means in a phase which must be subjected to the overlap process and, as it is, backprojecting centering data obtained by the first backprojection means in a phase which is not required to be subjected to the overlap process, and image reconstruction means for reconstructing a transmitted image of the subject.

A seventh radiation CT apparatus according to the present invention comprises: a radiation source for irradiating a subject with radiations; detection means having at least two detector columns to detect radiations allowed to pass through the subject; means for obtaining data to be backprojected in accordance with detection data detected by the detection means, and image reconstruction means for reconstructing a transmitted image of the subject, wherein the image reconstruction means includes first backprojection means for backprojecting detection data obtained by the detection means to the centering plane, and second backprojection means for backprojecting data backprojected to the centering plane to corresponding voxels, and the second backprojection means calculates a projection curve obtained by projecting each voxel line of a first image to the centering plane, backprojects data of the centering plane to the voxels corresponding to the first image in accordance with a result of the calculation, and uses, for images ensuing a second image, the result of the calculation of the projection curve of the first image in backprojection of images ensuing the second image to the voxels corresponding to the first image. With this configuration, it is preferred that the first backprojection means weight data from the second line to a line right before the final line.

An eighth radiation CT apparatus according to the present invention comprises: a radiation source for irradiating a subject with radiations; detection means having at least two detector columns to detect radiations allowed to pass through the subject; means for obtaining data to be backprojected in accordance with detection data detected by the detection means, and image reconstruction means for reconstructing a transmitted image of the subject, wherein the image reconstruction means includes first backprojection means for backprojecting detection data obtained by the detection means to the centering plane, and second backprojection means for backprojecting data backprojected to the centering plane to voxels corresponding to the data, and the first backprojection means calculates a projection point of a first line of the centering plane to the detection means, calculates data in the first line of the centering plane in accordance with a result of the calculation, and uses a result of the calculation of the first line to data of a second and ensuing lines corresponding to the first line to calculate data of the second and ensuing lines.

A ninth radiation CT apparatus according to the present invention comprises: a radiation source for irradiating a subject with radiations; detection means having at least two detector columns to detect radiations allowed to pass through the subject; means for obtaining data to be backprojected in accordance with detection data detected by the detection means; and image reconstruction means for reconstructing a transmitted image of the subject, wherein the image reconstruction means includes first backprojection means for backprojecting detection data obtained by the detection means to a centering plane, and second backprojection means for backprojecting data backprojected to the centering plane to voxels corresponding to the data, and the first backprojection means calculates a required centering range to backproject the detection data to a predetermined centering plane in accordance with the centering range.

A tenth radiation CT apparatus according to the present invention comprises: a radiation source for irradiating a subject with radiations; detection means having at least two detector columns to detect radiations allowed to pass through the subject; means for obtaining data to be backprojected in accordance with detection data detected by the detection means; and image reconstruction means for reconstructing a transmitted image of the subject, wherein the image reconstruction means includes first backprojection means for backprojecting detection data obtained by the detection means to a centering plane, and second backprojection means for backprojecting data backprojected to the centering plane to voxels corresponding to the data, and the first backprojection means calculates a projection point function for obtaining a point of projection of the centering point of the centering plane to the detector surface, performs fitting the calculated projection point function with a predetermined function, and backprojects the fitted projection point function to the centering plane by an equation developed by a derived function of the projection point function.

According to the radiation CT apparatus according to the present invention, the detection means has any one of a cylindrical shape, a flat shape and a polyhedral shape.

According to the radiation CT apparatus according to the present invention, time required to accurately reconstruct an image photographed by using a cone beam can be shortened.

According to the radiation CT apparatus according to the present invention, improvement in the quality of an image photographed by a helical scan method using a cone beam can easily be realized.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 is a diagram showing the structure of a fan beam and an FOV of a conventional X-ray CT apparatus;

FIG. 2 is a diagram for explaining pixels for the conventional X-ray CT apparatus;

FIG. 3 is a diagram for explaining a fan-para conversion method adapted to the conventional X-ray CT apparatus;

FIG. 4 is a diagram for explaining a fan beam reconstruction method adapted to the conventional X-ray CT apparatus and using a centering axis;

FIGS. 9A and 9B are diagrams showing a scanning method adapted to the X-ray CT apparatus;

FIG. 10 is a diagram showing the shape of an X-ray CT apparatus according to a first embodiment of the present invention;

FIGS. 16A to 16D are diagrams showing projection curve of the voxel lines to the detector surface in the reconstruction section of the X-ray CT apparatus according to the embodiment;

FIG. 17 is a diagram showing a centering plane showing the voxel line, centering plane, the detector surface, their variables, ends and center point;

FIGS. 18A to 18C are graphs showing a projection curve of the voxel line to the detector surface, the voxel line, and a projection curve of the voxel line to the centering plane in the reconstruction section of the X-ray CT apparatus according to the embodiment;

FIG. 19 is a diagram showing the voxel line and the centering plane of the reconstruction section of the X-ray CT apparatus according to the embodiment;

FIG. 24 is a diagram showing a flat-type X-ray detector serving as another example of the X-ray detector for use in the X-ray CT apparatus according to the embodiment;

FIG. 25 is a diagram showing the positional relationship between a voxel line and the flat type X-ray detector of the X-ray CT apparatus using the flat-type X-ray detector shown in FIG. 24;

FIG. 26 is a graph showing a projection curve of the voxel line to the detector surface in a case where the flat-type X-ray detector shown in FIG. 24 is used;

FIG. 27 is a graph showing a projection curve of the voxel line to the centering plane in the X-ray CT apparatus using the flat-type X-ray detector shown in FIG. 24;

FIG. 28 is a diagram showing a trihedral X-ray detector serving as another example of the X-ray detector for use in the X-ray CT apparatus according to the embodiment;

FIG. 29 is a graph showing a projection curve of the voxel line to the detector surface in the case where the detector shown in FIG. 28 is used;

FIG. 30 is a diagram showing a one-time interpolation in backprojection of detector column to the voxels;

FIG. 31 is a diagram showing a two-time interpolation in backprojection of detector column to the voxels;

FIG. 32 is a diagram showing a first interpolation method in the backprojection of the detector column to the voxels in the reconstruction section of the X-ray CT apparatus according to the embodiment;

FIG. 33 is a diagram showing a second interpolation method in the backprojection of the detector column to the voxels in the reconstruction section of the X-ray CT apparatus according to the embodiment;

FIG. 38 is a block diagram showing an essential structure of a reconstruction section 12 according to the present invention in a case where the centering process is not performed;

FIG. 39 is a diagram showing bundling centering line in the reconstruction section of the X-ray CT apparatus according to the embodiment;

FIG. 42 is a diagram showing the relationship between the cone beam and five slice images A to Equation at a certain phase θ in the X-ray CT apparatus according to the second embodiment;

FIG. 43 is a diagram showing projection curve (a straight line) of each of slice images A to Equation when backprojection from voxel Va to voxel Vb is performed in the X-ray CT apparatus according to the second embodiment;

FIG. 44 is a flow chart of the three-dimensional reconstruction processing using a result of calculation of reconstruction of a first image to reconstruct another image in the reconstruction section of the X-ray CT apparatus according to the embodiment;

FIG. 45 is a diagram showing the centering plane and an image to be reconstructed in an X-ray CT apparatus according to a third embodiment of the present invention;

FIG. 46 is a diagram showing overlap-backprojection in the reconstruction section of an X-ray CT apparatus according to a fourth embodiment of the present invention;

FIG. 47 is a flow chart of a three-dimensional reconstruction processing as a first example of the overlap-backprojection in the reconstruction. section of the X-ray CT apparatus according to the embodiment;

FIG. 48 is a flow chart of a three-dimensional reconstruction processing as a second example of the overlap-backprojection in the reconstruction section of the X-ray CT apparatus according to the embodiment;

FIGS. 52A to 52C are diagrams showing limitation of a range of the centering plane in the reconstruction section of the X-ray CT apparatus according to the embodiment;

DETAILED DESCRIPTION OF THE INVENTION

A first embodiment of the present invention will now be described with reference to the drawings.

Figure 11:
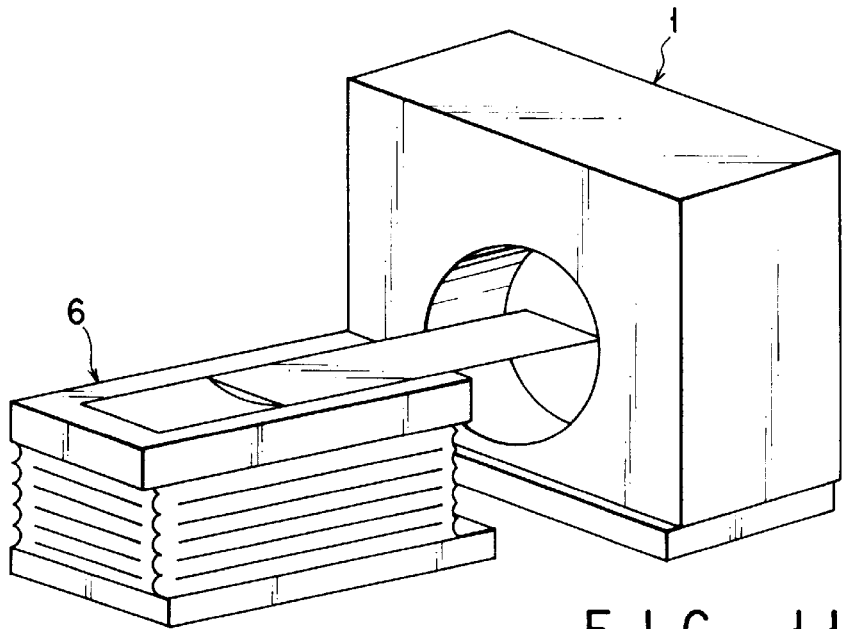
FIG. 11 is a diagram showing the shape of a gantry of the X-ray CT apparatus according to the embodiment.

FIG. 10 is a diagram showing the structure of an X-ray CT apparatus according to the first embodiment of the present invention. FIG. 11 is a view showing a gantry.

A gantry 1 serving as a projection data measuring system accommodates an X-ray source 3 for generating an X-ray flux formed into a substantially conical shape; and an X-ray detector 5 of a two-dimensional array type having a plurality of detection devices disposed two-dimensionally. The X-ray source 3 is mounted on a rotating ring 2 in a state where the X-ray source 3 faces an X-ray detector 5 while interposing a subject placed on a bed.

Figure 5:
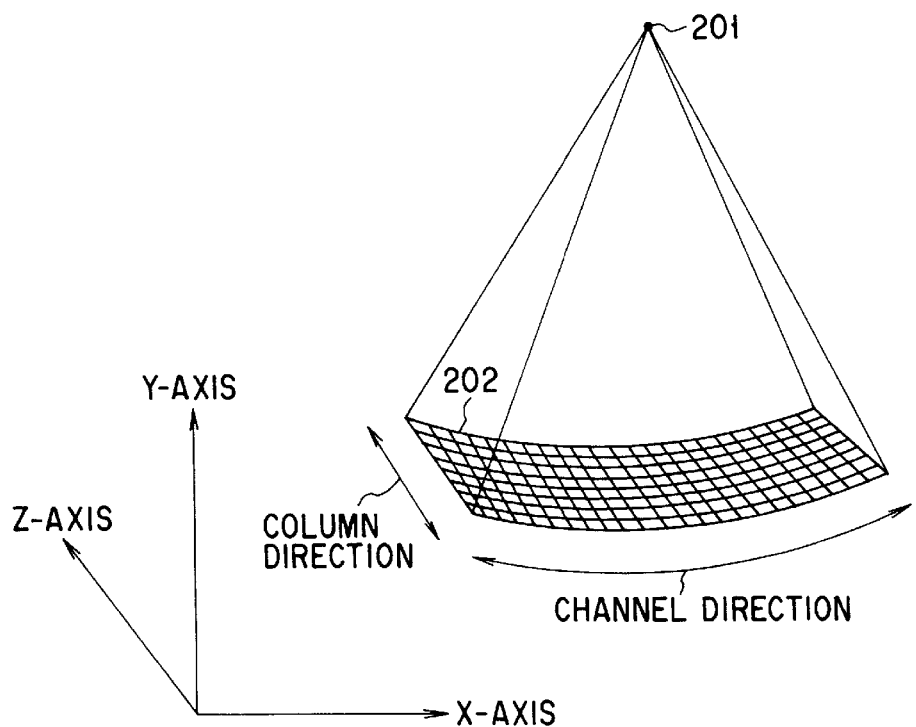
FIG. 5 is a diagram showing the cone beam for the conventional X-ray CT apparatus.

The X-ray detector 5 is, as shown in FIG. 5, formed by stacking a plurality of columns (e.g., ten columns) of one-dimensional array-type detectors in each of which a plurality of (e.g., 1000 channels) detection devices are arranged one-dimensionally for generating a fan beam, the X-ray detector 5 being mounted on a rotating ring 2. It is assumed is that one detection device corresponds to one channel.

X-rays from the X-ray source 3 are, through an X-ray filter 4, irradiated to a subject. The X-rays allowed to pass through the subject are detected as an electric signal by the X-ray detector 5.

An X-ray controller 8 supplies a trigger signal to a high-voltage generator 7. The high-voltage generator 7 applies high voltage to the X-ray source 3 at the timing at which it receives the trigger signal. As a result, X-rays are emitted from the X-ray source 3.

A gantry controller 9 controls the rotational speed of the rotating ring 2 of the gantry 1 and the bed 6 while synchronizing the rotational speed and the slide speed with each other. A system controller 10 serving as a central control section controls the X-ray controller 8 and the gantry controller 9 to perform various scanning operations, such as a so-called helical scanning operation in which the X-ray source 3 is moved on a helical trajectory when viewed from the subject.

For example, when the helical scanning operation is performed, the rotating ring 2 is continuously rotated at a predetermined angular velocity. Moreover, while moving the bed 6 at a predetermined speed, X-rays are emitted from the X-ray source 3 continuously or intermittently for each predetermined angle.

An output signal from the X-ray detector 5 is, for each channel, amplified by a data acquisition section 11, and then converted into a digital signal. A projection data transmitted from the data acquisition section 11 is fetched by a reconstruction section 12.

The reconstruction section 12 obtains backprojection data, to which the absorption ratio is reflected, for each voxel in accordance with the projection data.

Figure 6:
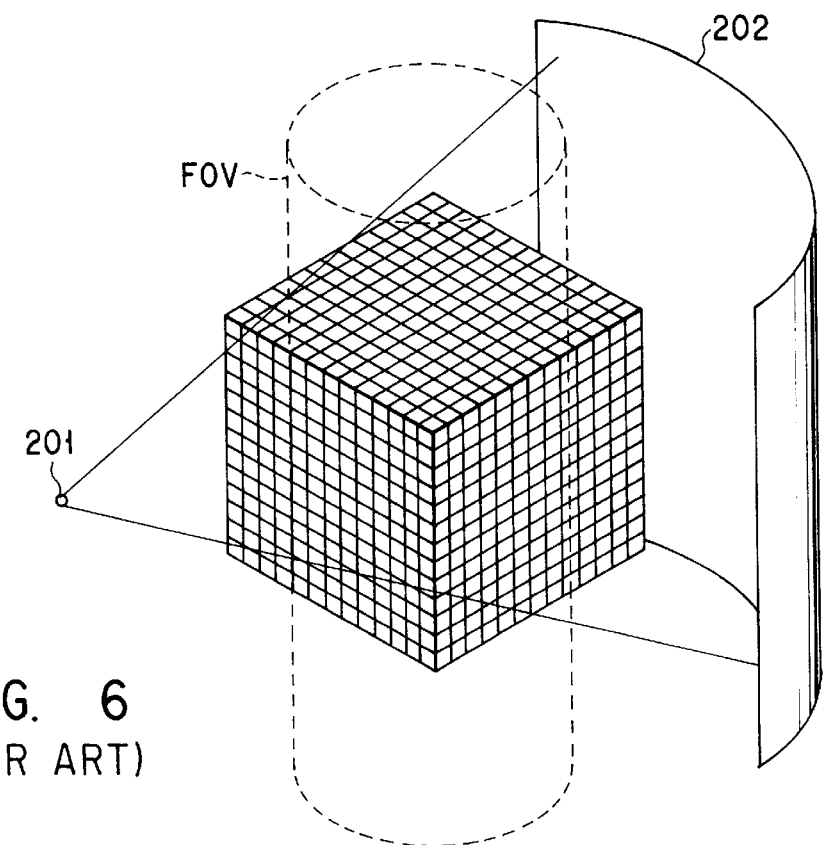
FIG. 6 is a diagram for explaining voxels with respect to the cone beam for the conventional X-ray CT apparatus.
Figure 7:
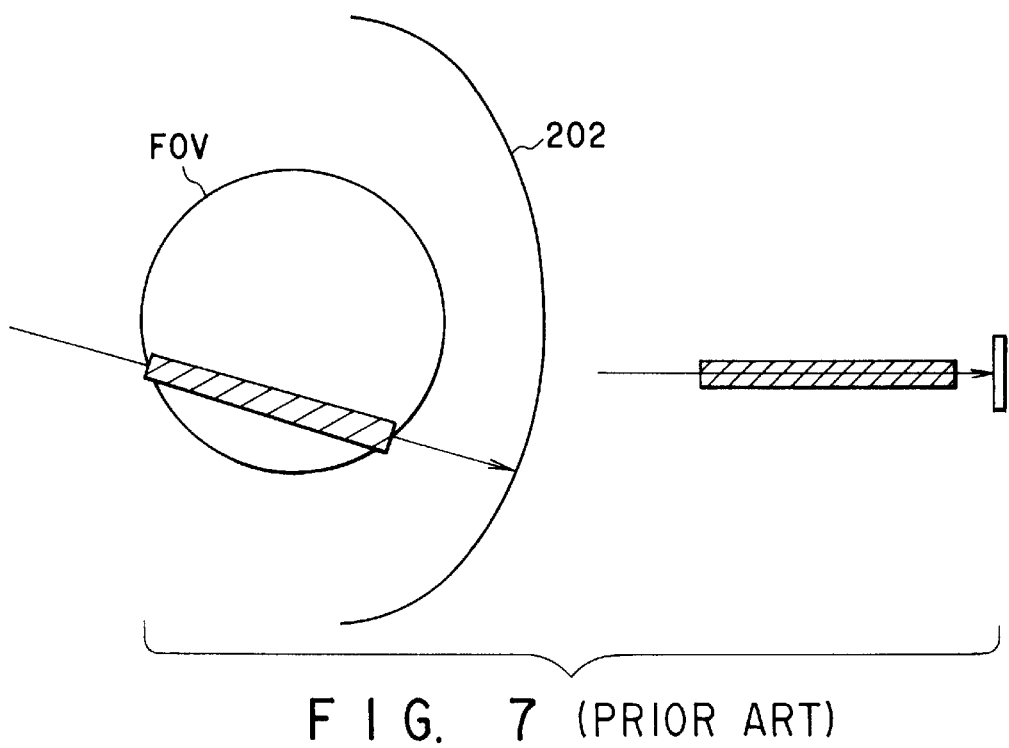
FIG. 7 is a diagram for explaining backprojection of detector data to pixels in the conventional X-ray CT apparatus using the fan beam.
Figure 8:
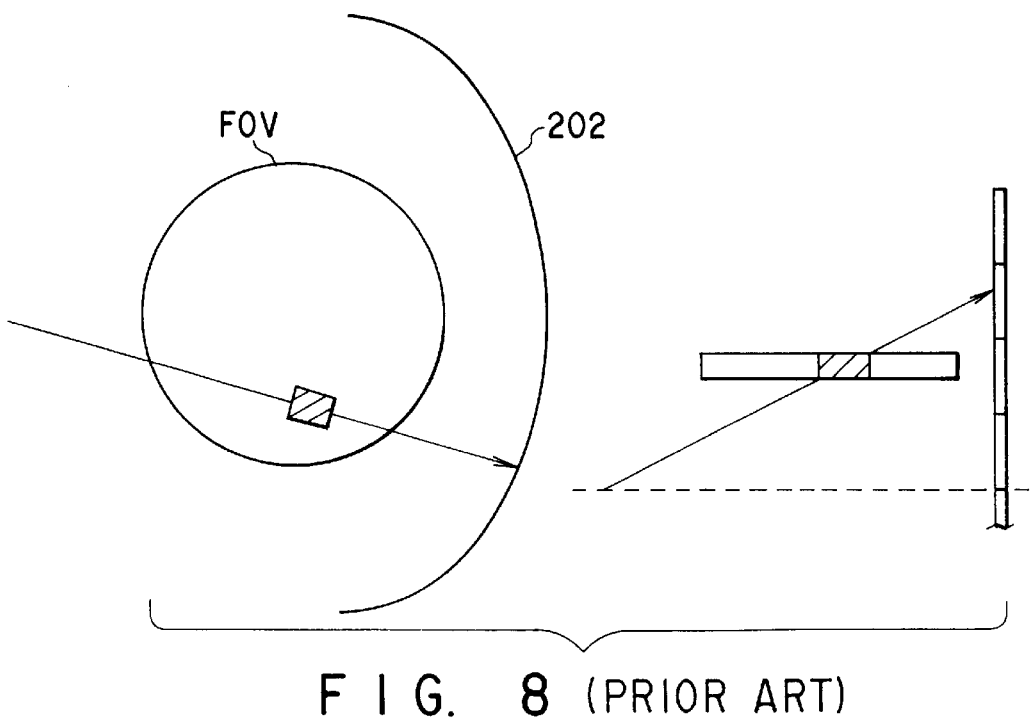
FIG. 8 is a diagram for explaining backprojection of detector data to voxels in the conventional X-ray CT apparatus using the fan beam.

An effective visual field (FOV which is a photographing region) for a helical scanning operation type X-ray CT apparatus is formed into a cylindrical shape relative to the central axis of the rotation of the helical scan. The reconstruction section 12 defines a plurality of voxels (volume elements disposed three-dimensionally) in the effective visual field (see FIG. 6) so as to obtain backprojection data for each voxel from projection data supplied from the X-ray detector 5. Three-dimensional image data produced in accordance with the backprojection data or tomographic image data is supplied to a display device 14 so as to be visually displayed as a three-dimensional image or a tomographic image.

Figure 12A:
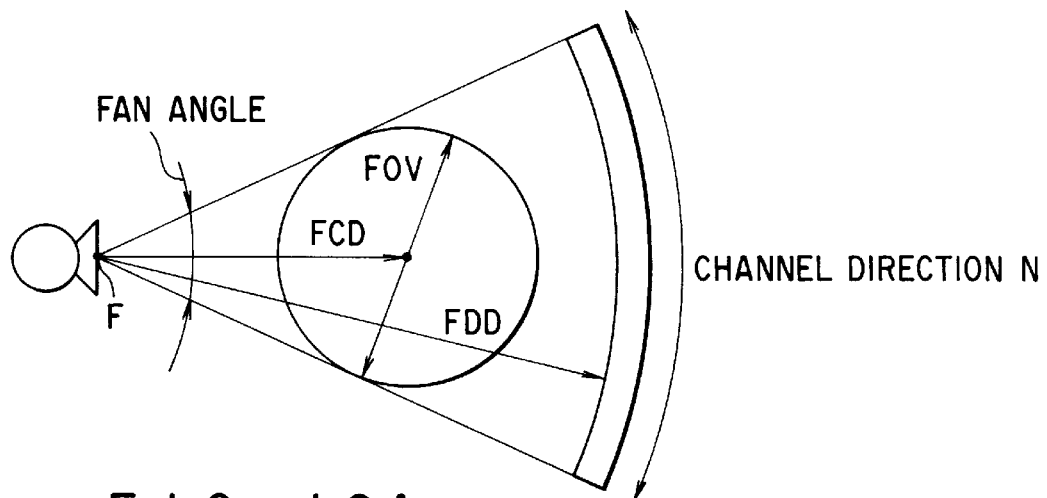
FIGS. 12A and 12B are diagrams showing the geometry of the X-ray CT apparatus according to the embodiment.
Figure 12B:
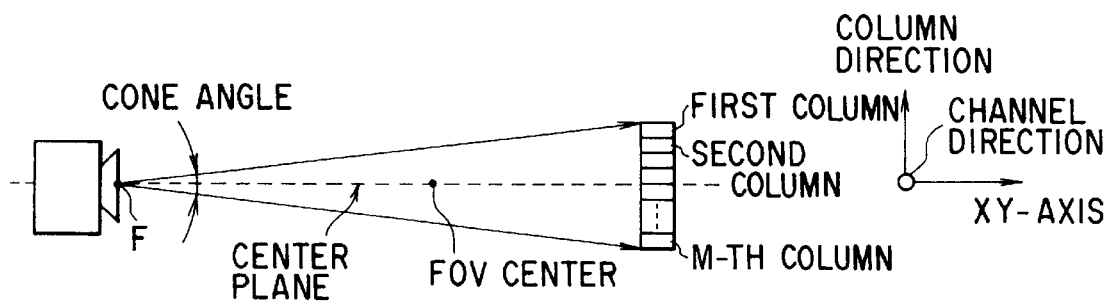

As shown in FIGS. 12A and 12B, the geometry of the X-ray CT apparatus according to this embodiment is as follows:

Number of Detector Columns: M=20

Height of Each Column in the Direction of the Z axis: Dseg=2 mm

Thickness of X-ray Detector: M×Dseg=40 mm

Number of Channels: N=1000

Distance from Focal Point to Rotation Center: FCD (Focus-center-Distance)=600 mm Distance from Focal Point to Detector: FDD (Focus-Detector-Distance)=1200 mm Effective Visual Field: FOV (Field of View)=500 mm Angle of Effective Visual Field (Angle of Fan): θ=50°

Figure 13:
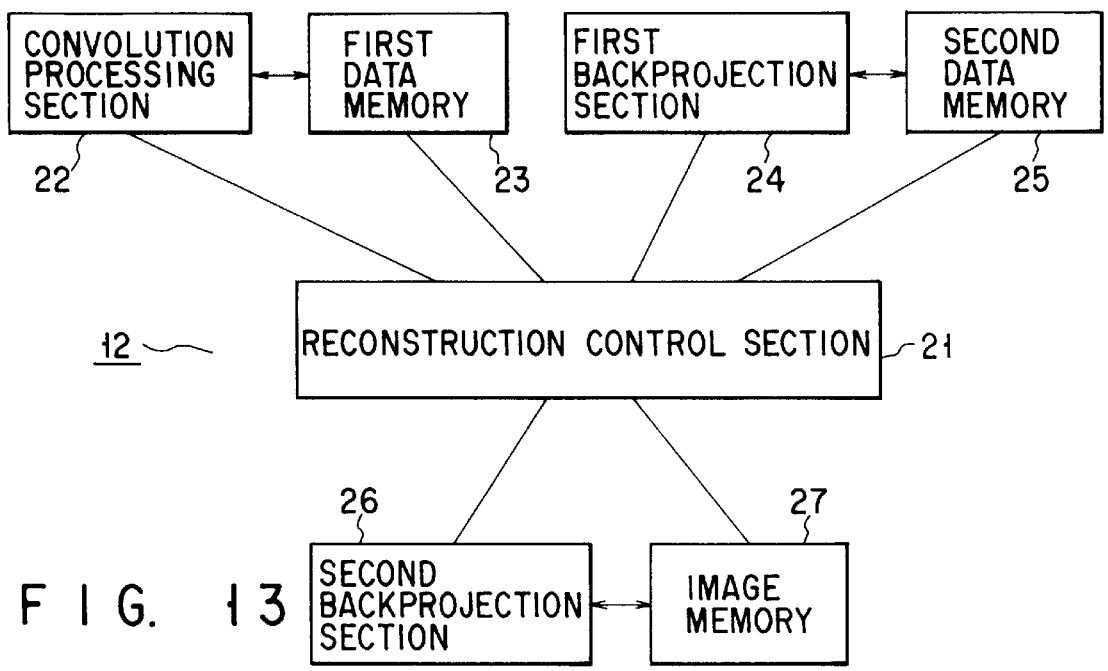
FIG. 13 is a block diagram showing the essential portion of the structure of a reconstruction section of the X-ray CT apparatus according to the embodiment.

FIG. 13 is a block diagram showing an essential structure of the reconstruction section 12.

A reconstruction control section 21 controls overall calculations and three-dimensional reconstruction processings including data selection, weighting, centering process and backprojection required to perform the convolution processing and the backprojection processing.

A convolution processing section 22 subjects projection data acquired by the data acquisition section 11 to the convolution processing. Convolution data obtained from the convolution processing is stored in a first memory 23.

A first backprojection section 24 subjects convolution data stored in the first memory 23 to a backprojection (projection) process to a predetermined centering plane. The backprojected centering data is stored in a second data memory 25.

A second backprojection section 26 backprojects (three-dimensional backprojects) centering data stored in the second data memory 25 to the voxel. Backprojected reconstruction data (an image) is stored in an image memory 27.

A plurality of factors for the three-dimensional reconstruction using the cone beam will now be considered.

Then, conversion of coordinates of a reconstruction voxel column (a straight line), a centering plane (a plane), a detector column (a circular arc), a detector surface (a cylinder, however, a plane when developed on a data memory) will now be described.

Initially, the reconstruction voxel column, the surface of the detector and the centering plane will now be described.

Figure 14:
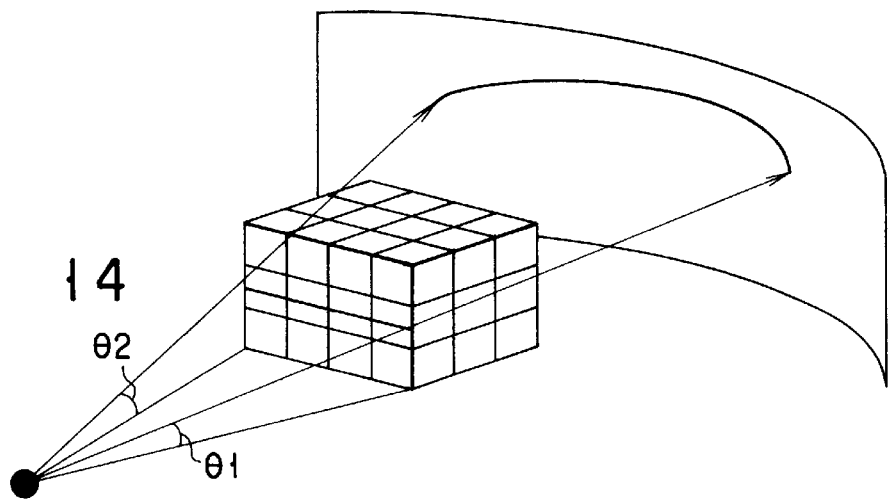
FIG. 14 is a diagram showing projection of a voxel line to the detector surface in the reconstruction section of the X-ray CT apparatus according to the embodiment.
Figure 15:
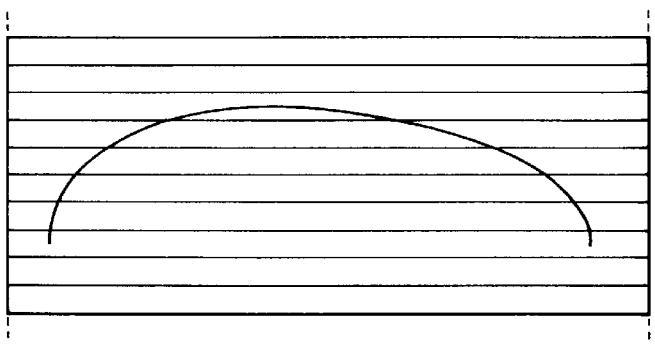
FIG. 15 is a graph showing a projection curve of the voxel line to the detector surface in the reconstruction section of the X-ray CT apparatus according to the embodiment.

As discussed below, projection to the detector surface of the voxel column (a straight line) in one column as shown in FIG. 14 is formed into a curved line as shown in FIG. 15.

Diagrams of the reconstruction voxel column, the detector surface and the centering plane observed from the direction of the Z axis (a direction perpendicular to X-Y plane) are shown in FIG. 16A. The channels (detector columns) of X-ray detector 5 are disposed on a circular arc while being apart from one another by the same angles when viewed from focal point F. In FIG. 16A, the rotational angle of the focal point rotation (view) is indicated by $\phi$ and the angle in the direction of the channel is indicated by $\theta$.

At the above-mentioned focal point, the centering plane is located on the X-axis (that is, included in the X-axis and Z-axis plane) and the X-axis coincides with Xcp axis, which is the X-axis of the centering plane. Note that the coordinates of the reconstruction voxel column are defined to be $(Xv, Yv)$ . . . (although Xv is changed together with the voxel, Yv is constant).

Assumptions are made as shown in FIG. 16B that the length of segment FC (distance from the focal point to the center of rotation) is FCD, the length in a case that segment FV0 is projected to XY plane (solid line of FIG. 16A) when an arbitrary voxel V0 is considered is FCD', length of segment FV projected to XY plane (on a dashed line shown in FIG. 16A) is FCD" when a certain voxel V is considered, and the distance from the focal point to the detector is FDD. Another assumption is made that the coordinates on a developed surface of the detector is indicated by an axis of abscissa (Xdet=θ FDD) and axis of ordinate (Zdet).

Initially, projection of a reconstruction voxel column on the detector surface will be considered. Note that Xxp indicates the X-rays coordinate of the segment FV on the centering plane and is obtained by the following Equation (5):

$$FCD \cdot \sin\theta = Xcp \cdot \sin\left(\frac{\pi}{2} - (\phi + \theta)\right) \quad (5)$$

$$Xcp = FCD \cdot \frac{\sin\theta}{\cos(\phi + \theta)}$$

Since ΔFCXcp and ΔFVoXv are similar, the following Relation Equation (6) is used $$Xcp = FCD' \cdot \frac{\sin\theta}{\cos(\phi + \theta)} \quad (6)$$

$$FCD' = FCD + \frac{Yv}{\cos\phi}$$

$$\theta = \tan^{-1}\left(\frac{Xv \cdot \cos\phi}{FCD' - Xv \cdot \sin\phi}\right) \quad (7)$$

Foregoing Equation (7) is an equation expressing the direction of the channels when conversion from Xv to θ is performed, that is, projection of the reconstruction voxel column to the detector surface is performed.

As can be seen from Equation (7), projection of the reconstruction voxel column to the detector surface results in a non-linear configuration. Therefore, in FIG. 18C, the distance (large) when the left-hand voxels, for example, a first voxel and a second voxel, are projected on the detector surface and the distance (small) from a right-hand voxel, for example, the 511th voxel to the 512th voxel are different from each other and are non-linear configuration depending upon the angle θ.

The relationship between the segment FXcp and the segment FCD is as follows:

$$FXcp \cdot \cos(\phi+\theta) = FCD \cdot \cos\phi \quad (8)$$

Therefore, the following relationship is obtained.

$$FCD'' = FXcp + XcpV \quad (9)$$
$$= \frac{\cos\phi}{\cos(\phi+\theta)} \cdot FCD + \frac{Yv}{\cos(\phi+\theta)}$$

Thus, the equation expressing the column direction of the reconstruction voxel column to the detector surface is as follows:

$$Zdet = \frac{FDD}{FCD''} \cdot Zv \quad (10)$$
$$= \frac{\cos(\phi+\theta) \cdot FDD}{(\cos\phi \cdot FCD + Yv)} \cdot Zv$$

As can be understood from the Equation (10), projection of a straight line reconstruction voxel column having fixed Z coordinate onto the detector surface results in a non-linear curve as shown in FIG. 16D depending upon the angle q. However, the Z coordinate Zv of the reconstruction voxel column and the coordinates of the Zdet axis have a proportional relationship.

The foregoing fact is shown in FIGS. 17 and 18A to 18C. FIG. 17 is a diagram showing voxel column V, centering plane Channel, detector surface D, their variables, positions of the end points and the central points. FIG. 19 is a diagram showing the relationship between the voxel column Voxel and the centering plane C, wherein the centering plane Channel runs parallel to the voxel column V.

Projection of the voxel column in the form of a straight line shown in FIG. 18A to the centering plane results in a straight line as shown in FIG. 18B. The pitch of the voxels and the points on the centering plane hold a predetermined ratio and, therefore, no distortion is generated. That is, if data, which must be backprojected, is on the straight line and disposed at the same pitch on the centering plane, backprojection to the voxel, of course, results in the straight line and the same pitch. That is, the relationship between the voxel and the centering plane is made to be a simple enlargement and contraction relationship.

If the voxel column is projected to the detector surface, non-linear distortion is generated in both the channel direction and the column direction, as shown in FIG. 18C. As can be understood from projection of two voxel columns having different Z coordinates Zv (one of the voxel columns is shown in a solid line and another voxel column is shown in a broken line), the projection images of the two voxel columns on the detector surface has the foregoing enlargement and contraction relationship.

In consideration of the foregoing facts, the simplest reconstruction method of a cone beam will now be described.

(1) Projection data supplied from the X-ray detector is subjected to a correction process, including correction of the intensity of X-rays, and then subjected to a Feldkamp weighting process. A result of the process is stored in the data memory.

(2) projection data stored in the data memory is, together with the reconstruction function, subjected to a convolution processing. A result of the process is stored in a second data memory.

(3) A projection curve formed by projecting the voxel column on the detector surface is calculated in accordance with the Equations (7) and (10). Then, data to be backprojected is selected so that the address of data above is generated.

(4) Subject data is read, and then weighted as determined previously. Then, the weighted data is added to the position of the subject voxel in the image memory.

Figure 20:
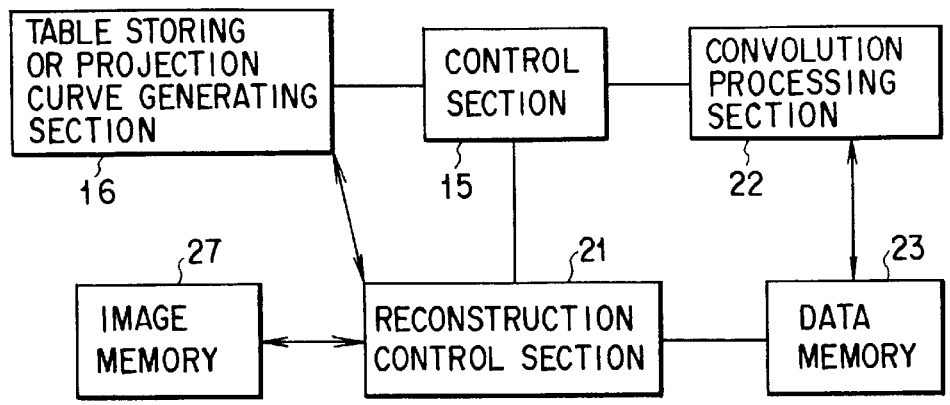
FIG. 20 shows an arrangement for achieving "direct backprojection method" or "table method".

The above-mentioned method is called a "direct backprojection method". The process in (3) may be performed such that the projection curve is previously calculated and stored in a data memory or the like in the form of a table. The above-mentioned method is called a "table method". An arrangement for achieving "direct backprojection method" or "table method" is shown in FIG. 20.

With either of the foregoing methods, the projection curve may be an approximation curve. However, the direct backprojection method involves data selection calculations in the column direction being added to the calculation of data selection, which must be performed also in the two-dimensional backprojection (in the channel direction) of fan beam projection data, and weighting calculations. Therefore, an extremely large quantity of calculations must be performed. In the case of the table method, a memory for storing the large table is required.

Accordingly, the first embodiment of the present invention is arranged to backprojection data (projection data) obtained from the X-ray detector 5 to be backprojected to the centering plane, and then the backprojected data is backprojected to each voxel.

Then, a case where the pitch on the detector surface (or on the data memory) and straight line are projected to the centering plane will now be considered.

Similarly to equation (10') equation (10') is defined as follows. Then, equation (8') which is a modification of equation (8) is substituted into equation (10'), and equation (11) is obtained.

$$FXcp = \frac{\cos\phi \times FCD}{\cos(\phi+\theta)} \quad (8')$$

$$Zcp = \frac{FXcp}{FDD} \cdot Zdet \quad (10')$$

$$= FCD \cdot \frac{\cos\phi}{FDD \cdot \cos(\phi+\theta)} \cdot Zdet \quad (11)$$

In a case where the straight line on the centering plane is projection data onto the detector surface, it is expressed by the following Equations (7') and (11'):

$$\theta = \tan^{-1}\left(\frac{Xcp \cdot \cos\phi}{FCD - Xcp \cdot \sin\phi}\right) \quad (7')$$

$$Zdet = \frac{FDD}{FXcp} \cdot Zcp \quad (11')$$

Therefore, a nonlinear distortion is a distortion in accordance with equations (5) and (11) in case of a projection from the detector column to the centering plane or equations (7') and (11') in case of a projection from a line of the centering plane to the detector column.

Figure 21A:
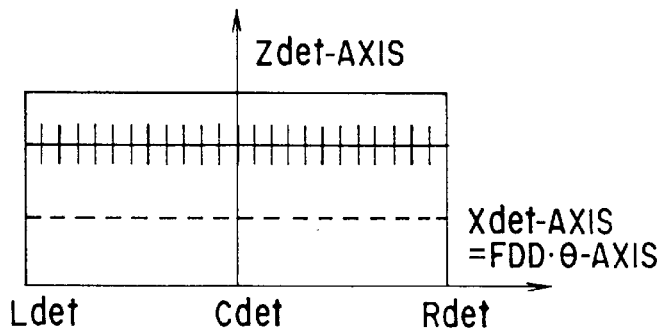
FIGS. 21A to 21C are graphs showing a projection curve of the detector column to the voxels, the detector column and a projection curve of the detector column to the centering plane in the reconstruction section of the X-ray CT apparatus according to the embodiment.
Figure 21B:
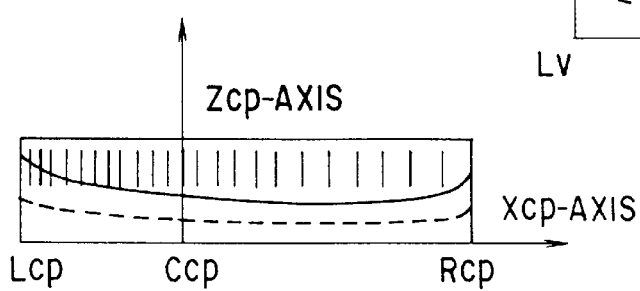
Figure 21C:
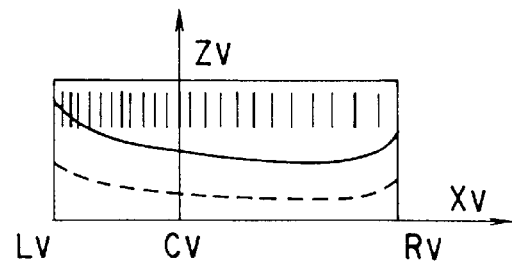

The foregoing fact is shown in FIGS. 21A to 21C. When data of all of the channels of the detector column expressed by a straight line shown in FIG. 21A is projected to the centering plane, distortion in both Xcp and Zcp directions is generated in accordance with the non-linear Equations (5) and (11), as shown in FIG. 21B.

Each of the distortion in the direction Z and the same pitch distortion of the configuration in the direction X is opposite to that shown in FIGS. 18A to 18C. Although no distortion is generated between the centering plane and the reconstruction voxel column as described above, projection of data of all of the channels of the detector column to the voxels results in similar distortion being generated, as shown in FIG. 21C. That is, distortion of the projection to the centering plane in the direction Z, distortion of the same pitch configuration in the direction X-rays shown in FIG. 21B and distortion of the projection of the voxel in the direction Z and distortion of the same pitch configuration in the direction X shown in FIG. 21C are similar distortions and hold the enlargement and contraction relationship.

Accordingly, data resampling is performed on the centering plane by interpolation or the like so that data items are arranged on a straight line at the same pitch. A result of the process is shown in FIG. 21A. In contrast, a projection point of the detector of point Xcp and Zcp to be resampled is calculated by equations (7') and (11') and a sampling data may be calculated by interpolating near data thereof.

The relationship between the coordinate systems Xcp and Zcp on the centering plane and the coordinate systems Xv and Zv of the reconstruction voxels is expressed by the following Equations (12) and (13) by applying Equations (5), (6), (9) and (10):

$$Xcp = \frac{FCD}{FCD'} \cdot Xv = \frac{FCD}{FCD + \frac{Yv}{\cos\phi}} \cdot Xv \quad (12)$$

$$Zcp = \frac{FXcp}{FCD''} \cdot Zv = \frac{\frac{\cos\phi}{\cos(\phi+\theta)} \cdot FCD}{\frac{\cos\phi}{\cos(\phi+\theta)} \cdot FCD + \frac{Yv}{\cos(\phi+\theta)}} \cdot Zv$$

$$= \frac{1}{1 + \frac{Yv}{FCD \cdot \cos\phi}} \cdot Zv \quad (13)$$

Therefore, when the axial slice of the slice position Z=Zcp of the reconstruction voxel is reconstructed, Zv is always made to be a constant in Equations (12) and (13), Yv is made to be a constant in the voxel column and Xv is changed in voxel units assuming that the axial slice is considered to be a circle FOV which inscribed a square shown in FIG. 21B. Thus, projection of a square (indicated by a dashed line) and its inscribed circle FOV is made to be a trapezoid (indicated by a dashed line) and modification (not shown) of a circle inscribed to the trapezoid.

A straight line obtained by projecting the voxel column to the centering plane is vertically moved in parallel in the centering plane to correspond to the position of the voxel column. Then the Z coordinate Zap corresponding to the voxel column to be backprojected is obtained by Equation (13), the X coordinate Xcp corresponding to the voxel to be backprojected is obtained by Equation (12). Then, corresponding data is backprojected to the subject voxel. The foregoing process is repeated for all of the voxels for all views so that backprojection is performed.

The foregoing fact is expressed as follows, wherein FdpD is the distance from the focal point to the detection device and FcpD (X, Z) is the distance from the focal point to the centering point.

$$Data\text{-}Conv = \left(\frac{FCD}{FdpD} \cdot Data\text{-}Raw\right) \times Conv\text{-}Function \quad (14)$$

$$Data\text{-}center = \frac{1}{FcdD^2(X)} \cdot Data\text{-}Conv \quad (15)$$

-continued $$Data\text{-}back = \left(\frac{A}{B}\right)^2 \cdot Data\text{-}Center \quad (16)$$

Equation (14) is an equation expressing data subjected to the convolution processing, Equation (15) is an equation expressing data subjected to the centering process, and Equation (16) is an equation expressing data backprojected to the voxel.

Equation (16) is made to be as follows:

$$Data\text{-}back = \left(\frac{Fcpd(X)}{(Fvoxe1D(X))}\right)^2 \cdot Data\text{-}Center \quad (17)$$

$$= \left(\frac{FcpD(X, Z)}{Fvoxe1D(X, Z)}\right)^2 \cdot \frac{1}{FcpD^2(X, Z)} \cdot Data\text{-}Conv$$

$$= \frac{1}{Fvoxe1D(X, Z)} \cdot Data\text{-}Conv$$

Equation (17) coincides with Equation (3) which is the three-dimensional reconstruction equation.

Figure 23:
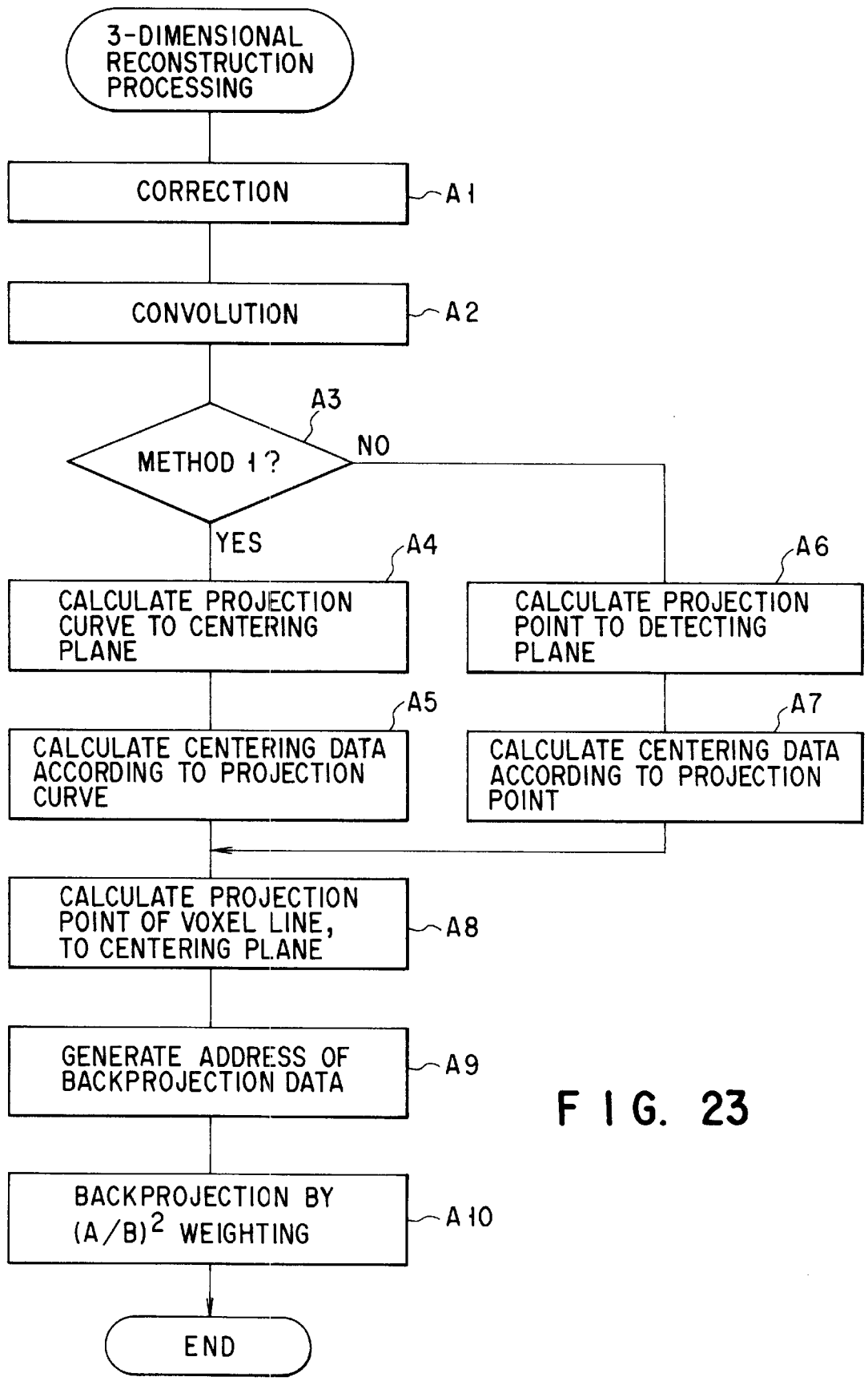
FIG. 23 is a flow chart showing a flow of a three-dimensional reconstruction processing to be performed by the reconstruction section of the X-ray CT apparatus according to the embodiment.

The three-dimensional reconstruction method (the cone beam reconstruction method) using the centering plane according to the projection will now be described with reference to FIG. 23.

(1) The reconstruction control section 21 subjects projection data Data-Proj supplied from the data acquisition section 11 to a correction process including the X-ray intensity correction so that raw data Data-Raw is obtained which is then stored in the first memory 23 (step A1).

(2) The reconstruction control section 21 causes the convolution processing section 22 to read data in the first memory 23 to read, and then subjects read data to the Feldkamp weighting process (the first term of Equation (14)). Then, the reconstruction control section 21 convolutes the result with the reconstruction function Conv-Function (the second term of Equation (14) to store a result of the convolution in the first memory 23 (step A2).

(3) The reconstruction control section 21 causes the first backprojection section 24 to perform the centering process in Equation (15) by either of the following steps (3-1) and (3-2) in accordance with convolution data stored in the first memory 23 (step A3).

Figure 22A:
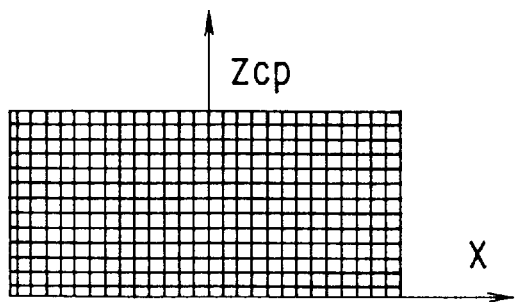
FIGS. 22A and 22B are diagrams showing data sampling, including an interpolation process on the centering plane in the reconstruction section of the X-ray CT apparatus according to the embodiment.
Figure 22B:
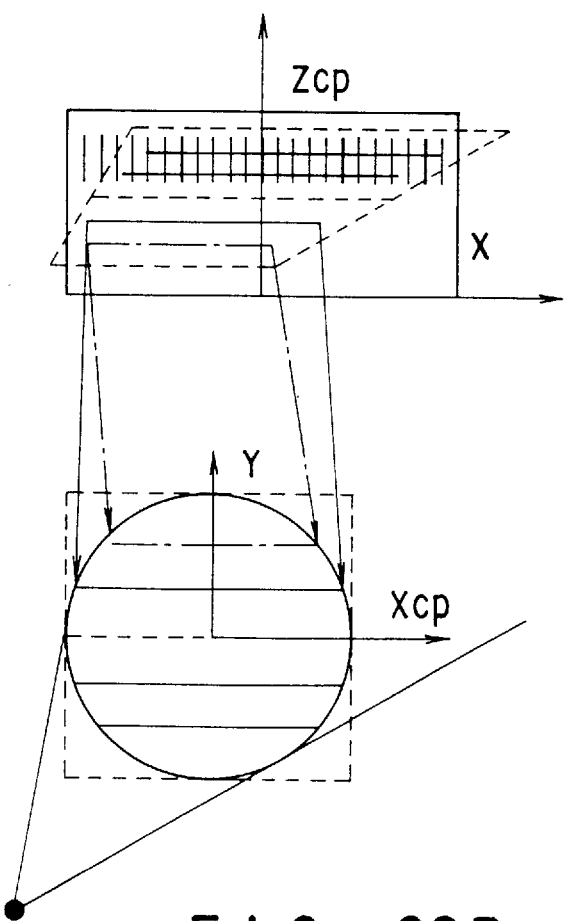

(3-1) In accordance with Equation (5) and Equation (11), projection curve formed by projecting data of the detector surface to the centering plane is calculated (step A4), and the convolution data is weighted. Then, the weighted data is projected to the centering plane so that the centering data is calculated (step A5). Then, centering data on the centering plane is resampled into the lattice shape as shown in FIG. 22A, and the resampled data is stored in the second data memory 25.

(3-2) In accordance with Equations (7') and (11'), positions of the projection points, at which the positions of lattice data items as resampled on the centering plane in (3-2) are projected to the detector surface are calculated (step A6). Convolution data of four detection devices (2 columns×2 CH) is weighted and added, and then weighted for the three-dimensional backprojection expressed in Equation (15) and projected to the centering plane so that the centering data Data-Center is calculated (step A7). A result of the calculation is stored in the second data memory 25.

(4) The reconstruction control section 21, in accordance with Equations (12) and (13), calculates projections points (a straight line) formed beams projecting voxels (a column), intended to be reconstructed, to the centering plane (step A8). Then, for example, four (2 columns×2 CH) data to be backprojected, are selected to generate the address of data above (step A9).

(5) The reconstruction control section 21 causes the second backprojection section 26 to read corresponding centering data Data-Center from the second data memory 25. If a plurality of data items are read, data above is weighted and added. Then, data is weighted with the square of A/B (the validity of which has been proved in Equation (17)) similarly to the backprojection of the centering data performed when the two-dimensional fan beam is reconstructed. Then, weighted data is added to the position of the subject voxel in the image memory 27 (step A10).

As a result, the three-dimensional reconstruction can be performed.

In the calculation of backprojection (projection) data from a point on the detector surface or the centering plane to the point on the centering plane or the voxel in the processes (3) and (5), resampling may be performed by a linear interpolation, such as four point Bi-Linear interpolation or a non-linear interpolation such as spline interpolation or another interpolation. The interpolation may be omitted but a point nearest the subject projection point may be calculated as Nearest Neighbor to calculate backprojection data.

In the four-point Bi-Linear interpolation, four points Data (j,n), Data (j,n+1), Data (j+1,n) and Data (j+1,n+1) of the j-th line, (j+1)th line, n-th channel and (n+1)th channel with respect to one projection point are subject of calculation so as to be interpolated.

At this time, the four-point Bi-Linear interpolation is performed by performing the following calculations:

$$CH(j)=Data(j,n) \times wch + Data(j,n+1) \times (1-wch)$$

$$CH(j+1)=Data(j+1,n) \times wch + Data(j+1,n+1) \times (1-wch)$$

$$SEG(j,j+1)=CH(j) \times wseg + CH(j+1) \times (1-wseg)$$

The foregoing process is sequentially repeated for a plurality of projection points. That is, $CH(j)$ is calculated, and then $CH(j+1)$ is calculated. In accordance with a result of the calculation above, $SEG(j,j+1)$ is calculated. Then, $CH(j)$ of a next projection point is calculated, and then $CH(j+1)$ is calculated. In accordance with a result of the calculation above, $SEG(j,j+1)$ is calculated. Then, the interpolation process is repeatedly performed for each projection point. The foregoing interpolation process takes a long time.

Accordingly, $CH(j)$ and $CH(j+1)$ are processed in parallel, and $SEG(j,j+1)$ is subjected to a pipeline process to connect the parallel process above. Thus, the time required to complete the process can be shortened such that the interpolation process is completed in substantially the same time required for the two-point interpolation process.

If the number of the centering columns is larger than the number of the voxel columns, a point nearest the subject projection point is selected as Nearest Neighbor to calculate the backprojection data. Thus, deterioration in the image can be prevented, and the number of calculations can be reduced to about 1/3 as compared with the four-point Bi-Linear interpolation so that the time required to complete the process is shortened.

In order to simplify the non-linear process in the channel direction and the weighting calculation at the time of backprojecting data similarly to the single slice CT (fan beam CT), the resampling process on the centering plane in the process (3) may be omitted to generate a projection curve corresponding to the centering data corresponding to the voxel intended to be backprojected in the process (4) though the description is omitted here. Although the projection curve is complicated in compensation for the omission of the resampling process, the total number of interpolation operations can be decreased.

As described above, according to the first embodiment, the three-dimensional backprojection is performed such that data is first projected to the centering plane so that the complicated correspondence between the columns of channels of the detectors disposed on the circular arc at the same angular intervals and the voxel columns disposed at the same pitch on the straight line can be simplified.

That is, the projection has the structure such that projection to the centering plane is first performed so that weights different for the voxel units required to perform the backprojection can collectively be calculated for each voxel column. Therefore, the number of the weight calculating operations can be reduced and the calculation can be simplified. If the number of the centering lines is increased in the foregoing embodiment, the accuracy in the interpolation can be improved.

As described above, according to the present invention, (non-linear) distortion in the direction Z at the time of performing the backprojection which is peculiar to the cone beam CT can be corrected by arranging data into the lattice form on the centering plane so that backprojection to the reconstruction voxel is performed easily. The foregoing correction can be realized by projection to the lattice centering points or performing resampling process.

Therefore, according to the present invention, the process of the second backprojection section 26 can be simplified and thus image can be reconstructed by the three-dimensional backprojection without a necessity of considerable expansion as compared with the conventional structure of the backprojection section for the two-dimensional backprojection (the fan beam reconstruction).

Although the foregoing embodiment (including the following embodiments) has been described about the cone beam X-ray CT apparatus having the cylindrical X-ray detector, the present invention is not limited to this. For example, a similar effect can be obtained when the projection is applied to a cm X-ray CT apparatus having a flat-type X-ray detector as shown in FIG. 24.

In this case, projection of a voxel line indicated by an arrow drawn with a continuous line and that indicated with an arrow drawn with a dashed line in the effective visual field FOV to the surface of the flat-type X-ray detector as shown in FIG. 25 is made as indicated by inclined arrows drawn by continuous and short dashed lines shown in FIG. 26. Therefore, although distortion (including non-linear distortion) in the channel direction (in the lateral direction) and distortion in the column direction (in the longitudinal direction) are not generated, the projection lines are in the form of inclined straight lines. Therefore, although the load of the calculation can be reduced as compared with the cylindrical X-ray detector, data selection and weight calculation for the backprojection are complicated considerably.

Accordingly, the centering processing, which is the backprojection (projection) processing to the centering plane, is, as shown in FIG. 27, performed in the present invention so that projection of the voxel column indicated by the continuous-line arrow and the dashed-line arrow in the effective visual field FOV to the surface of the flat-type X-ray detector enables the centering column for use in the backprojection for each voxel to be fixed. Therefore, data selection and weight calculation can be simplified.

Also in the case of using the flat type X-ray detector, the weight calculation required for the backprojection can be reduced from the calculation for voxel unit to voxel column unit similarly to the cylindrical X-ray detector. Moreover, increase in the number of the centering lines causes an effect for improving the accuracy of the interpolation to be improved similar to the case of the cylindrical X-ray detector.

The shape of the X-ray detector may be varied as well as the cylindrical shape and the flat shape. For example, the present invention may be applied to a trihedral (or an X-ray detector in the form of a polyhedron having a large number of planes) structure as shown in FIG. 28.

Although the projection line of the voxel column is, as shown in FIG. 29, formed into a bent line, the centering process similar to that performed in the case of the flat type X-ray detector causes the weight calculation to be simplified. Moreover, increase in the number of the centering columns enables the accuracy of the interpolation to be improved.

If the interpolation is repeated, blur or the image can be amplified. However, two times of the interpolation operations is required when projection to the centering plane is first performed and the backprojection to the voxel is performed in order to simplify the projection curve and the weight calculation. The interpolation method according to the present invention will now be described.

In the case where interpolation is performed one time as shown in FIG. 30, when voxel data DB is at a position at which it divides the distance from D1 to D2 at 8:1 with respect to (original) data positions (D1, D2, D3) when the detector column is backprojected to the voxel, DB is made to be as follows:

$$DB = (1/9) \times D1 + (8/9) \times D2.$$

Thus, the position is determined by the data positions D1 and D2 and interference of another data items, such as D3, can completely be eliminated.

In the case where interpolation is performed two times as shown in FIG. 31, when centering points Dc1 and Dc2 respectively are at positions at which Dc1 divides the distance from D1 to D2 at 5:4 and at which Dc2 divides the distance from D2 to D3 at 2:1 with respect to (original) data positions (D1, D2, D3) when the detector column is backprojected to the centering plane, Dc1 and Dc2 are made to be as follows:

$$Dc1 = (4/9) \times D1 + (5/9) \times D2$$

$$Dc2 = (1/3) \times D2 + (2/3) \times D1$$

When the voxel data (point) DB is at a point at which it divides the distance from Dc1 to Dc2 at 3:5, DB is made to be as follows:

$$\begin{aligned} DB &= (5/8) \times Dc1 + (3/8) \times Dc2 \\ &= (5/18) \times D1 + (17/36) \times D2 + (1/4) \times D3 \end{aligned}$$

That is, although the voxel data DB is actually positioned between D1 and D2, an interference item of D3 is added due to two times of the interpolation. Thus, items of D1 and D2 includes errors and therefore blur is amplified in the actual image.

Therefore, accuracy of the interpolation must be improved in order to prevent blur of the image.

The accuracy of the interpolation can be improved by either of the two methods below.

FIG. 32 is a diagram showing an interpolation method according to the present invention.

In order to coincide with the (original) data positions (D1, D2, D3) when the detector column is backprojected (projected) to the centering plane, centering points (Dc1, Dc4, Dc6) are set on the centering plane. Moreover, interpolation points (Dc2, Dc3, Dc5) are set between the centering points. As a result, blur occurring in the two times of the interpolation processes can be prevented.

If voxel data DB is at a position at which it divides the distance from Dc3 to Dc4 at 2:1, DB is expressed as follows:

$$\begin{aligned} DB &= (1/3) \times Dc3 + (2/3) \times Dc4 \\ &= (1/9) \times D1 + (8/9) \times D2 \end{aligned}$$

Thus, the interference term of D3 can completely be eliminated at the original data position. However, the projection curve of the detector column on the centering plane has a non-linear distortion. Thus, Zcp coordinates at which original detector data exists at the centering point between adjacent channels, that is, adjacent in the Xcp direction are made to be slightly different from each other. Therefore, interpolation points (centering points) cannot easily be set to the original data positions in all of the centering columns.

FIG. 33 is a diagram showing another interpolation method according to the present invention.

The number of the interpolation points (the centering points) to be located at the same pitch is increased as much as possible in consideration of the balance with the required calculation time. The existence of the interpolation point at the original data position is not always required. Since the number of the centering columns is made to be larger than at least the number of the detector columns, the interpolation accuracy can be improved at positions for the most part. Blur is generated due to the interpolation only when the second interpolation position (the voxel) is positioned between two interpolation points for the first time between which the original data position is interposed (for example, between Dc9 and Dc10).

When the voxel data DB is at a position at which it divides the distance from Dc8 and Dc9 at 1:1 for example, DB is expressed as follows:

$$\begin{aligned} DB &= (1/2) \times Dc8 + (1/2) \times Dc9 \\ &= (1/10) \times D1 + (9/10) \times D2 \end{aligned}$$

Thus, the interference term of D3 at the original data position is completely eliminated.

When voxel data DB is at a position at which it divides the distance from Dc9 to Dc10 at 1:1 (at a position corresponding to D2), DB is expressed as follows:

$$\begin{aligned} DB &= (1/2) \times Dc9 + (1/2) \times Dc10 \\ &= (1/40) \times D1 + (14/15) \times D2 + (1/24) \times D3 \end{aligned}$$

Although the interference term of D3 (also D1 corresponds in this case) is not eliminated, weights (coefficients) of D1 and D3 are smaller than that of D2. Therefore, blur can be prevented as compared with the conventional structure. Moreover, a range in which blur is generated is limited to a distance from Dc9 to Dc10.

Figure 34A:
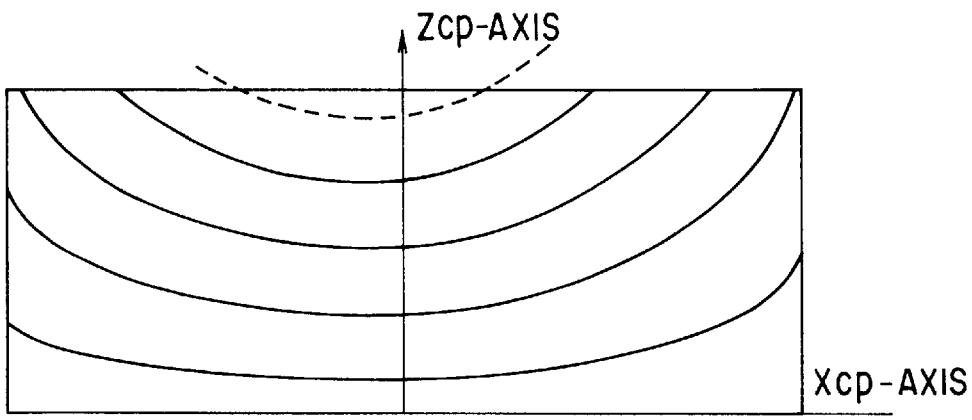
FIGS. 34A to 34C are diagrams showing a projection line of the five detector columns to the centering plane, a projection line of the voxel line to the centering plane when the number of the centering lines is five, the centering line to be weighted, a projection line of the voxel line to the centering plane when the number of the centering lines is ten, and the centering line to be weighted.
Figure 34B:
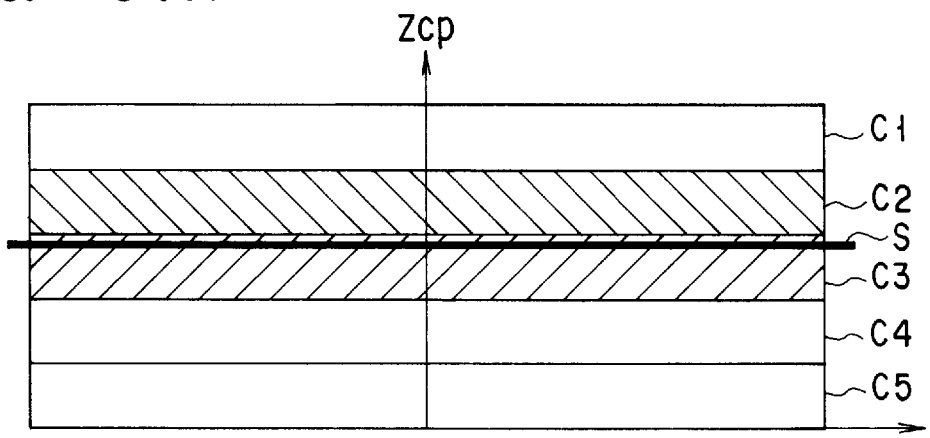

An example in which the foregoing fact is applied to the centering plane is shown in FIGS. 34A to 34B.

FIG. 34A shows a projection curve obtained by projecting the fifth line of the detector column to the centering plane. The projection curve is used to produce centering data in the lattice configuration by the above-mentioned centering process.

FIG. 34B shows a case in which the number of the lattice columns (the centering columns) is made to be five which is the same as the number of the detector columns. Referring to FIG. 34B, data position to be backprojected to a certain voxel column is assumed to be straight line S. In this case, interpolation is performed by using centering columns C2 and C3. Moreover, a coefficient is set in accordance with the respective ratios so that the coefficient of centering column C3 is larger than that of centering column C2.

Since the number of the centering columns is the same as the number of the detector columns, the width of data for use in the interpolation is widened in the direction of the Zcp axis and thus blur is generated in the foregoing case. The foregoing fact corresponds to the interpolation method shown in FIG. 31.

Figure 34C:
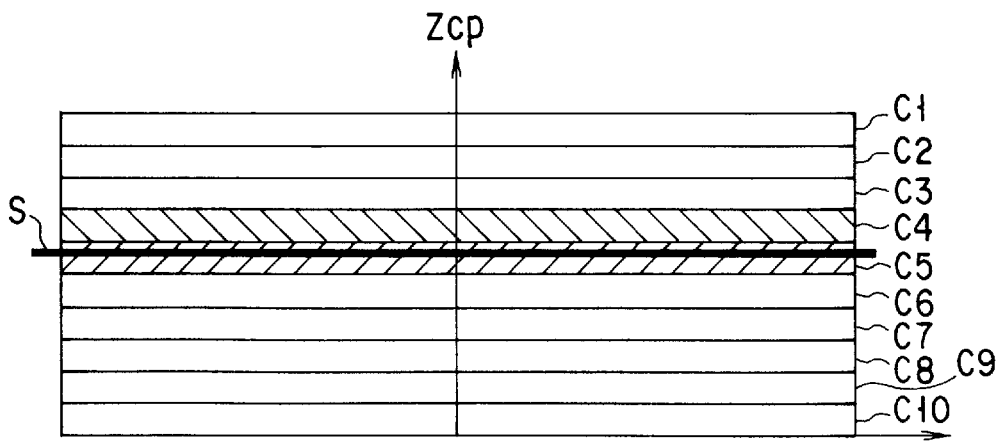

FIG. 34C is a diagram showing a case in which the number of the centering columns is made to be larger (ten) than that of the detector columns. Referring to FIG. 34C, making of the data position to be backprojected to a certain voxel column to be straight line S similar to the case shown in FIG. 34B, interpolation is performed by using the centering column subject C4 and C5. In this case, data for use in the interpolation is narrowed in the direction of the Zcp axis as compared with the case shown in FIG. 34B so that blur is prevented. The foregoing fact corresponds to the interpolation method shown in FIG. 33.

The interpolation method shown in FIG. 33 is a linear primary interpolation. As the interval between the centering columns is narrowed, the interpolation accuracy can be improved. Therefore, it is apparent that the interpolation accuracy at the point indicated by an arrow(in a case where DB is positioned between Dc8 and Dc9) is satisfactory.

The number centering columns with respect to the number of the detector columns may be enlarged considerably (for example, the number of the centering columns is made to be 50 or 500 with respect to 5 columns of the detectors) so as to perform the second interpolation by 0-order interpolation, that is, Nearest Neighbor in which the nearest centering column is selected.

As described above, according to the first embodiment, blur of data inevitably occurring when the interpolation is performed for the backprojection processing using the centering plane can be restricted minimum by improving the interpolation accuracy.

When interpolation is performed in the column direction by using data in two columns (in actuality, data for two channels is used in the channel direction so that two columns×two channels=4 data interpolation is performed), a data point, at which data for use in the interpolation is considerably different, is unintentionally generated.

Figure 35:
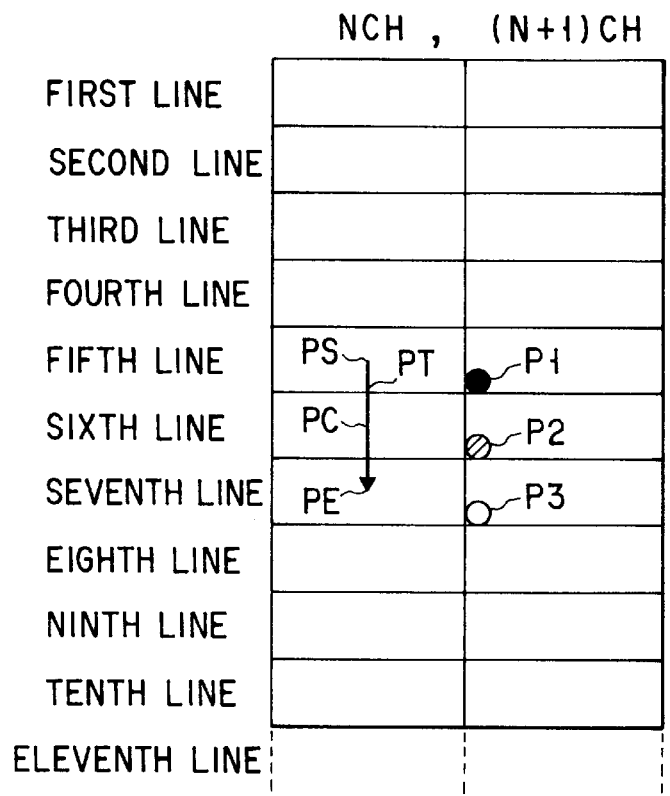
FIG. 35 is a diagram showing an example of data interpolation of 22 channels in a detector column in the reconstruction section of the X-ray CT apparatus according to the embodiment.

Referring to FIG. 35, an example of data interpolation between two channels (N channel and (N+1) channel) will now be described.

An interpolation method will now be described in which data surrounding projection points P1, P2 and P3 is interpolated to obtain DataA, DataB and DataC about the projection points P1, P2 and P3.

Two interpolation methods will now be described. Interpolation method 1 (Bilinear interpolation, that is, four near point interpolation) is arranged such that data in two columns is weighted in the column direction so as to be interpolated, while interpolation method 2 (process of bundling five columns, hereinafter a process for interpolating one data item by using a plurality of data items is called a "bundling" process) is a method in which data in five columns is weighted in the column direction so as to be interpolated.

In the description below, wi(i) indicates weight of the i-th line, wj(j) indicates weight of. the j-th channel, and Data(i,j) indicates data at the i-th line and j-th channel. Note that wi(i) and wj(j) have been standardized.

An interpolation equation by the interpolation method 1 is as follows:

$$\text{Data } A = \sum_{i=5}^{6} \sum_{j=N}^{N+1} [Wi(i) \cdot Wj(j) \cdot \text{Data}(i, j)]$$

$$\text{Data } B = \sum_{i=6}^{7} \sum_{j=N}^{N+1} [Wi(i) \cdot Wj(j) \cdot \text{Data}(i, j)]$$

$$\text{Data } C = \sum_{i=7}^{8} \sum_{j=N}^{N+1} [Wi(i) \cdot Wj(j) \cdot \text{Data}(i, j)]$$

An interpolation equation by the interpolation method 2 is as follows:

$$\text{Data } A = \sum_{i=3}^{7} \sum_{j=N}^{(N+1)} [Wi(i) \cdot Wj(j) \cdot \text{Data}(i, j)]$$

$$\text{Data } B = \sum_{i=4}^{8} \sum_{j=N}^{(N+1)} [Wi(i) \cdot Wj(j) \cdot \text{Data}(i, j)]$$

$$\text{Data } C = \sum_{i=5}^{9} \sum_{j=N}^{(N+1)} [Wi(i) \cdot Wj(j) \cdot \text{Data}(i, j)]$$

The above-mentioned interpolation method 2 has the step of weighting and adding data for three lines (the fourth line to the sixth line for Data A, and as for the residual one-fourth, data for upper and lower lines (the third line and the seventh line) is weighted with w(3) and w(7) (w(3)+w(7)= $\frac{1}{4}$) so that interpolation data is obtained.

A method of weighting each data for use in the interpolation when the point to be interpolated has been moved will now be described.

Figure 36:
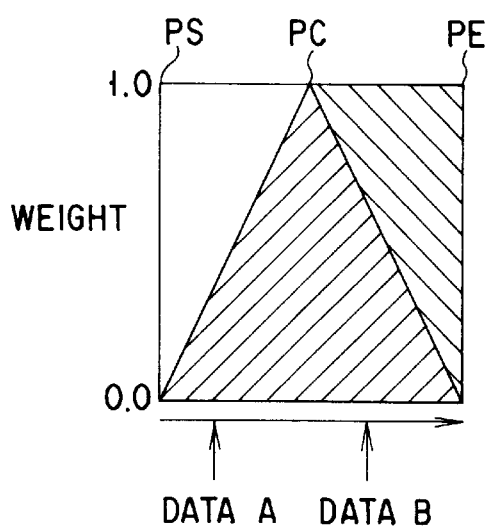
FIG. 36 is a diagram showing data interpolation method 1 for interpolating 22 channels in a detector column in the reconstruction section of the X-ray CT apparatus according to the embodiment.
Figure 37:
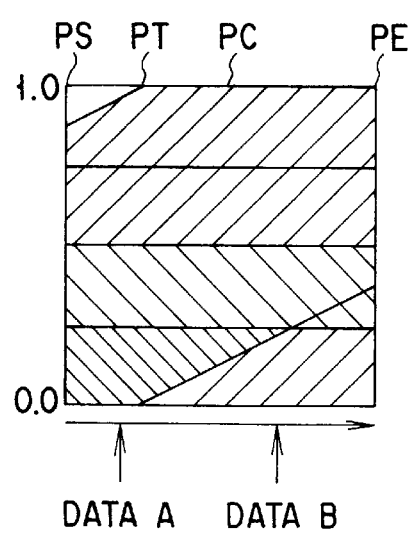
FIG. 37 is a diagram showing data interpolation method 2 for interpolating 22 channels in a detector column in the reconstruction section of the X-ray CT apparatus according to the embodiment.

Referring to FIG. 35, a case where the interpolation point has been moved from center PS of the fifth line to center PE of the seventh line will now be considered. FIGS. 36 and 37 are diagrams showing the relationship between the position of the interpolation point and weight of each data for each of the interpolation methods 1 and 2.

In the case of the interpolation method 1, the leftmost end PS is interpolated by only data on the fifth line. As the interpolation point is moved from left to right (in a direction from PS to PC in FIG. 35), weight of the sixth line is enlarged and that of the fifth line is reduced. At the central portion PC of the sixth line, the weight is only data on the sixth line. As the interpolation point is moved toward the seventh line, the weight of the sixth line is reduced, while the weight of data on the seventh line is enlarged. At the center PE of the seventh line, the weight is only data on the seventh line.

In the case of the interpolation method 1, change occurring near the center PC of the sixth line will now be considered. If the difference in the quality of data between the fifth line and the seventh line, between the fifth line and the sixth line, or between sixth line and the seventh line is great (the difference of data taking place due to the difference in the cone angle, characteristic of the detector or the scanning position), data interpolated in the vicinity of the center PC encounters an excessively large gap. Although the width of data for use in the interpolation is not more than data for two columns nearest the interpolation point, deterioration in the quality of an image caused from the above-mentioned gap sometimes raises a problem in the three-dimensional reconstruction using the cone beam CT.

In the case of the interpolation method 2, weights of the third to seventh lines respectively, are $\frac{1}{8}$, $\frac{1}{4}$, $\frac{1}{4}$, $\frac{1}{4}$ and $\frac{1}{8}$. The interpolation points on the boundary PT between the fifth line and the sixth line respectively are 0, $\frac{1}{4}$, $\frac{1}{4}$, $\frac{1}{4}$ and $\frac{1}{4}$ so that weight of the third line is made to be zero. Thus, four line data is uniformly weighted for the interpolation.

As a result, the eighth line is employed for the sixth line portion in place of the third line. Interpolation is performed by using data for the fourth line to the eighth line to the bound between the sixth line and the seventh line. When data switch for use in the interpolation in the vicinity of the boundary PT between the fifth line and the sixth line is considered, switch from the third line to the eighth line is generated. However, change attributable to the fourth to seventh lines does not substantially occur. Therefore, even if a gap is generated due to the difference in the quality of data caused from switch from the third line to the eighth line, its influence can be restricted. Therefore, the interpolation method 2 involves the width of data for use in the interpolation being enlarged to correspond to five lines. However, deterioration in the quality of the image occurring due to the gap generated attributable to switch of data can be prevented satisfactorily. The interpolation method 2 arranged to bundle data for three or more lines is able to further improve the quality of the image.

When the bundling processing is performed, the centering process according to the first embodiment may be employed simultaneously. The centering process may be omitted but only the bundling processing may be performed. Although the calculations for obtaining weights takes longer time as compared with the case where the centering process is performed, the quality of the image can be improved. A block diagram showing the essential structure of the reconstruction section 12 according to the present invention adaptable to the structure in which the centering process is not performed is shown in FIG. 38. The reconstruction section 12 shown in FIG. 38 has a structure such that the second data memory 25 and the second backprojection section 26 of the reconstruction section 12 shown in FIG. 13 are omitted. Since the other structures shown in FIG. 38 are the same as those shown in FIG. 13, description of the same structures is omitted here.

As an interpolation method in which data for a plurality of (Nc) lines not less than three lines is weighted and added, three methods may be available. A first method is a method in which weighting is performed when projection to the centering plane is performed, a second method is a method in which weight is performed when data to be backprojected from the centering plane is calculated, and a third method is a method in which weighting is performed when an image is reconstructed without projection to the centering plane as shown in FIG. 38.

Figure 40:
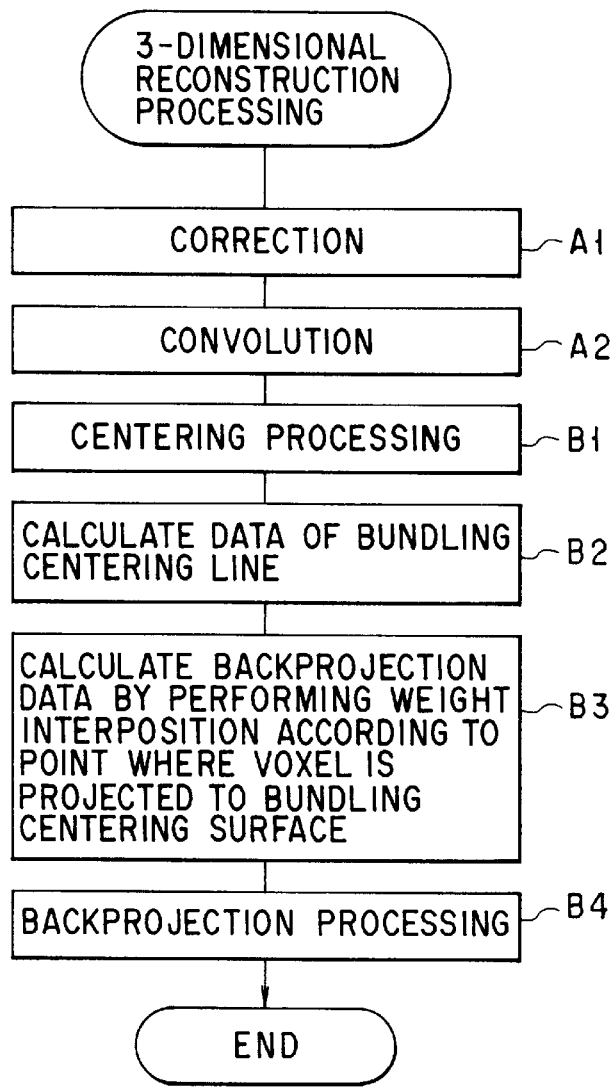
FIG. 40 is a flow chart showing the three-dimensional reconstruction processing using the bundling centering line in the reconstruction section of the X-ray CT apparatus according to the embodiment.

The first interpolation method will now be described with reference to FIGS. 39 and 40 in which interpolating is performed when Nc=5. Since the correction process and the convolution shown in FIG. 40 are the same as those shown in FIG. 23, the same reference numerals are given and the same portions are omitted from description.

(1) Centering data is produced by the above mentioned method (step B1). Data of the position of the first line is calculated for the first centering line (by, for example, projection to the detector).

(2) A line obtained by shifting the centering line by a half pitch is considered. Hereinafter, the shifted line is called as a "bundling centering line". Data of the centering line of the line (Nc-1) nearest each line of the bundling centering line is uniformly weighted so as to be used as data for the bundling centering line (step B2).

For example, bundling centering line data is produced as follows:

Data 1=(first line+second line)/2
Data 2=(first line+second line+third line+fourth line)/4
Data 3=(second line+third line+fourth line+fifth line)/4
Data 4=(third line+fourth line+fifth line+sixth line)/4
Data 5=(fourth line+fifth line+sixth line+seventh line)/4
Data 6=(fifth line+sixth line+seventh line+eighth line)/4
Data 7=(sixth line+seventh line+eighth line+ninth line)/4

(3) Data of two bundling centering lines nearest the point (an intersection of a straight line passing through a focal point and a voxel and the plane of the bundling centering line (hereinafter called a "bundling centering plane")) obtained by projecting the voxel to the bundling centering plane is interpolated by performing weighting with a value which is in inverse proportion to distance w so that backprojection data is obtained (step B3). For example, the following data is obtained.

Interpolation data of Data1 and Data2=w. Data1+(1−w). Data2

Interpolation data of Data2 and Data3=w. Data2+(1−w). Data3

Interpolation data of Data3 and Data4=w. Data3+(1−w). Data4

Interpolation data of Data4 and Data5=w. Data4+(1−w). Data5

Interpolation data of Data5 and Data6=w. Data5+(1−w). Data6

Interpolation data of Data6 and Data7=w. Data6+(1−w). Data7

In this case,

Interpolation data of Data4 and Data5 = $w \cdot$ Data4 + $(1 - w) \cdot$

Data5 = (fourth line + fifth line + sixth line)/4 + [$w$(third line) +

$(1 - w) \cdot$ (seventh line)]/4

(4) Backprojection data is backprojected in accordance with the above-mentioned three-dimensional reconstruction method (step B4).

Backprojection data calculated in the process (3) is the same as a result of interpolation performed by the interpolation method 2 in which data for a plurality of lines not less than three lines is used.

The interpolation method is not limited to the above-mentioned weighting calculation method. Any interpolation method may be employed if the selected method is arranged to perform the interpolation by using weighted data for three or more lines.

As described above, according to the interpolation method according to the first embodiment, deterioration in the quality of an image in the three-dimensional reconstruction processing caused from a great gap between data for interpolation can be prevented. Since one slice image (one tomography image) can be formed by data for three or more lines by the bundling processing, the time can be shortened as compared with a case in which an image for each line is reconstructed and then one slice image having a thickness larger than three lines is formed.

A second embodiment of the projection will now be described with reference to FIGS. 41 to 44.

As a method for shortening the time required to perform calculations for the backprojection, the following method may be employed in which a plurality of images are simultaneously reconstructed.

Although this embodiment will be described about the structure in which backprojection is performed by using the centering plane, the projection may be applied to all of three-dimensional backprojection methods which do not use centering.

Figure 41:
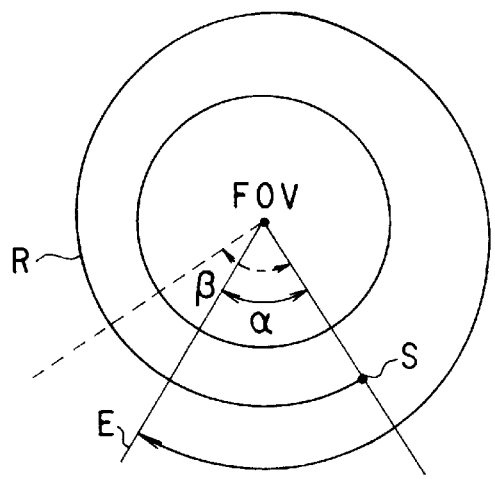
FIG. 41 shows a trajectory showing a revolution required for one image of the X-ray source and various angles concerning the trajectory in the X-ray CT apparatus according to a second embodiment of the present invention.

When the X-ray tube is, on trajectory R revolving the effective visual field FOV in which the subject is placed, at a position of certain angle b from reconstruction start angle S as shown in FIG. 41, phase q at this time is defined by positional relationship between the voxel and the reconstruction start angle S and the angle b. Referring to FIG. 41, the angle a is an angle of the overlap portion of the rotation and it is an angle required to perform overlap backprojection as described later.

FIG. 42 shows the relationship between cone beam and five slice images A to E at a certain phase θ. FIG. 43 shows a projection curve (a straight line) obtained by projecting each of the slice images A to E to the centering plane when backprojection is performed from voxel Va to voxel Vb.

As shown in FIG. 42, the position in the direction Z (the centering line) when data to be backprojected is selected is different. However, data of the same channel in the direction X (the centering channel) is backprojected to the same voxel. The foregoing fact is apparent that Equation (11) is independent from Z coordinate. Therefore, convolution data Data-Conv or centering data Data-Center obtained from the same projection data Data-Proj can be used to backproject to a plurality of slice images.

Since the calculations of the correspondence between the Xcp coordinate and the reconstruction voxel on the centering plane are the same, results of the calculations for the first slice image are stored so as to be used in a next slice. Thus, calculations can be reduced and therefore the time required for the reconstruction can be shortened.

An example for simultaneously reconstructing images A to E will now be described with reference to FIGS. 42 to 44. The correction process and the convolution shown in FIG. 44 are the same as those shown in FIG. 23, the same reference numerals are given and description of the same processes are omitted.

Although Feldkamp reconstruction for the static scan will now be described, a similar process is performed in the case of a Feldkamp-Helical reconstruction for the helical scan.

(1) Conv data at a certain phase θ is projected so that centering data is produced (step C1).

(2) Backprojection to image A is performed.

When backprojection to, for example, voxel line Va is performed, its projection curve is calculated (step C2). When the top (right) end voxel and the lower (left) end voxel of Va are projected, Z coordinate Z (A, Va) shown in FIG. 42 is calculated. The top and lower ends of the continuous line are made to be projection points XS(Va) and XE(Va) of the projection line obtained by projecting the image A to the voxel line Va. The projection points XS(Va) and XE(Va) are stored (step C3).

(3) A region from point XS(Va) to point XE(Va) is divided by the number of voxels to be backprojected so as to calculate the projection point of each voxel on each of the backprojection voxel line Va. Then, a predetermined interpolation process and a weighting process are performed, and then an obtained result is added to each voxel position (step C4).

(4) Similarly to processes (2) and (3), when backprojection to each voxel line is performed, the projection point of an end of the voxel line of the image A is calculated and stored. In accordance with the result of the calculation, backprojection to each voxel is performed. The voxel lines are sequentially shifted so as to be backprojected to the overall body of the image A (steps C2 to C6).

(5) Backprojection to the image Beams is performed.

When backprojection to, for example, voxel line Va is performed, projection of the upper and lower end voxels of Va is performed. Then, Z coordinate Z (B, Va) shown in FIG. 42 is calculated. The top and lower ends of the continuous line are made to be projection points XS(Va) and XE(Va) of the projection line of the voxel line Va of the image B.

Since the projection points XS(Va) and XE(Va) are the same as the result of the calculations about the image A, calculations may be omitted but the stored result of the calculation of the backprojection of the image A is read and Z coordinate Z(V, Va) of the projection line is calculated. Thus, the projection point of each voxel, that is, backprojection data can be selected. Selected data is subjected to a predetermined interpolation process and a weighting process, the processed data is added to the voxel position of the image memory.

As described above, the X coordinate of the projection point is performed by using a result of the image A and data is selected so as to be backprojected. The foregoing process is repeated to all of the voxel lines so as to be backprojected to the overall body of the image Beams (step C7).

(6) Similarly, backprojection to images C, D and E is performed (steps C7 and C8).

(7) The next phase θ+Δθ is processed similarly such that images A to E are simultaneously backprojected (steps C1 to C10) to complete backprojection of a required angle so that images A to E are reconstructed (step C11).

Although only the X coordinate of the projection point of the end of the voxel line is stored in the above-mentioned process, X coordinates of all of the projection points of the voxel line may be stored.

Also the calculation of the Z coordinate may be performed such that the Z coordinate of the projection points of the two ends (the right-hand and left-hand ends in FIG. 43) of the voxel line in the image is calculated. Then, the result of the calculation is divided by the number of the voxel lines to obtain the projection point of the required voxel line.

As an alternative to this, while performing backprojection of a required angle to the image A, the result of the calculations of the projection point may be stored to temporarily reconstruct the image A. Then, images B, C, D and E are reconstructed in this sequential order.

Since the Z coordinates of the projection points of symmetric images (for example, image A and image E or image B and image D) are symmetric coordinates, the result may be used.

Backprojection may be performed over each image in voxel units.

For example, the sequential order is as follows:
(voxel of image A-Vn), (voxel of image B-Vn),
(voxel of image C-Vn), (voxel of image D-Vn),
(voxel of image D-Vn), (voxel of image A-V(n+1)), . . .

Similarly, backprojection may be performed over each image in view units.

As described above, according to the second embodiment, the result of the calculation of the backprojection of the first image is used to calculate the backprojection of other images. Therefore, time required to reconstruct the image can be shortened.

A third embodiment of the present invention will now be described with reference to FIG. 45. According to this embodiment, a method of shortening time required to calculate backprojection when the centering plane is used to perform the backprojection will now be described.

In this embodiment, a plane running parallel to the centering plane is reconstructed. By using the plane above, the three-dimensional reconstruction can be performed in high speed.

When plane L running parallel to the centering plane C is reconstructed as shown in FIG. 45, the reconstructed plane L is in the form obtained by simply enlarging or contracting the centering plane. Therefore, the lateral direction (Xcp) data selection is the same. Thus, the calculation can be completed by only one time so that the calculation of data selection in the longitudinal direction (Zcp) is facilitated significantly.

As described above, according to the third embodiment, weighting for the backprojection is the same for the overall plane and thus the calculation can be completed by only one time. As a result, one image can significantly quickly be reconstructed.

Also the structure of the radiation CT apparatus can be simplified as compared with the conventional structure. For example, according to this embodiment, the apparatus can be realized by providing the functions of enlarging/contracting an image and multiplying a uniform coefficient to the overall body of the image.

A fourth embodiment of the present invention will now be described with reference to FIGS. 46 to 48.

The reconstructed image is defined by the following equation individually from Equation (1). Basically, the following definition equation is the same as Equation (1).

$$(\text{Image Reconstruction}) = \int \text{Back}(\theta, \text{data}) \, d\theta$$

In the definition equation above, the backprojection calculation Back($\theta$, data) for a certain phase q satisfy the following conditions (classification). In the following description, Back($\theta$, Dn) is a backprojection calculation at the n-th revolution for a certain phase q, and Back ($\theta$, D(n+1)) is a backproject calculation at the (n+1)th revolution for the phase $\theta$.

In the case of an overlap backprojection (in a case where $\theta$ corresponds to a range of the overlap angle a):

Back($\theta$, data)=Back($\theta$, Dn)×w+Back($\theta$, D(n+1))×(1−w)

In the case of another phase:

Back($\theta$, data)=Back($\theta$, Dn)

Then, the foregoing definition equation will now be described with reference to a flow chart shown in FIGS. 47 and 48. Since the correction process and the convolution shown in FIG. 47 are the same as those shown in FIG. 23, the same reference numerals are given and they are omitted from description. Referring to FIG. 48, the correction process and the convolution are the same as those shown in FIG. 23, and the centering process is the same as that shown in FIG. 40. The other same processes shown in FIG. 47 are given the same reference numerals and they are omitted from description.

Initially, a method for simultaneously reconstructing one image will now be described with reference to FIG. 47.

(1) The reconstruction control section 21 causes the first backprojection section 24 to calculate a data range required for the reconstruction from the relationship between the trajectory of the focal point and the reconstruction plane, and to project the convolution data Data-Conv to the centering plane so that centering data is produced (step D1).

At this time, whether each phase is required to be overlap-backprojected is determined (step D2). If the phase is required to be overlap-backprojected, data Dn at the N-th revolution is weighted with w(step D3) so that weighted centering plane projection data Data-Center-Wt is produced. Then, the second backprojection section 26 usually backprojects the projection data to the voxel (step D4). If the phase is not required to be overlap-backprojected, projection data is as it is backprojected (step D7).

(2) Then, the phase, which must be backprojected, is processed such that data D (n+1) at the (N+1)th revolution is weighted with (1−w) (step D5) so that weighted centering plane projection data Data-Center-Wt' is produced. Then, the produced projection data is usually backprojected (step D6).

(3) The processes in (1) and (2) are repeated for the required angle (for example, for 360°) calculated without overlap so as to be backprojected (steps D8 and D9).

As a result, backprojection for the required angle (for example, 360°+Overlap angle) with the overlap is performed so that the image is reconstructed.

In the above-mentioned procedure, the backprojecting order of data at the N-th revolution and that at the (N+1)th revolution which must be overlap-backprojected and data for the other phase is not limited.

After data at one revolution, that is, 360°, has been backprojected, data of the overlap angle may be additionally backprojected. Moreover, backprojection of data for two revolutions of the overlap angle may be performed simultaneously.

A reconstruction method for simultaneously reconstructing a plurality of images (one image included) will now be described with reference to FIG. 48.

(1) The reconstruction control section 21 causes the first backprojection section 24 to usually project all of convolution data Data-Conv of the phase (for example, 360°) required for the backprojection to the centering plane so that Data-Center is obtained (step B1).

(2) The reconstruction control section 21, for each reconstruction plane, calculates the phase which must be overlap-backprojected (step E1).

(3) When the reconstruction control section 21 backprojects projection data Data-Center to voxel line of each reconstruction plane, the reconstruction control section 21 determines whether the phase must be overlap-backprojected. If the phase must be overlap-backprojected (step E2), the reconstruction control section 21 generates weight obtained by multiplying the weight Wt-Back for the backprojection by weight Wt-OL of the overlap-backprojection so that the backprojection is performed (step E3). If the phase is not required to be overlap-backprojected (step E2), weighting for the usual backprojection is performed and the second backprojection section 26 performs the backprojection (step E4). That is, In a case where q is not required to be overlap-backprojected (step E4):

Data-Back($\theta$)=Wt-Back×Wt-OL×Data-Center

In a case where q must be overlap-backprojected (step E3):

Data-Back($\theta$)=Wt-Back×Data-Center (4) The process in (3) is repeated so that backprojection for a required angle (for example, 360°+overlap angle= 450°) is performed (steps E2 to D9).

At this time, the range of data for performing backprojection for a required angle is different for each image. For example, image E has the data range of 1 to 1250 views (0° to 450°), image D has the data range of 250 to 1500 views (100° to 550°), image C has the data range of 500 to 1750 views (200° to 650°) and so forth.

Although the foregoing embodiment has been described about the method using the centering plane, a similar backprojection can be performed even if the centering plane is not used. In this case, the convolution data is multiplied by the weight Wt-OL for the overlap-backprojection. Therefore, the backprojection method according to this embodiment is not limited to the three-dimensional reconstruction method using the centering plane.

As described above, according to the fourth embodiment, time required to perform the overlap-backprojection which is able to improve the quality of an image in the case of the helical scan can be shortened significantly.

Note that the three-dimensional reconstruction processing, which must be performed by the reconstruction control section 21, may be performed by combining the structures according to the first to fourth embodiments.

For example, the following sequential process may be employed.

(1) Projection data Data-Proj is subjected to X-ray intensity correction and correction of the sensitivity of the detector so that raw data Data-Raw is obtained.

(2) raw data Data-Raw is, together with the reconstruction function, subjected to the convolution processing so that convolution data Data-Conv is obtained.

(3) When the overlap-backprojection is performed with the helical scan, centering data Data-Center obtained by bundling Data-Conv is obtained.

(4) While performing overlap-backprojection, a plurality of images are simultaneously reconstructed at high speed so that the image reconstruction processing is completed.

When the overlap-backprojection is performed with the helical scan as the process (3) after the process in (2) has been performed, centering data Data-Center-Wt obtained by subjecting Data-Conv to the data bundling processing and the weighting process for the overlap-backprojection may be obtained.

As the process in (4), backprojection for a predetermined angle (for example, 360°) may be performed to reconstruct the image.

As an alternative to this, after the process in (2) has been performed, the process in (3) may be performed such that centering data Data-Center obtained by subjecting Data-Conv to the data bundling processing is obtained when the conventional scan is performed.

The process (4) may be performed such that backprojection for a predetermined angle (for example, 360°) is performed to reconstruct the image.

A fifth embodiment of the present invention will now be described with reference to FIGS. 49A to 49C and 50.

Figures 49A, 49B, 49C:
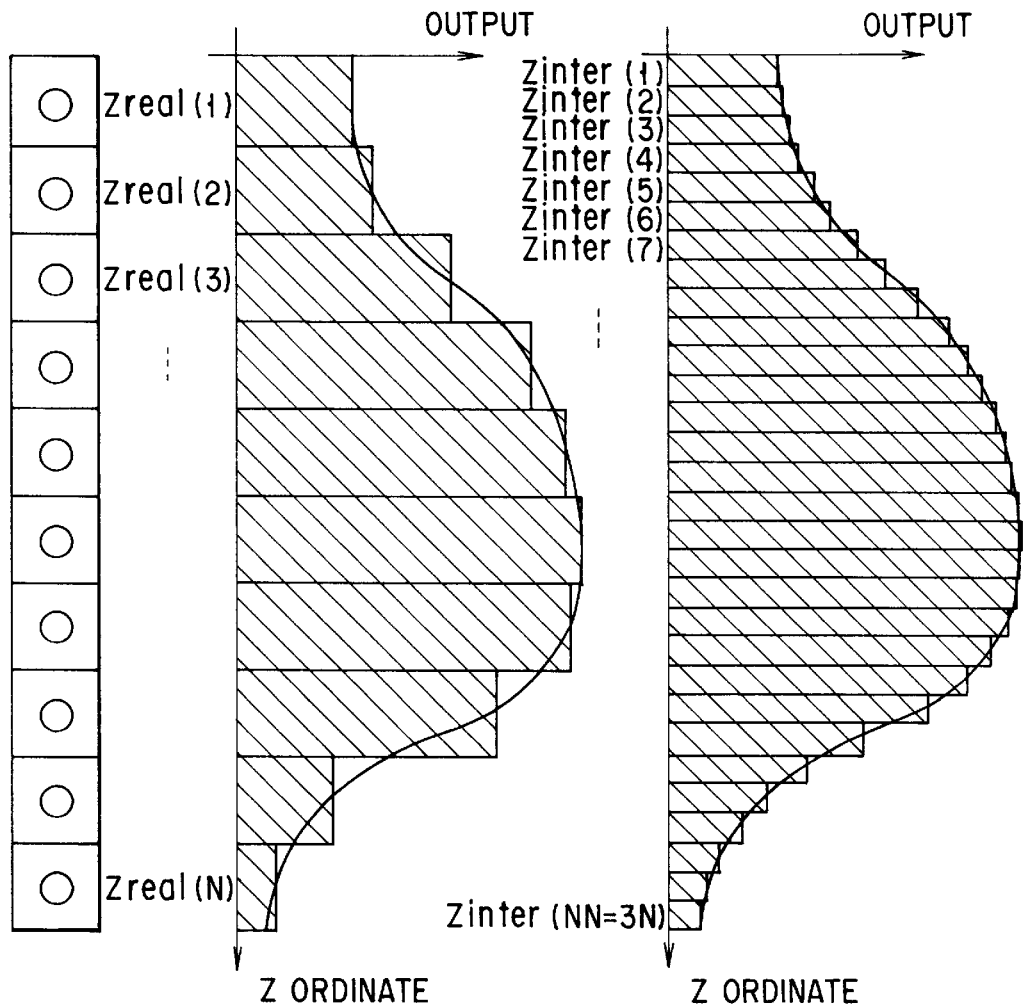
FIGS. 49A to 49C are diagrams showing a non-linear interpolation process of raw data from an X-ray detector in the reconstruction section of an X-ray CT apparatus according to a fifth embodiment of the present invention.

As shown in FIGS. 49A to 49C, this embodiment has a structure such that raw data for N lines is subjected to a non-linear interpolation process (for example, a fitting process using a spline function) to produce virtual detector data for NN (for example, 3N) lines. Then, each of the produced virtual detector data items is subjected to the convolution processing, and then backprojected. Note that FIG. 49A shows actual sampling positions. FIG. 49B shows output values at the sampling position Zreal(N) by a bar graph in the form of diagonal lines, and results of fitting the bar graph with a spline function is indicated by a curve. FIG. 49C shows output values at the position Zinter(NN) interpolated from the spline function shown in FIG. 49B by a bar graph in the form of diagonal lines.

The backprojection may be performed by the centering plane method. The bundling processing is performed by using the bundling centering line according to the first embodiment.

Figure 50:
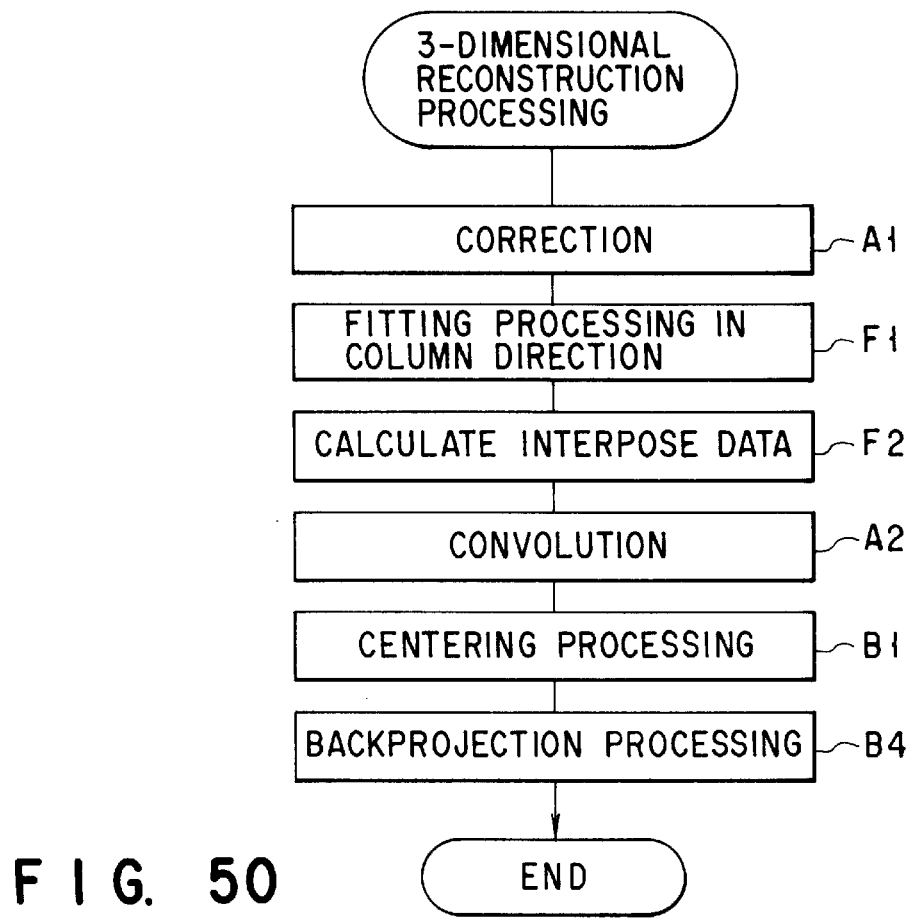
FIG. 50 is a flow chart showing the three-dimensional reconstruction processing for interpolating raw data for raising the sampling density before convolution is performed in the reconstruction section of the X-ray CT apparatus according to the embodiment.

The flow of the three-dimensional reconstruction processing will now be described with reference to FIG. 50.

(1) Raw data Data-Raw subjected to the various processes exists for N lines of the detectors (step A1). Raw data above is expressed as Data-Raw(N).

(2) The radiation CT apparatus 21 fits data in the same channel in the direction of the column with a spline function or the like (step F1).

(3) Then, data Data-Raw'(NN) at point Zinter(NN) between the actual sampling positions (Zreal(N) coordinate of each line) is calculated from the fitting function. Then, the outer portions of the first line and the N-th line are attached outwardly so that interpolation data Data-Raw'(NN), the sampling density of which is higher (point NN when the total beam thickness is NT) than the actual sampling density (point N when the total beam thickness is NT) is obtained (step F2).

At the actual sampling position (for example, Zreal(2)), actual data (for example, Data-Raw(2)) is employed as the interpolation data (for example, Data-Raw'(5)).

(4) Interpolation raw data Data-Raw', which has been interpolated in the process in (3) and thus the number of lines of which has been increased to be larger than the actual number N of the detector columns, is subjected to the convolution processing so that Data-Conv(NN) is obtained (step A2).

(5) Data Data-Conv(NN) for NN lines is subjected to the centering process so that Data-Center(NN) is obtained (step B1).

(6) Data-Center is, from the projection curve of each voxel line, backprojected to each voxel line (step B4).

In the above-mentioned process, centering may be omitted. Moreover, the following modification is permitted.

In the processes in (2) and (3), a simple non-linear interpolation or a linear interpolation may be employed.

In the processes in (2) and (3), the number NN may be increased to make interpolation 1 in the backprojection after the centering process has been performed may be 0-order interpolation, that is, Nearest Neighbor.

In the processes in (2) and (3), only data for a certain phase at a certain revolution is used to increase the number of the raw data lines. However, data for plural revolutions may be used to increase the number of raw data lines.

As described above, according to the fifth embodiment, employment of the bundling processing according to the first embodiment in the process in (5) enables the original object (to increase the number of lines and lines are bundled to be backprojected) to be achieved.

Figure 53:
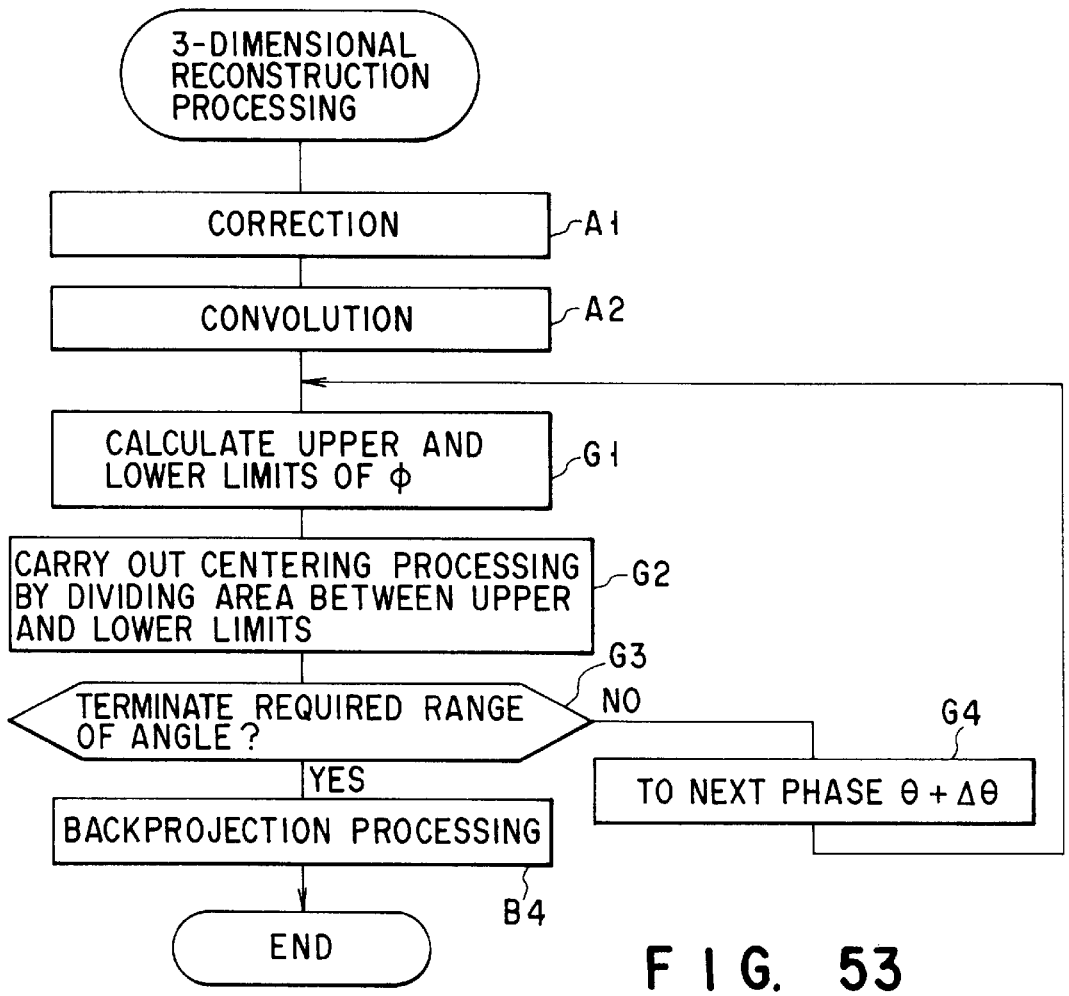
FIG. 53 is a flow chart showing the three-dimensional reconstruction processing for performing the centering process while limiting the centering range in the reconstruction section of the X-ray CT apparatus according to the embodiment.

A sixth embodiment of the present invention will now be described with reference to FIGS. 51 to 53. In the sixth embodiment, a method for reducing the capacity of the second data memory 25 will now be described.

Since the second data memory 25 is a memory for storing centering data, the capacity of centering data is required to be reduced. However, the accuracy in the interpolation is in proportion to the number of the centering lines (accurately, the density of the centering lines) as described in the first embodiment.

Figure 51:
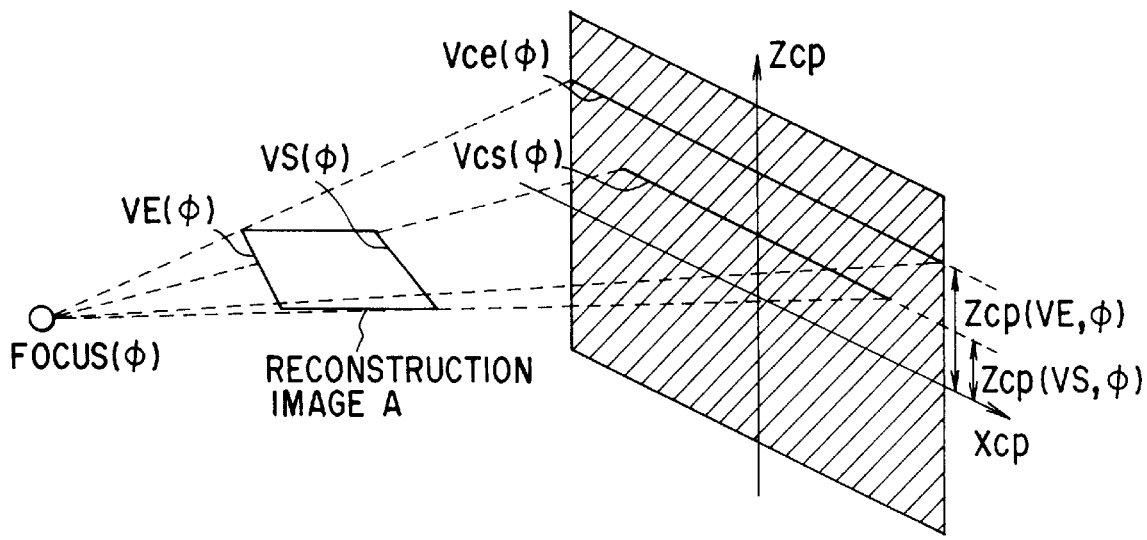
FIG. 51 is a diagram showing voxel lines VS(ϕ) and VE(ϕ) on image A at a certain phase ϕ and projection curve (straight line) Vcs(ϕ) and Vce(ϕ) of the voxel line to the centering plane when the image A is reconstructed in the reconstruction section of the X-ray CT apparatus according to a sixth embodiment of the present invention.

FIG. 51 is a diagram showing voxel lines VS($\phi$) VE($\phi$) on image A at a certain phase f and projection curves (straight lines) Vcs($\phi$) and Vce($\phi$) obtained by projecting the voxel lines to the centering plane for use to reconstruct the image A.

Centering data required to reconstruct a certain image A (a rectangular image) is not obtained from the overall region of the centering plane. Data above is obtained from a considerably limited range (a trapezoid) from Zcp(VE, $\phi$) to Zcp(VS, $\phi$) in the direction Z as well as in the direction X. Therefore, in order to reduce the capacity of the second data memory 25 while maintaining the density of the centering lines, only centering data in the necessary and sufficient range is required-to be stored in the second data memory 25.

That is, when images A to C shown in FIG. 42 are simultaneously reconstructed, only centering data in the positive region (in the case where the irradiation center is employed as the original point) on the Zcp coordinate is required to be stored by the second data memory 25.

Therefore, the storage capacity required for the second data memory 25 and time required to complete the calculation of centering data can be halved.

The method for reducing the storage capacity will now be described further in detail. In the description below, the reconstruction of images is performed one by one.

Specifically, as shown in FIGS. 52A to 52C, a data range required to reconstruct image A is calculated. Then, centering data in only the above-mentioned range is required to be calculated so as to be stored in the second data memory 25. In this case, the range to be stored is, accurately, region (the trapezoid region) Q shown in FIG. 52C. In order to simplify the operation, a rectangular region including the region Q may be employed. The reason for this is that limitation of the range in the direction Z is more effective in reducing the storage capacity as compared with the structure in which the range in the direction X is limited. Therefore, even if the limitation of the range in the X direction may be ignored but a rectangular shape may be employed in place of the trapezoid in order to satisfactorily obtain the effects of reducing the storage capacity and the quantity of calculations.

The operation will be specifically described with reference to FIGS. 52A to 52C and 53. Referring to FIG. 53, the correction process and the convolution are the same as those shown in FIG. 23, and the backprojection processing is the same as that shown in FIG. 40. Therefore, the same portions are given the same reference numerals and they are omitted from description.

(1) The radiation CT apparatus 21 calculates Z coordinate component Zv of (focal point), (reconstruction plane) vector and components L(VS) and L(VE) of (focal point), (voxel lines VS and VE at the ends of the reconstruction plane) vector in a direction perpendicular to the centering plane. By using the components above, distance FCD between the focal point and the rotation center and the following equation, the radiation CT apparatus 21 obtains upper and lower limits Zcp(VS, φ) and Zcp(VE, φ) in the required centering data range (step G1). The upper and lower limits are determined in accordance with the sign of Zv. Note that f is the focal point movement angle.

$$Zcp(VS, \phi) = Zv \times L(VS, \phi)/FCD \quad Zcp(VE, \phi) = Zv \times L(VE, \phi)/FCD \quad (18)$$

(2) The radiation CT apparatus 21 divides a range from Zcp(VS, f) to Zcp(VE, f) by the number of centering lines (for example, 10N) to calculate the position of each centering line, and then calculates centering data from the projection curve obtained by projecting each centering line to the detector surface to store the result of the calculation to the second data memory 25 (step G2).

(3) The foregoing processes in (1) and (2) are repeated so that all of data items for the required angle are subjected to a centering process (steps G1 to G4).

(4) The radiation CT apparatus 21 instructs the second backprojection section 26 to backproject centering data to all voxels on the reconstruction plane (step D4).

As described above, according to this embodiment, the backprojection method using the centering plane can be realized in such a manner that the capacity of the memory and the quantity of calculations can be reduced.

Since this embodiment enables the centering process to be performed by using a large number of centering lines (10N) in a small range from Zcp(VS, φ) to Zcp(VE, φ), the accuracy of the interpolation can be improved.

Also this embodiment may be applied to a case where a plurality of reconstruction planes are simultaneously reconstructed. In this case, a range required to reconstruct each plane is calculated and only the required range is subjected to the centering process so as to be stored in the second data memory 25.

In a case where the required ranges overlap, the capacity of the memory and the quantity of calculations can furthermore be reduced. In place of accurately calculating the upper and lower limits to minimize the quantity of calculations, a range somewhat larger than the upper and lower limits required for the calculations may be processed. In a case where a portion upper than the focal point is reconstructed, a method may be employed in which only data upper than Midplane is projected to the centering plane.

As described above, according to the sixth embodiment, the capacity of the memory and the quantity of calculations can be reduced to correspond to several lines (=3/20 to 5/20) or halved (for example, 10 lines of 20 lines=½). Therefore, significant effects can be obtained to raise the processing speed and to reduce the cost.

A seventh embodiment of the projection will now be described with reference to FIG. 54.

When data to be projected to the centering plane is calculated, it is necessary to calculate (1) a curve obtained by projecting a straight line on the centering plane to the detector surface or (2) a curve (a projection curve) obtained by projecting the detector column on the detector surface to the centering plane so as to calculate data to be projected to the centering plane.

In the case of (1), if the projection curve is obtained by projecting points (that is, all of the centering points) sampled finely on the straight line to the detector surface, the quantity of calculations is enlarged excessively. Then, a method of shortening the time required to complete the calculations will now be described in a case where the calculation speed of the multiplication and addition and that of the trigonometric function (sin/cos) are different from each other and the multiplication and addition can be performed quickly.

Note that Equations (7') and (11') for use in this embodiment are again shown below:

$$\theta = \tan^{-1}\left(\frac{Xcp \cdot \cos\phi}{FCD - Xcp \cdot \sin\phi}\right) \quad (7')$$

$$Zdet = \frac{FDD}{FXcp} \cdot Zcp \quad (11')$$

$$FXcp(k(n)) = \frac{L(\phi)}{\cos(\phi + \theta)} \quad (19)$$

$$= \{Xcp(k(n)) - Xf\}^2 + Yf\}^{1/2} \quad (20)$$

As can be deduced from Equations (11'), (19) and (20), Z coordinate Zdet of the projection point of each centering line is changed non-linearly with respect to the centering channel. However, the same is changed linearly with respect to Z coordinate Zcp of the centering line. Therefore, the upper and lower end lines of the centering line, that is, the first line and the NN line are projected to obtain Zdet (1, k) and Zdet (NN, k) and the distance are sectioned by 1/(NN-1) to obtain a position which is Z coordinate Zdet (j, k) of the projection of the centering line.

Sine Xdet (k) does not depend upon the centering line, the results are the same for all of the lines.

Figure 54:
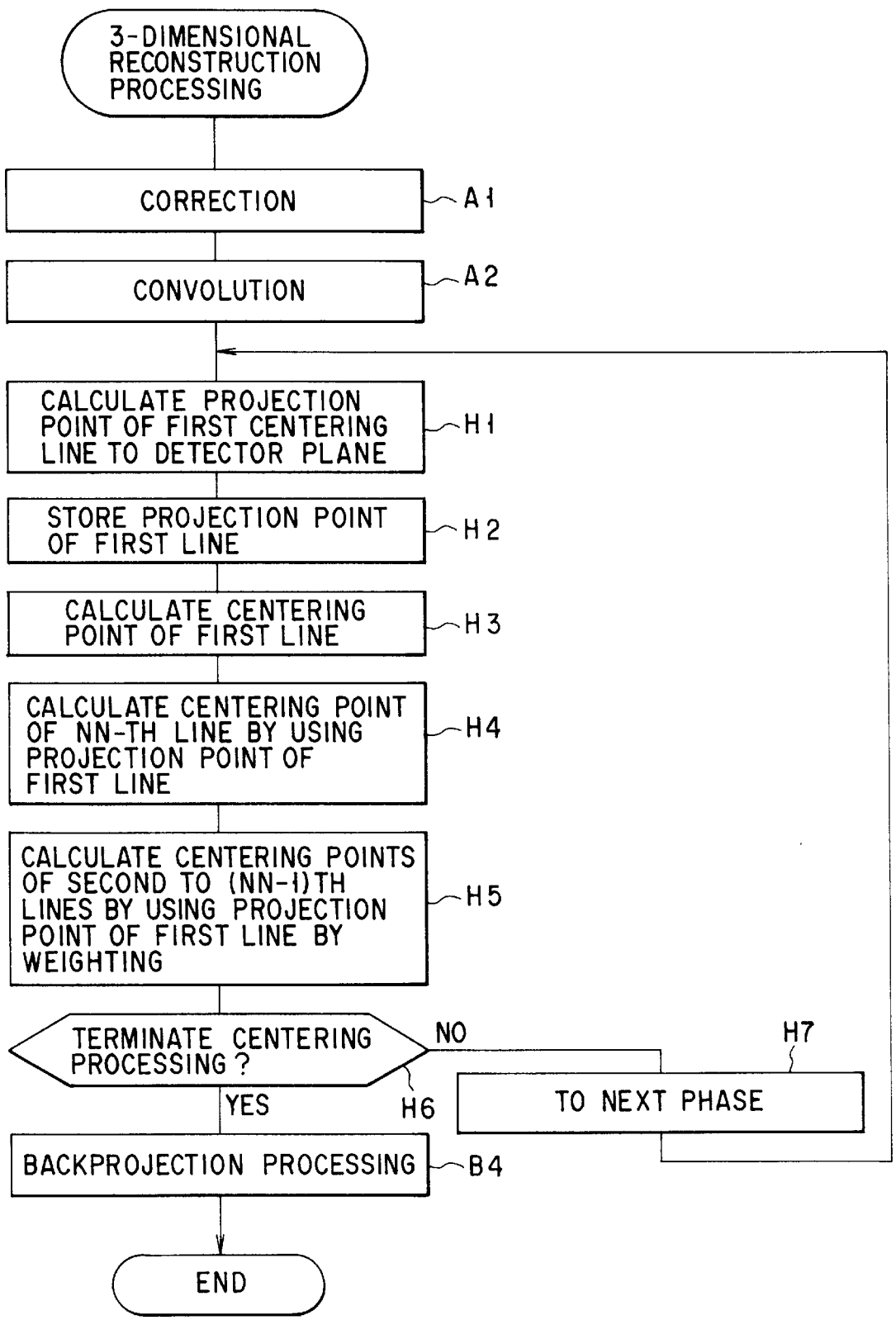
FIG. 54 is a flow chart showing the three-dimensional reconstruction processing in which a result of the calculation of the coordinates of the centering plane to the detector surface of the first line is used to calculate centering of another line in the reconstruction section of the X-ray CT apparatus according to the embodiment.

The flow of the above-mentioned three-dimensional reconstruction processing is shown in FIG. 54. Referring to FIG. 54, the correction process and the convolution are the same as those shown in FIG. 23 and the backprojection processing is the same as that shown in FIG. 40. Therefore, the same portions are given the same reference numerals and they are omitted from description.

(1) X and Z coordinates when all of the centering points of the first line are projected to the detector surface are obtained. By using the projection points, centering data of the first line is calculated (steps H1 to H3).

Xdet(1,1), Xdet(1,2), ..., Xdet(1,k), ..., Xdet(1,Nc)
Zdet(1,1), Zdet(1,2), ..., Zdet(1,k), ..., Zdet(1,Nc)

(2) Z coordinate when all of the centering points of the NN line are projected to the detector surface is obtained. As X coordinate, a result of the first line is used. By using the projection point, centering data of the NN-th line is calculated (step H4).

$$Xdet(NN, 1) = Xdet(1, 1), Xdet(nn, 2)$$
$$= Xdet(1, 2), \ldots, Xdet(NN, Nc)$$
$$= Xdet(1, Nc)$$
$$Zdet(NN, 1) = Zdet(NN, 2), \ldots, Zdet(NN, k), \ldots, Zdet(NN, Nc)$$

(3) Also X coordinate of the projection point of the centering point of the second line to (NN-1)th line is the result of the first line (step H5). By using Equation (20), the Z coordinate of the k-th centering point on the j-th line is obtained. By using the projection point, k-th centering data on the j-th line is calculated.

w(j)=(NN-j)/(NN-1)
Zdet(j,k)=w(j)×Zdet(1,k)+(1−w(j))×Zdet(NN,k)

(4) The processes in (1) to (3) are repeated so that all of the centering data items are calculated (steps H1 to H7).

Since Equation (20) is similar to Equation (10), the processing speed can be improved.

Since the projection curve is not changed complicatedly in the direction X (in the channel direction) as described in the first embodiment, satisfactory accurate approximation can be realized by cubic function. Therefore, it might be considered to use a fact that the approximation of the projection curve by the cubic function to raise the processing speed.

A method of obtaining a projection curve obtained by projecting a centering line to the detector surface will now be described. The following method may be applied to a case where a projection curve obtained by projecting the detector column to the centering plane is obtained to calculate the projection data to the centering plane.

(1) A case will be considered in which centering points (2000 points from k(1) to K(2000)) of the k-th centering line are projected to the detector surface.

(2) Xdet and Zdet coordinates Xdet (k(n)) and Zdet(k(n)) of the points on the detector surface when two ends k(1) and k(2000) and centering points, for example, k(100), k(200), ..., k(1900) located at arbitrary intervals are projected are calculated. For example, 21 times of calculations are performed for the two ends and the points located at an interval of 100 points so that 21 data items are obtained.

(3) Each of Xdet(k(n)) and Zdet(k(n)) are fit with an arbitrary function. It is preferable that a cubic natural spline function be employed for example. The fitting function enables certain coefficients (linear and quadratic derived functions) Xdet'(k(n)), Xdet"(k(n)), Zdet'(k(n)) and Zdet"(k(n)) to be obtained.

(4) Then, approximated projection points at all of the centering points are calculated from the fit function. In this case, a calculation equation for obtaining the centering point k(j), k(100) and k(200) is as follows:

$$h=K(200)-k(100)$$
$$a=(k(200)-k(j))/h, \quad b=(k(j)-k(100))/h$$

Assuming that the equation is as follows:

$$Xdet(k(j)) = a \cdot Xdet'(k(100)) + b \cdot Xdet'(k(200)) +$$
$$\left\{ (a^3 - a) \cdot Xdet''(k(100)) + \left\{ (b^3 - b) \cdot Xdet''(k(200)) \right\} \cdot \frac{h}{6} \right.$$
$$Zdet(k(j)) = a \cdot Zdet'(k(100)) + b \cdot Zdet'(k(200)) +$$
$$\left\{ (a^3 - a) \cdot Xdet''(k(100)) + \left\{ (b^3 - b) \cdot Xdet''(k(200)) \right\} \cdot \frac{h}{6} \right.$$

Centering data is obtained from the approximated projection point of the centering point calculated from the fitting function.

(5) The foregoing process is repeated so that all of required centering data items are obtained.

In the foregoing method, the lines are not limited to lines from the first line to the NN line. The necessary lines between the upper and lower lines may be used as the lines used in the calculation.

If the foregoing equation is subjected to a comparison with the foregoing equation for Xdet and Zdet (for example, Equation (5), calculations of the trigonometric function are not used.

As described above, according to the seventh embodiment, centering data is calculated such that the result of the calculation of the centering data on the first line is used to calculate centering data on the other lines so that the time required to complete the calculations is shortened.

An example of a process to be performed by the image reconstruction control section 21 for reconstructing an image by using the structures according to the above-mentioned embodiments will now be described. For example, the following flow of the process can be considered.

(1) Raw data Data-Raw is interpolated so that data Data-Raw', the sampling density of which is raised in the direction of the detector column, is obtained. Then, obtained data is, together with the reconstruction function, subjected to the convolution processing so that Data-Conv is obtained.

(2) A range of centering data required to reconstruct a required image is calculated. An assumption is made that the range is from Zcp(VS, φ) to Zcp(VE, φ).

(3) By making Vs(φ) and Vve(φ) which are the centering lines of Zcp(VS, φ) to Zcp(VE, φ) to be the upper and lower ends and by using a result of the calculation, centering data Data-Center is calculated at high speed.

(4) The second backprojection section 26 performs the backprojection so that image is reconstructed.

Figure 55:
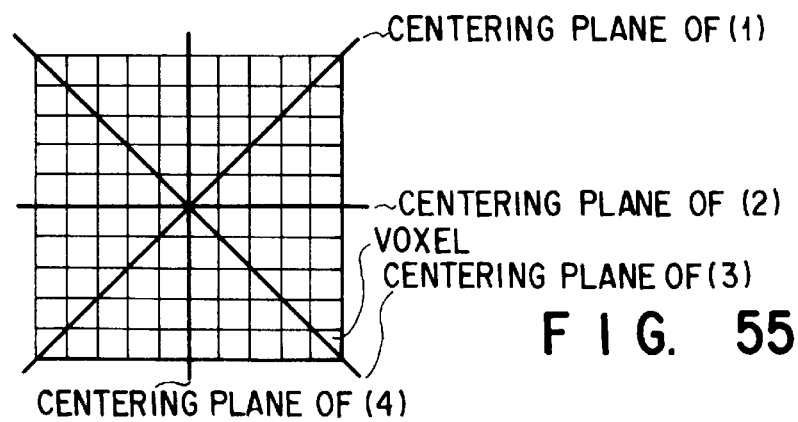
FIG. 55 is a diagram showing an example of configuration in a case wherein various centering planes are arranged.

Although the foregoing embodiments have been described such that the centering plane and the voxel line run parallel to each other, the present invention is not limited to this. For example, even if the centering plane and the voxel line are disposed to make an angle of 45°, calculation to the centering plane is permitted similarly to the case where the centering plane and the voxel line are disposed in parallel. An example of the configuration in a case that various centering planes are arranged is shown in FIG. 55.

Note that the numbers and interpolation methods are not limited. Moreover, the present invention is not limited to the structure in which backprojection is performed by using the centering plane. The present invention may be applied another backprojection method.

In the embodiments, processings of cos term multiplication, Z dependence term multiplication, channel direction convolution processing and weighting are described, a column direction convolution, multi-direction convolution or a method of performing two-dimensional processing of projection data on the detector surface before backprojection may be employed.

Regarding to a scanning method, a conventional (only rotation) scan, a scan assembled circle and straight line scan may be employed in addition to the helical scan.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

We claim:

1. A radiation CT apparatus comprising:
   a radiation source for irradiating a subject with radiations;
   detection means having at least two detector columns to detect radiations allowed to pass through the subject;
   means for obtaining data to be backprojected in accordance with data detected by said detection means; and
   image reconstruction means for reconstructing a transmitted image of the subject, wherein
   said image reconstruction means includes
      first backprojection means for backprojecting detected data to a predetermined centering plane, and
      second backprojection means for backprojecting data backprojected to a plurality of centering plane to said voxels corresponding to backprojected data.

2. A radiation CT apparatus according to claim 1, wherein the number of data lines of said centering plane is larger than the number of detected data lines.

3. A radiation CT apparatus according to claim 1, wherein said detection means has any one of a cylindrical shape, a flat shape and a polyhedral shape.

4. A radiation CT apparatus according to claim 1, wherein said centering plane is formed by two-dimensional data configuration.

5. A radiation CT apparatus according to claim 4, wherein the number of data lines of said centering plane is larger than the number of detected data lines.

6. A radiation CT apparatus according to claim 1, wherein data lines of said centering plane are disposed in parallel to a direction in which said plurality of voxels are backprojected.

7. A radiation CT apparatus according to claim 6, wherein the number of data lines of said centering plane is larger than the number of detected data lines.

8. A radiation CT apparatus comprising:
   a radiation source for irradiating a subject with radiations;
   detection means baying at least two detector columns to detect radiations allowed to pass through the subject;
   means for obtaining data to be backprojected in accordance with data detected by detection means; and
   image reconstruction means for reconstructing a transmitted image of the subject, comprising
      specifying means for specifying data to be backprojected in accordance with a three-dimiensional positional relationship between said radiation source and a plurality of voxels which are volume elements disposed in a three-dimensional space,
      comprising a table for specifying data to be backprojected in accordance with the three-dimensional positional relationship between said plurality of voxels and said radiation source, and means for specifying data to be backprojected in accordance with said positional relationship and said table, and
      backprojection means for backprojecting specified data to be backprojected to said plurality of voxels.

9. A radiation CT apparatus according to claim 8, wherein said detection means has any one of a cylindrical shape, a flat shape and a polyhedral shape.

10. A radiation CT apparatus comprising:
    a radiation source for irradiating a subject with radiations;
    detection means having at least two detector columns to detect radiations allowed to pass through the subject;
    means for obtaining data to be backprojected in accordance with data detected by said detection means; and
    image reconstruction means for reconstructing a transmitted image of the subject, comprising
       specifying means for specifying data to be backprojected in accordance with a three-dimensional positional relationship between said radiation source and a plurality of voxels which are volume elements disposed in a three-dimensional space,
       comprising means for calculating a projection curve obtained by projecting a plurality of voxel lines to said at least two detector columns in accordance with the three-dimensional positional relationship between said plurality of voxels and said radiation source, and means for specifying data to be backprojected, and
       backprojection means for backprojecting specified data to be backprojected to said plurality of voxels.

11. A radiation CT apparatus according to claim 10, wherein said detection means has any one of a cylindrical shape, a flat shape and a polyhedral shape.

12. A radiation CT apparatus comprising:
    a radiation source for irradiating a subject with radiations;
    detection means having at least two detector columns to detect radiations allowed to pass through the subject;
    means for obtaining data to be backprojected in accordance with data detected by said detection means; and
    image reconstruction means for reconstructing a transmitted image of the subject, wherein
    said image reconstruction means includes
       means for performing a bundling processing in a direction perpendicular to said detector columns in accordance with a plurality of detected data items and which performs backprojection to voxels which are disposed three-dimensionally in a space in accordance with data subjected to said bundling processing so as to reconstruct sectional image of the subject.

13. A radiation CT apparatus according to claim 12, wherein said detection means has any one of a cylindrical shape, a flat shape and a polyhedral shape.

14. A radiation CT apparatus according to claim 12, wherein said image reconstruction means includes
    first backprojection means for backprojecting detection data obtained by said detection means to a predetermined centering plane, and
    second backprojection means for backprojecting data backprojected to said centering plane to the corresponding voxels, and
    said first backprojection means bundles detection data in a column direction to backproject bundled detection data to said voxels when the backprojection is performed.

15. A radiation CT apparatus comprising:
    a radiation source for irradiating a subject with radiations;
    detection means having at least two detector columns to detect radiations allowed to pass through the subject;

interpolation means for performing an interpolation process in a column direction of detected data to raise the sampling density of detection data detected by said detection means; and image reconstruction means for reconstructing a transmitted image of the subject.

16. A radiation CT apparatus according to claim 15, wherein said image reconstruction means includes first backprojection means for backprojecting convoluted and weighted data to the centering plane; and second backprojection means for backprojecting data backprojected to a plurality of centering plane to said voxels corresponding to said data.

17. A radiation CT apparatus according to claim 15, wherein said detection means has any one of a cylindrical shape, a flat shape and a polyhedral shape.

18. A radiation CT apparatus comprising:

a radiation source for irradiating a subject with radiations;

detection means having at least two detector columns to detect radiations allowed to pass through the subject;

overlap weighting means which obtains a phase which must be weighted by an overlap process and which weights convolution data among data obtained from said detection means by convolution at the N-th revolution and the (N+1)th revolution corresponding to the phase which must be subjected to said overlap process for the purpose of performing the overlap-backprojection;

backprojection means for backprojecting data weighted by said overlap weighting means in a phase which must be subjected to said overlap process and, as it is, backprojecting data obtained by convolution in a phase which is not required to be subjected to the overlap process, and image reconstruction means for reconstructing a transmitted image of the subject.

19. A radiation CT apparatus according to claim 18, wherein said image reconstruction means includes first backprojection means for backprojecting convoluted and weighted data to the centering plane; and second backprojection means for backprojecting data backprojected to a plurality centering plane to said voxels corresponding to said data.

20. A radiation CT apparatus according to claim 18, wherein said detection means has any one of a cylindrical shape, a flat shape and a polyhedral shape.

21. A radiation CT apparatus comprising:

a radiation source for irradiating a subject with radiations;

detection means having at least two detector columns to detect radiations allowed to pass through the subject;

first backprojection means for backprojecting detection data obtained by said detection means to a centering plane set previously;

overlap weighting means which obtains a phase which must be weighted by an overlap process and which weights centering data among centering data backprojected by said first backprojection means corresponding to the phase which must be subjected to said overlap process for the purpose of performing the overlap-backprojection;

backprojection means for backprojecting data weighted by said overlap weighting means in a phase which must be subjected to said overlap process and, as it is, backprojecting centering data obtained by said first backprojection means in a phase which is not required to be subjected to the overlap process, and image reconstruction means for reconstructing a transmitted image of the subject.

22. A radiation CT apparatus according to claim 21, wherein said detection means has any one of a cylindrical shape, a flat shape and a polyhedral shape.

23. A radiation CT apparatus comprising:

a radiation source for irradiating a subject with radiations;

detection means having at least two detector columns to detect radiations allowed to pass through the subject;

means for obtaining data to be backprojected in accordance with detection data detected by said detection means, and image reconstruction means for reconstructing a transmitted image of the subject, wherein said image reconstruction means includes first backprojection means for backprojecting detection data obtained by said detection means to a centering plane, and second backprojection means for backprojecting data backprojected to said centering plane to corresponding voxels, and said second backprojection means calculates a projection curve obtained by projecting each voxel line of a first image to said centering plane, backprojects data of the centering plane to said voxels corresponding to the first image in accordance with a result of the calculation, and uses, for images ensuing a second image, the result of the calculation of the projection curve of the first image in backprojection of images ensuing the second image to said voxels corresponding to the first image.

24. A radiation CT apparatus according to claim 23, wherein said detection means has any one of a cylindrical shape, a flat shape and a polyhedral shape.

25. A radiation CT apparatus according to claim 23, wherein said first backprojection means weight data from the second line to a line right before the final line.

26. A radiation CT apparatus comprising:

a radiation source for irradiating a subject with radiations;

detection means having at least two detector columns to detect radiations allowed to pass through the subject;

means for obtaining data to be backprojected in accordance with detection data detected by said detection means, and image reconstruction means for reconstructing a transmitted image of the subject, wherein said image reconstruction means includes first backprojection means for backprojecting detection data obtained by said detection means to a centering plane, and second backprojection means for backprojecting data backprojected to said centering plane to voxels corresponding to said data, and said first backprojection means calculates a projection point of a first line of said centering plane to said detection means, calculates data in the first line of the centering plane in accordance with a result of the calculation, and uses a result of the calculation of the first line to data of a second and ensuing lines corresponding to the first line to calculate data of the second and ensuing lines.

27. A radiation CT apparatus according to claim 26, wherein said detection means has any one of a cylindrical shape, a flat shape and a polyhedral shape.

28. A radiation CT apparatus comprising:

a radiation source for irradiating a subject with radiations;

detection means having at least two detector columns to detect radiations allowed to pass through the subject;

means for obtaining data to be backprojected in accordance with detection data detected by said detection means; and image reconstruction means for reconstructing a transmitted image of the subject, wherein said image reconstruction means includes first backprojection means for backprojecting detection data obtained by said detection means to a centering plane, and second backprojection means for backprojecting data backprojected to said centering plane to voxels corresponding to said data, and said first backprojection means calculates a required centering range to backproject said detection data to a predetermined centering plane in accordance with said centering range.

29. A radiation CT apparatus according to claim 28, wherein said detection means has any one of a cylindrical shape, a flat shape and a polyhedral shape.

30. A radiation CT apparatus comprising:

a radiation source for irradiating a subject with radiations;

detection means having at least two detector columns to detect radiations allowed to pass through the subject;

means for obtaining data to be backprojected in accordance with detection data detected by said detection means; and image reconstruction means for reconstructing a transmitted image of the subject, wherein said image reconstruction means includes first backprojection means for backprojecting detection data obtained by said detection means to a centering plane, and second backprojection means for backprojecting data backprojected to said centering plane to voxels corresponding to said data, and said first backprojection means calculates a projection point function for obtaining a point of projection of a centering point of the centering plane to the detector surface, performs fitting the calculated projection point function with a predetermined function, and backprojects the fitted projection point function to the centering plane by an equation developed by a derived function of the projection point function.

31. A radiation CT apparatus according to claim 30, wherein said detection means has any one of a cylindrical shape, a flat shape and a polyhedral shape.

* * * * *